United States Patent
Saitou et al.

(10) Patent No.: US 6,756,343 B1
(45) Date of Patent: Jun. 29, 2004

(54) TRIKETONE DERIVATIVES AND HERBICIDE

(75) Inventors: Masatoshi Saitou, Chiba (JP); Hiroki Sekiguchi, Chiba (JP); Shinichiro Ogawa, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 0 days.

(21) Appl. No.: 09/806,948

(22) PCT Filed: Oct. 5, 1999

(86) PCT No.: PCT/JP99/05477

§ 371 (c)(1),
(2), (4) Date: Apr. 23, 2001

(87) PCT Pub. No.: WO00/20408

PCT Pub. Date: Oct. 5, 1999

(30) Foreign Application Priority Data

| Oct. 6, 1998 | (JP) | 10-284086 |
| Jun. 23, 1999 | (JP) | 11-177562 |
| Jun. 23, 1999 | (JP) | 11-177563 |

(51) Int. Cl.[7] .................... A01N 43/10; C07D 333/56
(52) U.S. Cl. ............................ 504/289; 549/58
(58) Field of Search ..................... 504/289; 549/58

(56) References Cited

U.S. PATENT DOCUMENTS

| 5,952,266 A | 9/1999 | Tseng |
| 5,981,439 A | 11/1999 | Kamano et al. |

FOREIGN PATENT DOCUMENTS

| WO | WO 97/01550 | 1/1997 |
| WO | WO 97/08164 | 3/1997 |
| WO | 97/08164 | * 3/1997 |
| WO | WO 97/09324 | 3/1997 |
| WO | WO 98/29406 | 7/1998 |
| WO | WO 98/35954 | 8/1998 |
| WO | WO 99/09023 | 2/1999 |

* cited by examiner

*Primary Examiner*—Deborah C. Lambkin
(74) *Attorney, Agent, or Firm*—Oblon, Spivak, McClelland, Maier & Neustadt, P.C.

(57) ABSTRACT

The present invention relates to a novel triketone derivative having a specific structure and a herbicide containing the triketone derivative as an active ingredient. The herbicide is effective for controlling weeds which inhibit growth of crop plants, inter alia, for paddy weeds such as *Sanwa millet* and *Scirups juncoides*.

18 Claims, No Drawings

TRIKETONE DERIVATIVES AND HERBICIDE

This application is a 571 of PCT/99/05477.

FIELD OF THE INVENTION

The present invention relates to a novel triketone derivative and a herbicide containing the triketone derivative as an active ingredient. More particularly, the invention relates to a triketone derivative useful for a herbicide effective on weeds which inhibit growth of crop plants, enter alia, for paddy field weeds such as *Echinochloa crus-galli* and *Scirups juncoides*, and to a herbicide containing the triketone derivative as an active ingredient.

BACKGROUND ART

Herbicides are important chemicals for facilitating weed control and enhancing productivity of field and garden crops. Therefore, development of herbicides which is safe and has excellent weed-controlling property even at a low dose have been actively carried out for many years.

There is proposed a herbicide containing a triketone derivative having a bicyclic benzoyl structure as an active ingredient, for the herbicide has excellent safety to field crops and excellent weed-controlling activity to field weeds. For example, there is proposed a herbicide containing a compound disclosed in Japanese Patent No. 2579663 and International Patent Publication WO97/08164 as an active ingredient, which herbicide has an excellent weed-controlling property suitable for growth of field crops. However, a herbicide containing such a compound as an active ingredient has poor activity for controlling paddy field weeds, and disadvantageously has insufficient safety to a paddy rice plant.

DISCLOSURE OF THE INVENTION

In view of the foregoing, an object of the present invention is to provide a herbicide containing a triketone derivative as an active ingredient, which herbicide can control a wide range of weeds at a low dose and imparts a low level of chemical injury to cultivated crops, particularly a paddy rice plant.

In order to attain the above object, the present inventors have conducted earnest studies, and have found that a triketone derivative having a specific chemical structure can control a wide range of weeds at a low dose and imparts a low level of chemical injury to cultivated crops. The present invention has accomplished based on this finding.

The present invention includes first and second aspects as described below.

The first aspect of the present invention encompasses the following.

(1) A triketone derivative represented by formula [I-1]:

[I-1]

wherein R represents a methyl group; each of X and Y represents a hydrogen atom, a halogen atom, a nitro group, an amino group, a cyano group, a hydroxy group, a mercapto group, —$R^1$, —$OR^1$, —$SR^1$, —$SO_2R^1$, —$NR^2R^3$, or —$NHCOR^1$, wherein $R^1$ represents a C1–C6 alkyl group which may have a branched structure, a cyclic structure, or an unsaturated bond, a C1–C6 haloalkyl group which may have a branched structure, a cyclic structure, or an unsaturated bond, a phenyl group which may be substituted, or a benzyl group which may be substituted; each of $R^2$ and $R^3$ represents a hydrogen atom, a C1–C6 alkyl group which may have a branched structure, a cyclic structure, or an unsaturated bond, a C1–C6 haloalkyl group which may have a branched structure, a cyclic structure, or an unsaturated bond, a phenyl group which may be substituted, or a benzyl group which may be substituted, or $R^2$ and $R^3$ may be bonded to each other to form a group having a cyclic structure; M represents a hydrogen atom, an alkali metal, an alkaline earth metal, or an organic base; $R^4$ represents a hydrogen atom or a C1–C6 alkyl group; and m is an integer between 0 and 4 inclusive; provided that not all of X, Y, and $R^4$ simultaneously represent methyl groups.

(2) A triketone derivative represented by formula [I-2]:

[I-2]

wherein R, X, Y, M, and m have the same definitions as described in relation to formula [I-1].

(3) A triketone derivative represented by formula [I-3]:

[I-3]

wherein R, X, M, $R^4$, and m have the same definitions as described in relation to formula [I-1].

(4) A triketone derivative represented by formula [1-4):

[I-4]

wherein R represents a methyl group; each of X and Y represents a hydrogen atom, a halogen atom, a nitro group, a cyano group, —$R^1$, —$OR^1$, —$SR^1$, or —$NR^2R^3$, wherein $R^1$ represents a C1–C6 alkyl group which may have a branched structure, a cyclic structure, or an unsaturated bond, a C1–C6 haloalkyl group which may have a branched structure, a cyclic structure, or an unsaturated bond, a phenyl group which may be substituted, or a benzyl group which may be substituted; each of $R^2$ and $R^3$ represents a hydrogen atom, a C1–C6 alkyl group which may have a branched structure, a cyclic structure, or an unsaturated bond, a C1–C6 haloalkyl group which may have a branched structure, a cyclic structure, or an unsaturated bond, a phenyl group which may be substituted, or a benzyl group which may be substituted, or $R^2$ and $R^3$ may be bonded to each other to form a group having a cyclic structure; Z represents —$OR^1$, —$SO_pR^1$, —$A(CH_2)_nQR^1$, —$NR^2R^3$, —$N(OR^1)R^2$, —$O(C=O)R^1$, —$O(C=O)OR^1$, —$O(C=O)SR^1$, —$O(C=O)NR^2R^3$, or —$O(C=S)NR^2R^3$ (wherein $R^1$, $R^2$, and $R^3$ have the same definitions as described in relation to X and Y, each of A and Q represents an oxygen atom or a sulfur atom, p is 0, 1, or 2, n is 1 or 2), —OM (wherein M represents a hydrogen atom, an alkali metal, an alkaline earth metal, or an organic base), or a halogen atom; and m is an integer between 0 and 4 inclusive.

(5) A triketone derivative according to (4), wherein Z represents an —OM group (wherein M represents a hydrogen atom, an alkali metal, an alkaline earth metal, or an organic base).

(6) A triketone derivative according to any one of (1), (2), (4), and (5), wherein Y represents a hydrogen atom, a C1–C6 alkyl group, or a halogen atom.

(7) A triketone derivative according to any one of (1), (2), (4), and (5), wherein Y represents a hydrogen atom or a methyl group.

(8) A triketone derivative according to any one of (2), (4), and (5), wherein Y represents a hydrogen atom.

(9) A triketone derivative according to any one of (1) to (8), wherein X represents —$R^1$, —$OR^1$, or —$SR^1$.

(10) A triketone derivative according to (1) or (9), wherein X represents a halogen atom or a methyl group.

(11) A triketone derivative according to any one of (1) to (10), wherein M represents a hydrogen atom.

(12) A herbicide containing a triketone derivative as recited in any one of (1) to (11) as an active ingredient.

(13) A herbicide for use in cultivation of a paddy rice plant, which herbicide contains a triketone derivative as recited in any one of (1) to (11) as an active, ingredient.

The second aspect of the present invention encompasses the following.

(1) A triketone derivative represented by formula [II-1]:

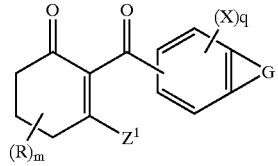

[II-1]

wherein R represents a methyl group; X represents a hydrogen atom, a halogen atom, a nitro group, an amino group, a cyano group, a hydroxy group, a mercapto group, —$R^1$, —$OR^1$, —$SR^1$, —$SO_2R^1$, —$NR^2R^3$, or —$NHCOR^1$ (wherein $R^1$ represents a C1–C6 alkyl group which may have a branched structure, a cyclic structure, or an unsaturated bond, a C1–C6 haloalkyl group which may have a branched structure, a cyclic structure, or an unsaturated bond, a phenyl group which may be substituted, or a benzyl group which may be substituted; each of $R^2$ and $R^3$ represents a hydrogen atom, a C1–C6 alkyl group which may have a branched structure, a cyclic structure, or an unsaturated bond, a C1–C6 haloalkyl group which may have a branched structure, a cyclic structure, or an unsaturated bond, a phenyl group which may be substituted, or a benzyl group which may be substituted, or $R^2$ and $R^3$ may be bonded to each other to form a group having a cyclic structure);

G contains 3 to 5 ring-constituting atoms which form a 5- to 7-membered saturated or unsaturated condensed ring including two carbon atoms of the benzene ring adjacent to G, wherein two or less ring-constituting atoms are selected from among nitrogen, oxygen, and sulfur, and the ring-constituting atoms may have one or more substituents selected from among a C1–C6 alkyl group, a C1–C6 haloalkyl group, a C1–C6 alkoxy group, a C1–C6 haloalkoxy group, a hydroxy group, a mercapto group, an oxo group, a thioxo group, a hydroxyimino group, a C1–C6 alkoxyimino group, a hydrazono group, a C1–C6 monoalkylhydrazono group, and a C1–C6 dialkylhydrazono group, and a carbon atom or the adjacent carbon atom of the ring-constituting atom may have a substituent selected from among an ethylenedioxy group, an ethylenedithio group, a propylenedioxy group, and a propylenedithio group, with these substituents optionally being substituted with a halogen atom or a C1–C6 alkyl group;

$Z^1$ represents a halogen atom, —$OR^1$, —$SO_pR^1$, —$A(CH_2)_nQR^1$, —$NR^2R^3$, —$N(OR^1)R^2$, —$O(C=O)R^1$, —$O(C=O)OR^1$, —$O(C=O)SR^1$, —$O(C=O)NR^2R^3$, or —$O(C=S)NR^2R^3$ (wherein $R^1$, $R^2$, and $R^3$ have the same definitions as described in relation to X, each of A and Q represents an oxygen atom or a sulfur atom, p is 0, 1, or 2, n is 1 to 3), or a halogen atom; m is an integer between 0 and 4 inclusive; and q is 1 or 2.

(2) A triketone derivative according to (1), which is represented by formula [II-2] or [II-3]:

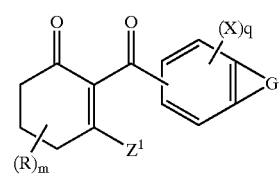

[II-2]

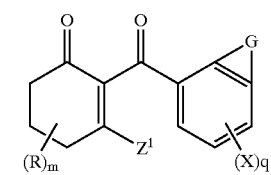

[II-3]

wherein R, X, G, $Z^1$, m, and q have the same definitions as described in relation to formula [II-1].

(3) A triketone derivative according to (1) or (2), which is represented by any one of formulas [II-4] to [II-9]:

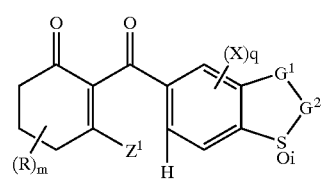

[II-4]

-continued

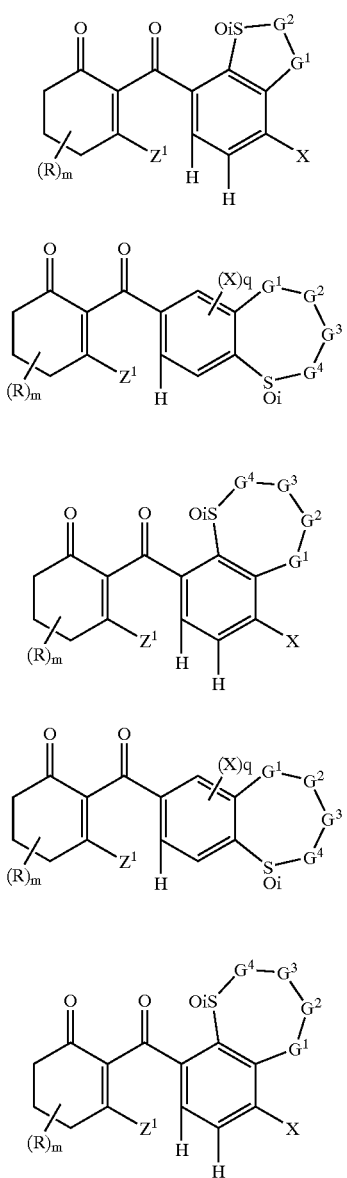

[II-5]
[II-6]
[II-7]
[II-8]
[II-9]

wherein R, X, G, $Z^1$, m, and q have the same definitions as described in relation to formula [II-1], each of $G^1$ to $G^4$ represents an optionally substituted atom that constitutes G in formula [II-1], and i is 0, 1, or 2.

(4) A triketone derivative according to any one of (1) to (3), wherein X represents a halogen atom, —$R^1$, —$OR^1$, or —$SR^1$.

(5) A triketone derivative according to (3) or (4), wherein each of $G^1$ to $G^4$ represents a ring-constituting atom having one or more substituents selected from the substituent group consisting of an unsubstituted or C1–C6 alkyl group, a C1–C6 alkoxy group, an oxo group, and a C1–C6 alkoxyimino group.

(6) A triketone derivative according to any one of (1) to (5), wherein $Z^1$ is selected from among a halogen atom, —$OR^1$, —$SO_pR^l$, —$A(CH_2)_nQR^1$, and —$N(OR^1)R^2$.

(7) A triketone derivative represented by formula [II-10]:

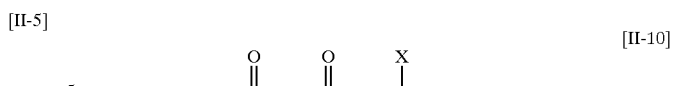
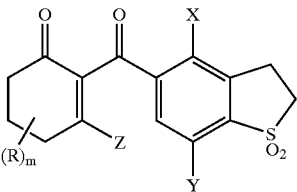

wherein R represents a methyl group; each of X and Y represents a hydrogen atom, a halogen atom, a nitro group, a cyano group, —$R^1$, —$OR^1$, —$SR^1$, or —$NR^2R^3$ (wherein $R^1$ represents a C1–C6 alkyl group which may have a branched structure, a cyclic structure, or an unsaturated bond, a C1–C6 haloalkyl group which may have a branched structure, a cyclic structure, or an unsaturated bond, a phenyl group which may be substituted, or a benzyl group which may be substituted, each of $R^2$ and $R^3$ represents a hydrogen atom, a C1–C6 alkyl group which may have a branched structure, a cyclic structure, or an unsaturated bond, a C1–C6 haloalkyl group which may have a branched structure, a cyclic structure, or an unsaturated bond, a phenyl group which may be substituted, or a benzyl group which may be substituted, or $R^2$ and $R^3$ may be bonded to each other to form a group having a cyclic structure); Z represents —$OR^1$, —$SO_pR^1$, —$A(CH_2)_nQR^1$, —$NR^2R^3$, —$N(OR^1)R^2$, —$O(C=O)R^1$, —$O(C=O)OR^1$, —$O(C=O)SR^1$, —$O(C=O)NR^2R^3$, or —$O(C=S)NR^2R^3$ (wherein $R^1$, $R^2$, and $R^3$ have the same definitions as described in relation to X and Y, each of A and Q represents an oxygen atom or a sulfur atom, p is 0, 1, or 2, n is 1 or 2), —OM (wherein M represents a hydrogen atom, an alkali metal, an alkaline earth metal, or an organic base), or a halogen atom; and m is an integer between 0 and 4 inclusive.

(8) A triketone derivative according to (7), wherein Y represents a hydrogen atom or a methyl group.
(9) A triketone derivative according to (7), wherein Y represents a hydrogen atom.
(10) A triketone derivative according to any one of (7) to (9), wherein Z represents a halogen atom, —$OR^1$, —$SO_pR^1$, —$A(CH_2)_nQR^1$, or —$N(OR^1)R^2$.
(11) A triketone derivative according to any one of (1) to (10), wherein X represents a halogen atom or a methyl group.
(12) A herbicide containing a triketone derivative as recited in any one of (1) to (11) as an active ingredient.
(13) A herbicide for use in cultivation of a paddy rice plant, which herbicide contains a triketone derivative as recited in any one of (1) to (11) as an active ingredient.

BEST MODE OF CARRYING OUT THE INVENTION

Hereafter, various modes for carrying out the present invention will be described.

I. The first Aspect of the Invention

The triketone derivative of the first aspect of the present invention (may be simply referred to as "the present invention" throughout section I) is represented by chemical formula [I-1]. Of these, triketone derivatives represented by formulas [I-2] and [I-3] are preferred in that they provide a low level of chemical injury to cultivated plants and have an excellent weed-controlling effect.

When each of $R^1$ to $R^3$ in formulas [I-1] to [I-4] represents a C1–C6 alkyl group which may have a branched structure, a cyclic structure, or an unsaturated bond, examples of the alkyl group include a methyl group, an ethyl group, an n-propyl group, an i-propyl group, an n-butyl group, an i-butyl group, a sec-butyl group, a tert-butyl group, an n-pentyl group, an i-pentyl group, a sec-pentyl group, an n-hexyl group, and an i-hexyl group. The ethyl group, propyl groups, and butyl groups may have an unsaturated bond, and the propyl groups, butyl groups, pentyl groups, and hexyl groups may be linear, branched, or cyclic. Of these, a methyl group and an ethyl group are preferred.

When each of $R^1$ to $R^3$ in formulas (I-1] to [I-4] represents a C1–C6 haloalkyl group which may have a branched structure, a cyclic structure, or an unsaturated bond, examples of the haloalkyl group include the above-described alkyl groups in which some or all of the hydrogen atoms are substituted by a halogen atom such as a chlorine atom, a fluorine atom, a bromine atom, or an iodine atom. Specific examples include a chloromethyl group, a difluoromethyl group, a trichloromethyl group, a trifluoromethyl group, a 2-chloroethyl group, a 2-fluoroethyl group, a 3-chloropropyl group, and a 3-fluoropropyl group. Of these, a trifluoromethyl group and a trichloromethyl group are preferred.

When each of $R^1$ to $R^3$ in formulas [I-1] to [I-4] represents a phenyl group which may be substituted, examples of the phenyl group include a phenyl group, a tolyl group, an m-chlorophenyl group, a p-methoxyphenyl group, a p-nitrophenyl group, and p-cyanophenyl group. When each of $R^1$ to $R^3$ represents a benzyl group which may be substituted, examples of the benzyl group include a benzyl group, an α-methylbenzyl group, an o-methylbenzyl group, an m-chlorobenzyl group, a p-methoxybenzyl group, a p-nitrobenzyl group, and a p-cyanobenzyl group.

When each of X and Y in formulas [I-1] to [I-4] or Z in formula [I-4] represents an —$OR^1$, examples of the alkoxy group include a methoxy group, an ethoxy group, an n-propoxy group, an i-propoxy group, an n-butoxy group, an i-butoxy group, a sec-butoxy group, a tert-butoxy group, an n-pentyloxy group, an i-pentyloxy group, a sec-pentyloxy group, an n-hexyloxy group, and an i-hexyloxy group. The propoxy groups and butoxy groups may have an unsaturated bond and may be linear, branched, or cyclic. In the above-described alkoxy groups, some or all of the hydrogen atoms may be substituted by a halogen atom. Examples of such haloalkoxy groups include a chloromethyloxy group, a difluoromethyloxy group, a trichloromethyloxy group, a trifluoromethyloxy group, a 2-chloroethyloxy group, a 2-fluoroethyloxy group, a 3-chloropropyloxy group, and a 3-fluoropropyloxy group. Of these, a methoxy group, an ethoxy group, a difluoromethyloxy group, and a trifluoromethyloxy group are preferred.

When each of X and Y in formulas [I-1] to [I-4] represents an —$SR^1$ group, examples of the alkylthio group include a methylthio group, an ethylthio group, an n-propylthio group, an i-propylthio group, an n-butylthio group, an i-butylthio group, a sec-butylthio group, a tert-butylthio group, an n-pentylthio group, an i-pentylthio group, an n-hexylthio group, and an i-hexylthio group. The propylthio groups and butylthio groups may have an unsaturated bond and may be linear, branched, or cyclic. In the above-described alkylthio groups, some or all of the hydrogen atoms may be substituted by a halogen atom. Examples of such haloalkylthio groups include a chloromethylthio group, a difluoromethylthio group, a trichloromethylthio group, a trifluoromethylthio group, a 2-chloroethylthio group, a 2-fluoroethylthio group, a 3-chloropropylthio group, and a 3-fluoropropylthio group. Of these, a methylthio group, an ethylthio group, and a trifluoromethylthio group are preferred.

Examples of the —$SO_2R^1$ group include a methylsulfonyl group, an ethylsulfonyl group, an n-propylsulfonyl group, an i-propylsulfonyl group, an n-butylsulfonyl group, an i-butylsulfonyl group, a sec-butylsulfonyl group, and a tert-butylsulfonyl group. Of these, a methylsulfonyl group and an ethylsulfonyl group are preferred.

When each of X, Y, and Z in formulas [I-1] to [I-4] represents an —$NR^2R^3$ group, examples thereof include a methylamino group, a dimethylamino group, an ethylamino group, a pyrrolidinyl group, and a piperidino group. Examples of the —$N(OR^1)R^2$ group include a methoxyamino group, a methoxymethylamino group, a benzyloxyamino group, and an allyloxyamino group.

Example of the —$NHCOR^1$ include —$NHCOCH_3$, —$NHCOC_2H_5$, —$NHCOC_3H_7$, and —$NHCOC_4H_{10}$.

$R^4$ in formulas [I-1] and [1-3] represents a hydrogen atom or a C1–C6 alkyl group. Examples of the C1–C6 alkyl group include a methyl group, an ethyl group, an n-propyl group, an i-propyl group, an n-butyl group, an i-butyl group, a sec-butyl group, a tert-butyl group, an n-pentyl group, an i-pentyl group, a sec-pentyl group, an n-hexyl group, and an i-hexyl group. Of these, a hydrogen atom and a methyl group are preferred, with a hydrogen atom being particularly preferred.

Examples of preferable X in formulas [I-1] to [I-4] include a halogen atom, —$R^1$, —$OR^1$, and —$SR^1$, with a halogen atom and a methyl group being particularly preferred. Examples of preferable Y in formulas [I-1] to [I-4] include a hydrogen atom, a halogen atom, and —$R^1$, with a hydrogen atom, a methyl group, and a fluorine atom being particularly preferred.

The number "m" in formulas [I-1] to [I-4] is 0–4, preferably 0–2, particularly preferably 0.

When Z in formula [I-4] represents an —$SOPR^1$ group, examples thereof include alkylsulfonyl groups such as a methylsulfonyl group, an ethylsulfonyl group, a propylsulfonyl group, a butylsulfonyl group, a pentylsulfonyl group, and a hexylsulfonyl group; alkylsulfinyl groups such as a methylsulfinyl group, an ethylsulfinyl group, a propylsulfinyl group, a butylsulfinyl group, a pentylsulfinyl group, and a hexylsulfinyl group; and alkylthio groups such as a methylthio group, an ethylthio group, a propylthio group, a butylthio group, a pentylthio group, and a hexylthio group.

Examples of M contained in the —OM group in formulas [I-1] to [I-3] and in formula [I-4] when Z represents an —OM group include a hydrogen atom; alkali metal atoms such as lithium, sodium, and potassium; alkaline earth metal atoms such as magnesium, calcium, and barium; organic bases such as trimethylamine, triethylamine, and aniline. Of these, a hydrogen atom is particularly preferred as M.

When Z in a triketone derivative represented by formula [I-4] is a hydroxy group, the derivative may be tautomers having the following structures:

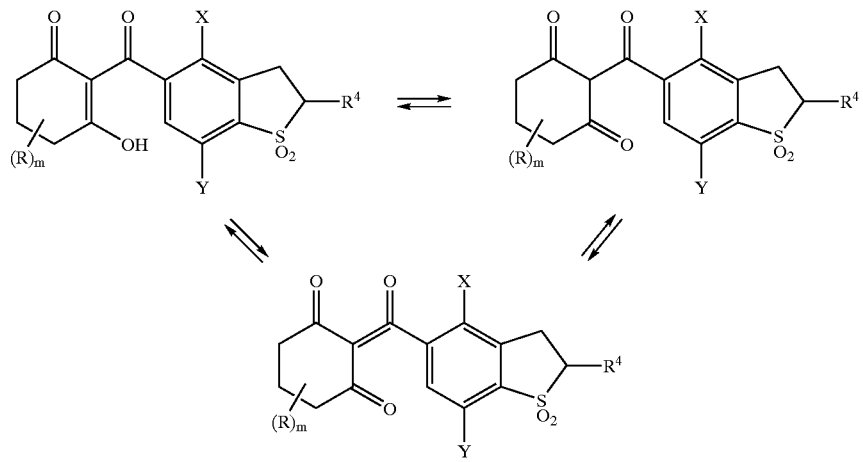

wherein R, R⁴, X, Y, and m have the same definitions as described in relation to formula [I-4]. The triketone derivative of the present invention encompasses all these tautomeric compounds and mixtures thereof.

A process for producing the triketone derivative of the present invention will next be described. First of all, an intermediate for producing the triketone derivative of the present invention; i.e., benzothiophene-2-carboxylic acid, is produced. For example, the intermediate can be effectively produced through the following steps.

(1) First Step

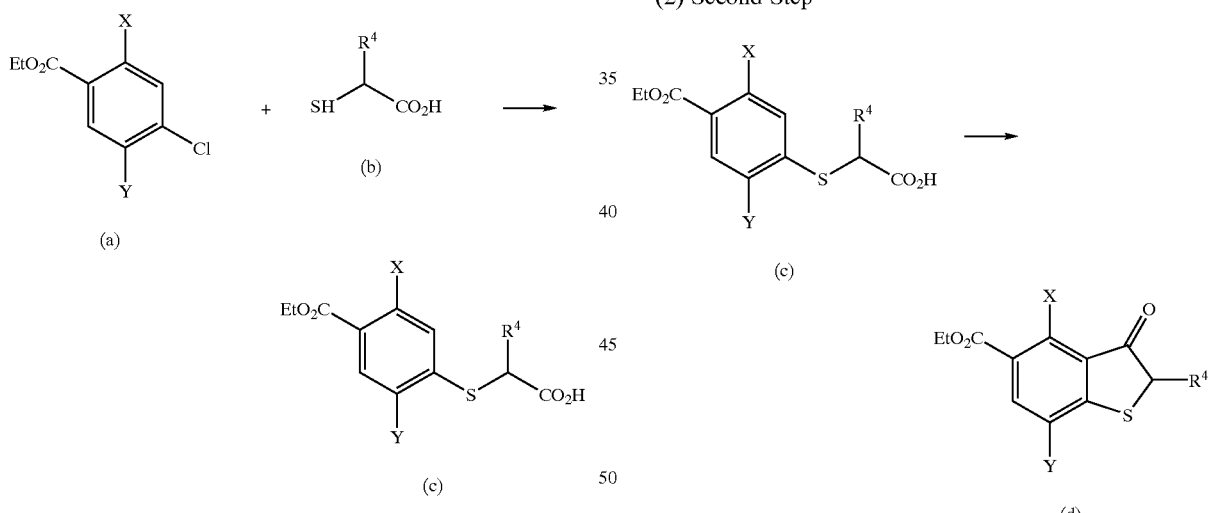

In the first step, Compounds (a) and (b) are used in an amount of 1 mol each to carry out the above reaction in the presence of 1 mol or more of a base to thereby obtain Compound (c). Either of Compound (a) or Compound (b) may be used in an amount in excess of equimol with respect to the other.

Examples of the base which can be used in the reaction include an alkali metal carbonate, an alkaline earth metal carbonate, and an alkali metal hydroxide. Examples of a solvent which is inert to the reaction and used in the reaction include alcohols such as methanol and ethanol; halohydrocarbons such as chloroform and dichloromethane; hydrocarbons such as hexane and toluene; N,N-dimethylformamide; and water. The reaction is carried out in the temperature range of 0° C. to the boiling point of the employed solvent, with stirring until completion of the reaction.

Alternatively, the reaction may be carried out in a two-phase system in the presence of a quaternary ammonium salt. Furthermore, Compound (a) may be reacted with sodium hydrogensulfide or potassium hydrogensulfide, and chloroacetic acid or bromoacetic acid, to thereby obtain Compound (c).

When the substituent X or Y in Compound (c) is a leaving group, the product may be obtained as a mixture. In this case, the product is purified through a process such as distillation, recrystallization, or chromatographic purification, to thereby yield the target compound.

(2) Second Step

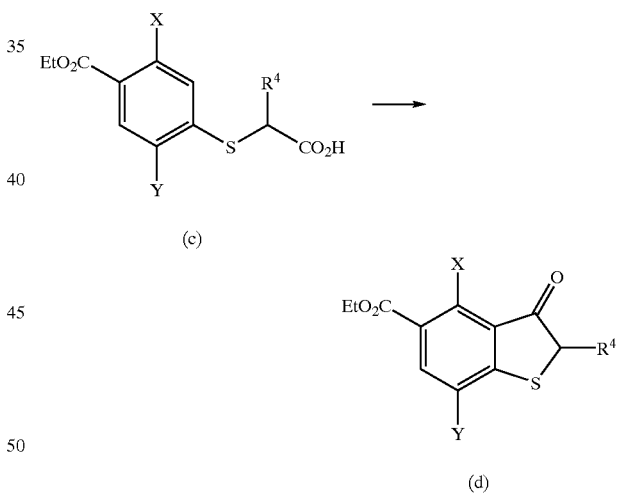

In the second step, Compound (c) is cyclized to form Compound (d) as shown in the above reaction. The cyclization is carried out in the presence of an acidic reagent in a catalyst amount or in an amount of equimol or more. Examples of preferred acidic reagents include hydrochloric acid, sulfuric acid, phosphorus trichloride, phosphorus pentachloride, phosphorus oxychloride, polyphosphoric acid, acetic acid, acetic anhydride, trifluoromethanesulfonic acid, trifluoromethanesulfonic anhydride, and sulfuryl chloride. The reaction may be carried out in the absence of a solvent. When a solvent is employed, examples of preferred solvents include hexane, dichloromethane, 1,2-dichloroethane, chloroform, and N,N-dimethylformamide.

The reaction is carried out in the temperature range of −20° C. to the boiling point of the employed solvent, with stirring until completion of the reaction.

Alternatively, Compound (c) is transformed into its acid halide, and the acid halide is reacted in the presence of a Lewis acid. In this case, the transformation is carried out by use of a halogenating agent such as oxalyl chloride or thionyl chloride in an amount of equimol or more in the absence of a solvent or in the presence of a solvent such as methylene chloride, 1,2-dichloroethane, or chloroform. The reaction is carried out in the temperature range of room temperature to the boiling point of the employed solvent, with stirring until completion of the reaction. The subsequent reaction is carried out by use of a Lewis acid such as aluminum chloride, titanium tetrachloride, or tin tetrachloride. The reaction is carried out in the temperature range of −20° C. to the boiling point of the employed solvent, with stirring until completion of the reaction. When Y of Compound (d) is a hydrogen atom, the other isomer may be intermingled with the product as an impurity. In such a case, the product is purified through a method as described above.

(3) Third Step

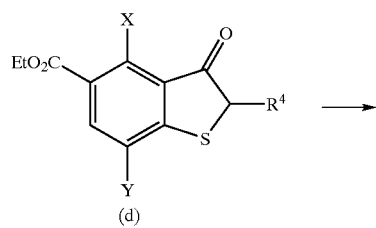

(d)

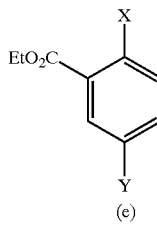

(e)

In the third step, Compound (d) is reduced to form Compound (e) as shown in the above reaction. Examples of preferred reducing agents used in the reduction include sodium borohydride and aluminum triisopropoxide. Examples of preferred solvents include methanol, ethanol, water, dichloromethane, and toluene. The reduction is carried out in the temperature range of −20° C. to the boiling point of an employed solvent, with stirring until completion of the reaction.

(4) Fourth Step

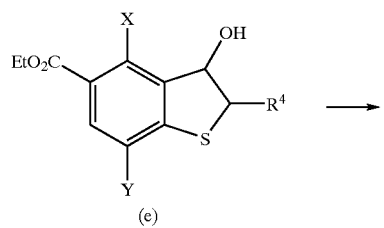

(e)

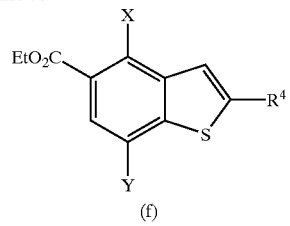

(f)

In the fourth step, Compound (e) is dehydrated to form Compound (f) as shown in the above reaction. The dehydration may be carried out in the presence of a catalyst amount of an acidic substance such as hydrochloric acid, sulfuric acid, p-toluenesulfonic acid, or Amberlist. In this case, a solvent such as benzene or toluene is preferred as a reaction solvent, in that water formed during dehydration can be removed through azeotropic distillation. The formed water is adsorbed in an adsorbent such as a molecular sieve, or is removed through azeotropic distillation with the solvent, to thereby accelerate dehydration. When such an adsorbent is used, the dehydration is carried out in the temperature range of room temperature to 50° C. with stirring until completion of the reaction. Azeotropic distillation is carried out through refluxing with heat at the boiling point of the employed solvent until the theoretical amount of water is removed.

(5) Fifth Step

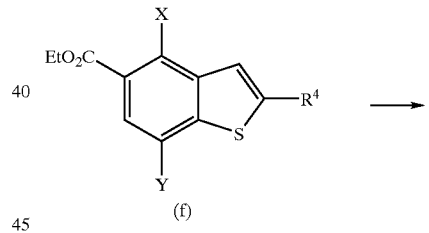

(f)

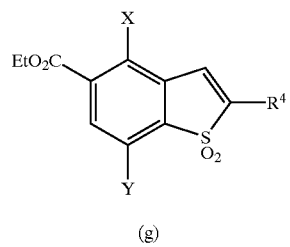

(g)

In the fifth step, Compound (f) is oxidized to form Compound (g) as shown in the above reaction. The oxidation is carried out in the presence of an organic peroxide such as hydrogen peroxide or m-chloroperbenzoic acid in an amount of 2 mol or more. In this case, a solvent such as acetic acid or methylene chloride is preferred as a reaction solvent. The oxidation is carried out in the temperature range of −20° C. to 100° C., with stirring until completion of the reaction.

(6) Sixth Step

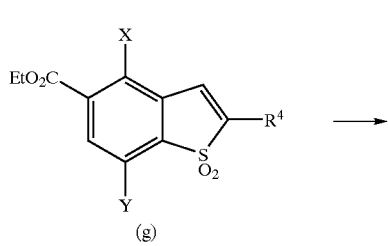

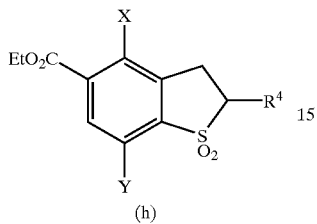

In the sixth step, Compound (g) is hydrogenated to form Compound (h) as shown in the above reaction. The hydrogenation is carried out under similar conditions as employed for customary catalytic hydrogenation. Examples of preferred catalysts include palladium-on-active carbon, Raney nickel, and platinum oxide. In this case, a solvent such as tetrahydrofuran, methanol, ethanol, ethyl acetate, or water is preferred as a reaction solvent. The hydrogenation is carried out in a hydrogen gas atmosphere, with or without pressure, and in the temperature range of room temperature to the boiling point of the employed solvent, with stirring until completion of the reaction.

(7) Seventh Step

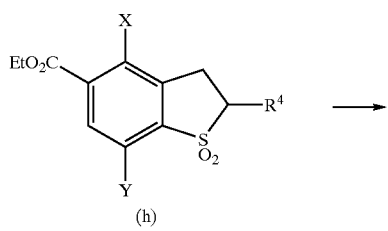

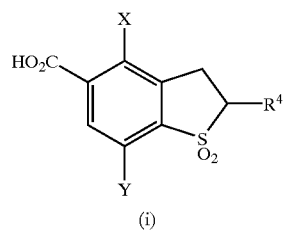

In the seventh step, Compound (h) is hydrolyzed to form Compound (i) as shown in the above reaction. The hydrogenation is carried out in the presence of an alkali metal hydroxide in an amount of equimol or more in a mixture of water and alcohol such as ethanol as a solvent. The hydrolysis is carried out in the temperature range of room temperature to the boiling point of the employed solvent, with stirring until completion of the reaction.

The thus-obtained intermediate, benzothiophene-2-carboxylic acid, is used in the following reaction:

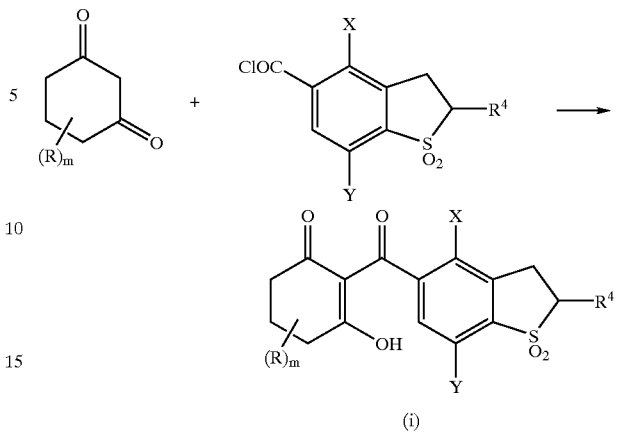

wherein R, $R^4$, X, Y, and m have the same definitions as described in relation to formula [I-1] to [I-4], to thereby produce triketone derivatives as represented by formula [I-1] to [I-3] and a triketone derivative as represented by formula [I-4] wherein Z represents a hydroxy group.

The intermediate, benzothiophene-2-carboxylic acid, is transformed into an acid halide thereof as described in relation to the above-described cyclization. The thus-formed acid halide is reacted with a diketone in the presence of an organic base such as triethylamine at 0–20° C. in an inert organic reaction solvent such as acetonitrile, and the reaction mixture is allowed to react with stirring at room temperature in the presence of a catalyst amount of a cyanide-donor such as acetone cyanohydrin.

Furthermore, the thus-obtained triketone derivatives represented by formula [I-1] to [I-3] and triketone derivative represented by formula [I-4] wherein Z represents a hydroxy group are reacted with a compound which can substitute some or all of the hydroxy groups in accordance with reaction, e.g., reaction as described in Japanese Patent Application Laid-Open (kokai) Nos. 62-298563, 62-242755, or 63-2947, to thereby produce substituted triketone derivatives represented by formula [I-1] to [I-3] and triketone derivative represented by formula [I-4] wherein Z represents a variety of substituents.

II. The Second Aspect of the Invention

The triketone derivative of the second aspect of the present invention (may be simply referred to as "the present invention" throughout section II) is represented by chemical formula [II-1]. Of these, triketone derivatives represented by formulas [II-2] and [II-3] are preferred. Furthermore, among the triketone derivatives represented by formulas [II-2] and [II-3], triketone derivatives represented by formulas [II-4] to [II-9] are more preferred in that they provide a low level of chemical injury to cultivated plants and have an excellent weed-controlling effect.

In the triketone derivatives represented by formulas [II-1] to [II-9], the substituent represented by X is preferably a halogen atom, an alkyl group represented by $—R^1$, an alkoxy group represented by $—OR^1$, or an alkylthio group represented by $—SR^1$. In the triketone derivative represented by formula [II-10], the substituent Y represents a hydrogen atom or a variety of groups. Of these, a hydrogen atom and a methyl group are preferred. In the triketone derivative represented by formula [II-10], the substituent X represents a variety of groups. Of these, a halogen atom and a methyl group are preferred.

In the triketone derivative represented by formulas [II-1] to [II-10], each of the substituents Z and $Z^1$ represents a variety of groups. Of these, a halogen atom, and —$OR^1$, —$SO_pR^1$, —$A(CH_2)_{OR}{}^1$, —$NR^2R^3{}_1$ and —$N(OR^1)R^2$ described below are preferred.

When each of $R^1$ to $R^3$ in formulas [II-1] to [II-9] represents a C1–C6 alkyl group which may have a branched structure, a cyclic structure, or an unsaturated bond, examples of the alkyl group include a methyl group, an ethyl group, an n-propyl group, an i-propyl group, an n-butyl group, an i-butyl group, a sec-butyl group, a tert-butyl group, an n-pentyl group, an i-pentyl group, a sec-pentyl group, an n-hexyl group, and an i-hexyl group. The ethyl group, propyl groups, and butyl groups may have an unsaturated bond, and the propyl groups, butyl groups, pentyl groups, and hexyl groups may be linear, branched, or cyclic. Of these, a methyl group and an ethyl group are preferred.

When each of $R^1$ to $R^3$ represents a C1–C6 haloalkyl group which may have a branched structure, a cyclic structure, or an unsaturated bond, examples of the haloalkyl group include the above-described alkyl groups in which some or all of the hydrogen atoms are substituted by a halogen atom such as a chlorine atom, a fluorine atom, a bromine atom, or an iodine atom. Specific examples include a chloromethyl group, a difluoromethyl group, a trichloromethyl group, a trifluoromethyl group, a 2-chloroethyl group, a 2-fluoroethyl group, a 3-chloropropyl group, and a 3-fluoropropyl group. Of these, a trifluoromethyl group is preferred.

When each of $R^1$ to $R^3$ represents a phenyl group which may be substituted, examples of the phenyl group include a phenyl group, a tolyl group, an m-chlorophenyl group, a p-methoxyphenyl group, a p-nitrophenyl group, and p-cyanophenyl group. When each of $R^1$ to $R^3$ represents a benzyl group which may be substituted, examples of the benzyl group include a benzyl group, an α-methylbenzyl group, an o-methylbenzyl group, an m-chlorobenzyl group, a p-methoxybenzyl group, a p-nitrobenzyl group, and a p-cyanobenzyl group. Of these, a phenyl group and a benzyl group are preferred. When each of X, Y, and $Z^1$ in formulas [II-1] to [II-9] represents an —$OR^1$ group, examples of the alkoxy group include a methoxy group, an ethoxy group, propoxy groups, butoxy groups, pentyloxy groups, and hexyloxy groups. The propoxy groups and butoxy groups may have an unsaturated bond and may be linear, branched, or cyclic. In the above-described alkoxy groups, some or all of the hydrogen atoms may be substituted by a halogen atom. Examples of such haloalkoxy groups include a chloromethyloxy group, a difluoromethyloxy group, a trichloromethyloxy group, a trifluoromethyloxy group, a 2-chloroethyloxy group, a 2-fluoroethyloxy group, a 3-chloropropyloxy group, and a 3-fluoropropyloxy group. Of these, a methoxy group, an ethoxy group, and an isopropoxy group are preferred.

When each of X, Y, and $Z^1$ in formulas [II-1] to [II-9] represents an —$SR^1$ group, examples of the alkylthio group include a methylthio group, an ethylthio group, propylthio groups, butylthio groups, pentylthio groups, and hexylthio groups. The propylthio groups and butylthio groups may have an unsaturated bond and may be linear, branched, or cyclic. In the above-described alkylthio groups, some or all of the hydrogen atoms may be substituted by a halogen atom. Examples of such haloalkylthio groups include a chloromethylthio group, a difluoromethylthio group, a trichloromethylthio group, a trifluoromethylthio group, a 2-chloroethylthio group, a 2-fluoroethylthio group, a 3-chloropropylthio group, and a 3-fluoropropylthio group.

Of these, a methylthio group, an ethylthio group, an i-propylthio group, and a t-butylthio group are preferred.

When each of X, Y, and $Z^1$ in formulas [II-1] to [II-9] represents an —$SO_pR^1$ group, examples of the —$SO_pR^1$ group include alkylsulfonyl groups such as a methylsulfonyl group, an ethylsulfonyl group, propylsulfonyl groups, butylsulfonyl groups, pentylsulfonyl groups, and hexylsulfonyl groups; alkylsulfinyl groups such as a methylsulfinyl group, an ethylsulfinyl group, propylsulfinyl groups, butylsulfinyl groups, pentylsulfinyl groups, and hexylsulfinyl groups; and alkylthio groups such as a methylthio group, an ethylthio group, propylthio groups, butylthio groups, pentylthio groups, and hexylthio groups. Of these, a methylsulfonyl group and an ethylsulfonyl group are preferred. In addition, when each of X, Y, and $Z^1$ in the formulas represents an —$NR^2R^3$ group, examples thereof include a methylamino group, a dimethylamino group, an ethylamino group, a pyrrolidinyl group, and a piperidino group. When each of X, Y, and $Z^1$ in the formulas represents an —$N(OR^1)R^2$ group, examples of the —$N(OR^1)R^2$ group include a methoxyamino group, a methoxymethylamino group, a benzyloxyamino group, and an allyloxyamino group. Of these, a methoxymethylamino group is preferred.

The number "q," the number of the substituent X, is 1 or 2, with 1 being preferred.

When Z in formula [II-10] represents an —$O(C=O)R^1$ group, examples include an acetoxy group and a propionyloxy group.

When each of Z and $Z^1$ in formulas [II-1] to [II-10] represents an —$O(C=O)OR^1$ group, examples of the —$O(C=O)OR^1$ group include a methoxycarbonyloxy group, an ethoxycarbonyloxy group, and a propoxycarbonyloxy group. When each of Z and $Z^1$ in formulas [II-1] to [II-10] represents an —$O(C=O)SR^1$ group, examples of the —$O(C=O)SR^1$ group include a methylthiocarbonyloxy group, an ethylthiocarbonyloxy group, and a propylthiocarbonyloxy group. When each of Z and $Z^1$ in formulas [II-1] to [II-10] represents an —$O(C=O)NR^1R^2$ group, examples of the —$O(C=O)NR^1R^2$ group include an N-methylcarbamoyl group, an N-ethylcarbamoyl group, and an N-dimethylcarbamoyl group. When each of Z and $Z^1$ in formulas [II-1] to [II-10] represents an —$O(C=S)NR^1R^2$ group, examples of the —$O(C=S)NR^1R^2$ group include an N-methylthiocarbamoyl group, an N-ethylthiocarbamoyl group, and an N-dimethylthiocarbamoyl group.

In these formulas, m is preferably 0–2, with 0 being particularly preferred.

The triketone derivative represented by formula [II-1] may be tautomers having the following structures:

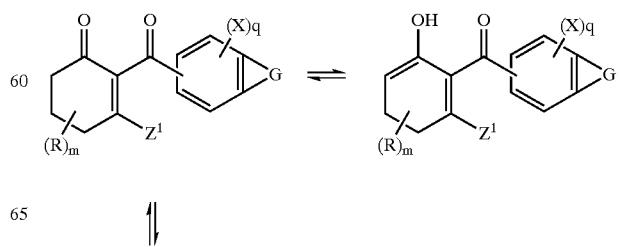

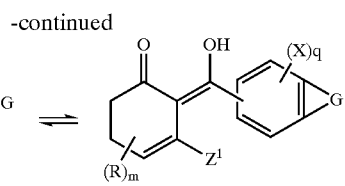

wherein R, X, G, $Z^1$, m and q have the same definitions as described in relation to formula [II-1]. The triketone derivative of the present invention encompasses all these tautomeric compounds and mixtures thereof.

Furthermore, examples of the optionally substituted ring-constituting atoms represented by $G^1$ to $G^4$ in formulas [II-4] to [II-9], which are described as preferable examples of G, include an unsubstituted ring-constituting atom and a ring-constituting atom which has one or two substituents selected from the group consisting of a methyl group, an oxo group, a methoxy group, an isopropyloxy group, and a methoxyimino group. In the above formulas, i is preferably 2.

The process for producing the triketone derivative of the present invention will next be described. First of all, when G in formula [II-11] forms a 5-membered ring including two carbon atoms of the benzene ring adjacent to G, an intermediate for producing the triketone derivative of the present invention, i.e., benzothiophene-2-carboxylic acid, is produced. For example, the intermediate can be effectively produced through the following steps.

(1) First Step

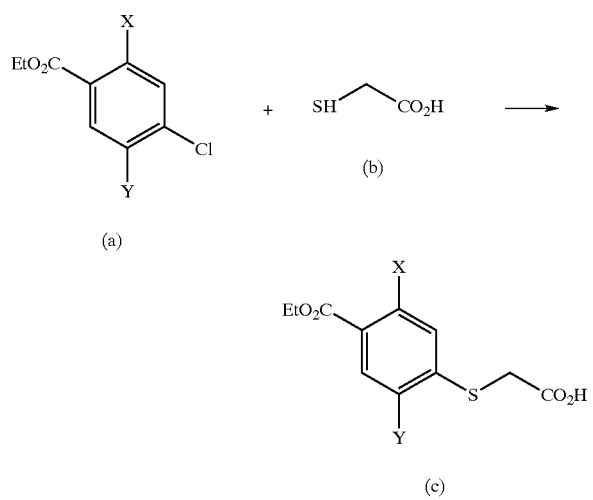

In the first step, Compounds (a) and (b) are used in an amount of 1 mol each to carry out the above reaction in the presence of 1 mol or more of a base to thereby obtain Compound (c). Either of Compound (a) or Compound (b) may be used in an amount in excess of equimol with respect to the other.

Examples of the base which can be used in the reaction include an alkali metal carbonate, an alkaline earth metal carbonate, and an alkali metal hydroxide. Examples of a solvent which is inert to the reaction and used in the reaction include alcohols such as methanol and ethanol; halohydrocarbons such as chloroform and dichloromethane; hydrocarbons such as hexane and toluene; and water. The reaction is carried out in the temperature range of 0° C. to the boiling point of the employed solvent, with stirring until completion of reaction.

Alternatively, the reaction may be carried out in a two-phase system in the presence of a quaternary ammonium salt. Furthermore, Compound (a) may be reacted with sodium hydrogensulfide or potassium hydrogensulfide and chloroacetic acid or bromoacetic acid, to thereby obtain Compound (c).

When the substituent X or Y in Compound (c) is a leaving group, the product may be obtained as a mixture. In this case, the product is purified through a process such as distillation, recrystallization, or chromatographic purification, to thereby yield the target compound.

(2) Second Step

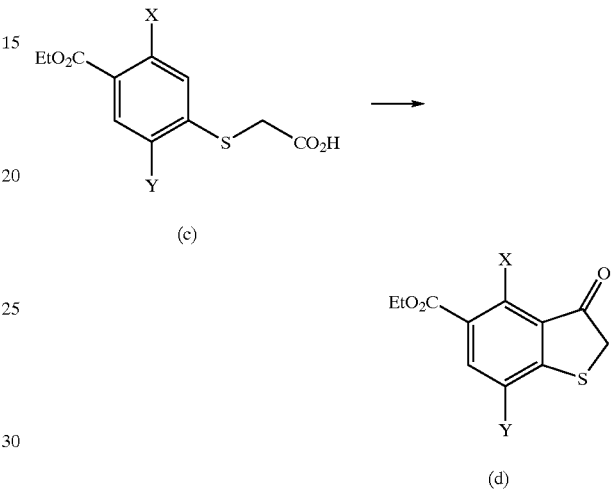

In the second step, Compound (c) is cyclized to form Compound (d) as shown in the above reaction. The cyclization is carried out in the presence of an acidic reagent in a catalyst amount or in an amount of equimol or more. Examples of preferred acidic reagents include hydrochloric acid, sulfuric acid, phosphorus trichloride, phosphorus pentachloride, phosphorus oxychloride, polyphosphoric acid, acetic acid, acetic anhydride, trifluoromethanesulfonic acid, trifluoromethanesulfonic anhydride, and sulfuryl chloride. The reaction may be carried out in the absence of a solvent. When a solvent is used, examples of preferred solvents include hexane, dichloromethane, 1,2-dichloroethane chloroform, and N,N-dimethylformamide. The reaction is carried out in the temperature range of –20° C. to the boiling point of the employed solvent, with stirring until completion of the reaction.

Alternatively, Compound (c) is transformed into its acid chloride, and the acid chloride is reacted in the presence of a Lewis acid. In this case, the transformation is carried out by use of a halogenating agent such as oxalyl chloride or thionyl chloride in an amount of equimol or more in the absence of a solvent or in the presence of a solvent such as methylene chloride, 1,2-dichloroethane, or chloroform. The reaction is carried out in the temperature range of room temperature to the boiling point of the employed solvent, with stirring until completion of the reaction. The subsequent reaction is carried out by use of a Lewis acid such as aluminum chloride, titanium tetrachloride, or tin tetrachloride. The reaction is carried out in the temperature range of –20° C. to the boiling point of the employed solvent, with stirring until completion of the reaction. When Y of Compound (d) is a hydrogen atom, the other isomer may be intermingled with the product as an impurity. In such a case, the product is purified through a method as described above.

(3) Third Step

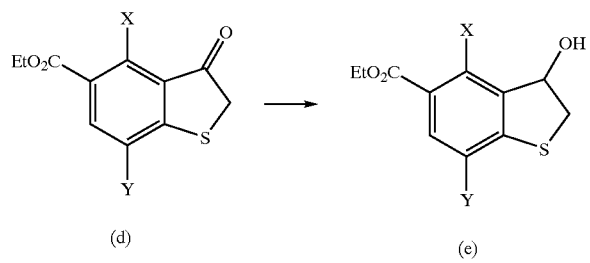

In the third step, Compound (d) is reduced to form Compound (e) as shown in the above reaction. Examples of preferred reducing agents used in the reduction include sodium borohydride and aluminum triisopropoxide. Examples of preferred solvents include methanol, ethanol, water, dichloromethane, and toluene. The reduction is carried out in the temperature range of −20° C. to the boiling point of the employed solvent with stirring until completion of the reaction.

(4) Fourth Step

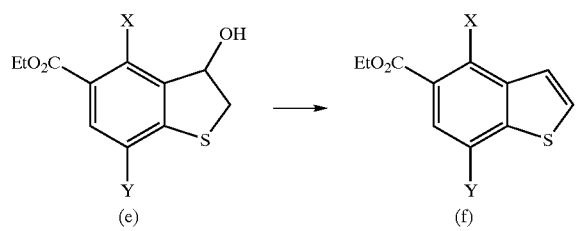

In the fourth step, Compound (e) is dehydrated to form Compound (f) as shown in the above reaction. The dehydration may be carried out in the presence of a catalyst amount of an acidic substance such as hydrochloric acid, sulfuric acid, or p-toluenesulfonic acid. In this case, a solvent such as benzene or toluene is preferred as a reaction solvent, in that water formed during dehydration can be removed through azeotropic distillation. The formed water is adsorbed in an adsorbent such as a molecular sieve, or is removed through azeotropic distillation with the solvent, to thereby accelerate dehydration. When such an adsorbent is used, the dehydration is carried out in the temperature range of room temperature to 50° C., with stirring until completion of the reaction. Azeotropic distillation is carried out through refluxing with heat at the boiling point of the employed solvent by the time a theoretical amount of water is removed.

(5) Fifth Step

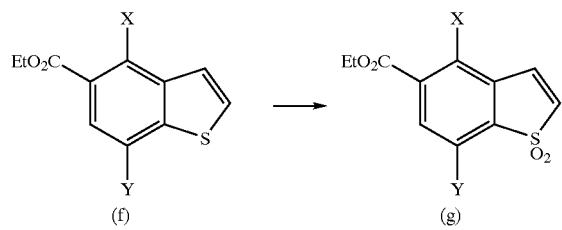

In the fifth step, Compound (f) is oxidized to form Compound (g) as shown in the above reaction. The oxidation is carried out in the presence of an organic peroxide such as hydrogen peroxide or m-chloroperbenzoic acid in an amount of 2 mol or more. In this case, a solvent such as acetic acid or methylene chloride is preferred as a reaction solvent. The oxidation is carried out in the temperature range of −20° C. to 100° C., with stirring until completion of the reaction.

(6) Sixth Step

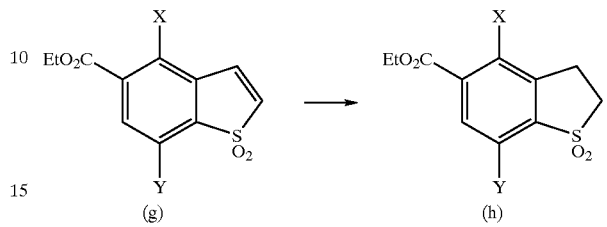

In the sixth step, Compound (g) is hydrogenated to form Compound (h) as shown in the above reaction. The hydrogenation is carried out under similar conditions as employed for customary catalytic hydrogenation. Examples of preferred catalysts include palladium-on-active carbon, Raney nickel, and platinum oxide. In this case, a solvent such as tetrahydrofuran, methanol, ethanol, ethyl acetate, or water is preferred as a reaction solvent. The hydrogenation is carried out in a hydrogen gas atmosphere, with or without pressure, and in the temperature range of room temperature to the boiling point of the employed solvent, with stirring until completion of the reaction.

(7) Seventh Step

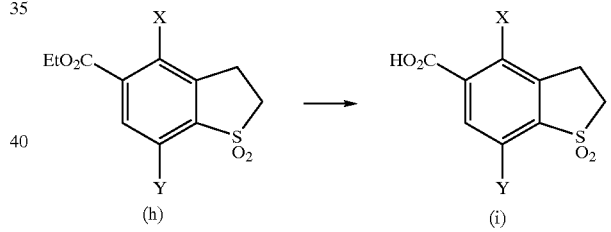

In the seventh step, Compound (h) is hydrolyzed to form Compound (i) as shown in the above reaction. The hydrogenation is carried out in the presence of an alkali metal hydroxide in an amount of equimol or more in a mixture of water and alcohol such as ethanol as a solvent. The hydrolysis is carried out in the temperature range of room temperature to the boiling point of the employed solvent, with stirring until completion of the reaction.

The thus-obtained intermediate is used in the following reaction:

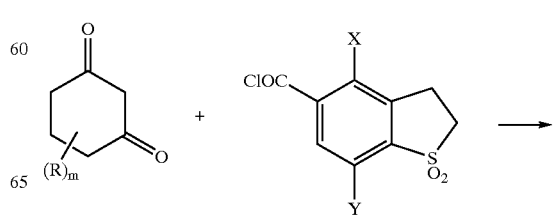

-continued

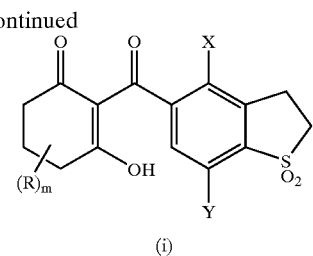

(i)

wherein R, X, Y, and m have the same definitions as described in relation to the above-described formulas, to thereby produce triketone derivatives as represented by the above-described formulas wherein Z represents a hydroxy group.

The intermediate carboxylic acid is transformed into an acid halide thereof as described in relation to the above-described cyclization. The thus-formed acid halide is reacted with a diketone in the presence of an organic base such as triethylamine at 0–20° C. in an inert organic reaction solvent such as acetonitrile, and the reaction mixture is allowed to react with stirring at room temperature in the presence of a catalyst amount of a cyanide-donor such as acetone cyanohydrin.

When G in the above formulas forms a 6- or 7-membered ring including two carbon atoms of the benzene ring adjacent to G, an intermediate for producing the triketone derivative can be produced through a method described in WO94/04524, WO94/08988, or WO97/03064.

Furthermore, either one of the thus-obtained triketone derivatives represented by the above formulas wherein Z represents a hydroxy group is reacted with a compound which can substitute some or all of the hydroxy groups in accordance with a reaction described, for example, in Japanese Patent Application Laid-Open (kokai) Nos. 62-298563, 62-242755, or 63-2947, to thereby produce substituted triketone derivatives represented by the above formulas wherein Z represents a variety of substituents.

III. Herbicides

The herbicides of the first and second aspects of the present invention (may be simply referred to as "the present invention" throughout section III) contain, as an active ingredient, triketone derivatives represented by formulas [I-1] to [I-4] in the first aspect or represented by formulas as described above in the second aspect. The herbicides are produced through mixing the triketone derivative with a liquid carrier such as a solvent or a solid carrier such as a mineral powder, and are prepared into a variety of forms such as water-dispersible powder, emulsion, powder, and granules for use. During preparation of the herbicide, a surfactant is preferably added to the herbicide so as to impart properties such as an emulsifying property, dispersibility, and extendability to the herbicide.

When the herbicide of the present invention is used in the form of water-dispersible powder, the triketone derivative, a solid carrier, and a surfactant are typically mixed, in amounts of 5–55 wt. %, 40–93 wt. %, and 2–5 wt.%, respectively, to thereby prepare a composition, which serves as a herbicide.

When the herbicide of the present invention is used in the form of emulsion, the triketone derivative, a solvent, and a surfactant are typically mixed in amounts of 10–50 wt. %, 35–85 wt. %, and 5–15 wt. %, respectively, to thereby prepare a composition, which serves as a herbicide.

When the herbicide of the present invention is used in the form of powder, the triketone derivative, a solid carrier, and a surfactant are typically mixed in amounts of 1–15 wt. %, 80–97 wt. %, and 2–5 wt. %, respectively, to thereby prepare a composition, which serves as a herbicide.

When the herbicide of the present invention is used in the form of granules, the triketone derivative, a solid carrier, and a surfactant are typically admixed in amounts of 1–15 wt. %, 80–97 wt. %, and 2–5 wt. %, respectively, to thereby prepare a composition, which serves as a herbicide.

Examples of preferred solid carriers include oxides such as diatomaceous earth and slaked lime; phosphates such as apatite; sulfates such as gypsum; and mineral micropowders such as talc, pyrophyllite, clay, kaolin, bentonite, acidic terra alba, white carbon, quartz powder, and silica stone powder.

Examples of preferred organic solvents include aromatic hydrocarbons such as benzene, toluene, and xylene; chlorohydrocarbons such as o-chlorotoluene, trichloroethane, and trichloroethylnene; alcohols such as cyclohexanol, amyl alcohol, and ethylene glycol; ketones such as isophorone, cyclohexanone, and cyclohexenyl-cyclohexanone; ethers such as butyl cellosolve, diethyl ether, and methyl ethyl ether; esters such as isopropyl acetate, benzyl acetate, and methyl phthalate; amides such as dimethylformamide; and mixtures thereof.

Examples of the surfactant which can be used in the invention include anionic, nonionic, cationic, and ampholytic surfactants such as amino acid-type and betaine-type surfactants.

To the herbicide of the present invention, an ingredient having a weed-controlling activity may optionally be added other than the triketone derivative represented by formulas [I-1) to [II-10). Examples of the compound contained in such an ingredient include diphenyl ether, triazine, urea, carbamate, thiocarbamate, acid anilide, pyrazole, phosphoric acid, sulfonylurea, and oxadiazone. These ingredients may appropriately be used in combination.

Furthermore, additives such as a pesticide, a bactericide, a plant-growth-regulator, and a fertilizer may optionally be incorporated into the herbicide of the present invention.

The herbicide of the present invention is applied directly to a weed or to a field where the weed grows, before or after germination of the weed. The manner of application depends on the type of a cultivated plant or the environment of use, and a form of application such as spraying, sprinkling, water sprinkling, or injecting may be employed.

Examples of the cultivated plant to which the herbicide is applied include graminaceous plants such as rice, wheat, barley, corn, oat, and sorghum; broad-leaved crops such as soybean, cotton, beet, sunflower, and rape; fruit trees; vegetables such as fruit, root, and leaf vegetables; and turf grass.

Examples of paddy weeds to which the herbicide of the present invention applies include Alismataceae such as *Alisma canaliculatum, Sagittaria trifolia*, and *Sagittaria pygmaea*; Cyperaceae such as *Cyperus difformis, Cyperus serotinus, Scirpus juncoides*, and *Eleocharis kuroguwai*; Scrothulariaceae such as *Lindernia pyxidaria*; Pontenderiaceae such as *Monochoria vaginalis*; Potamogetonaceae such as *Potamogeton distinctus*; Lythraceae such as *Rotala indica*; and Gramineae such as *Echinochloa crus-galli*.

Examples of field weeds include broad-leaved weeds, graminaceous weeds, and cyperaceous weeds. Specific examples of broad-leaved weeds include Solanaceae such as *Solanum nigrum* and *Datura stramonium*; Malvaceae such as *Abutilon theophrasti* and *Sida spinosa*; Convolulaceae such as *Ipomoea purpurea*; Amaranthaceae such as *Amaranthus lividus*; Compositae such as *Xanthium strumarium, Ambrosia artemisifolia, Galinsoga ciliata, Cirsium arvense, Senecio Vulgaris,* and *Erigeron annus*; Brassicaceae such as *Rorippa indica, Sinapis arvensis,* and *Capsella bursapastoris*; Polygonaceae such as *Polygonum bulumei* and *Polygonum convolvulus*; Portulacaceae such as *Portulaca oleracea*; Chenopodiaceae such as *Chenopodium alubum, Chenopodium ficiolium,* and *Kochia scoparia*; Caryophyllaceae such as *Stellaria media*; Scrophulariaceae such as *Veronica persica*; Commelinaceae such as *Commelina communis*; Euphorbiaceae such as *Lamium amplexicaule, Euphorbia supina,* and *Euphorbia maculata*; Rubiaceae such as *Galium spurium, Galium aparine,* and *Rubia akane*; Vilaceae such as *Viola arvensis*; and Leguminosae such as *Sesbania exaltata* and *Cassia obtusifolia*. Specific examples of Graminaceous weeds include *Sorghum bicolor, Panicum dichotomiflorum, Sorghum haepense, Echinochloa crusgalli, Digitaria adscendes, Avena fatua, Eleusine indica, Setaria viridis,* and *Alopecurus aequalis*. Specific examples of Cyperaceous weeds include *Cyperus rotundus* and *Cyperus esculentus*.

The present invention will next be described in more detail with reference to working examples and comparative examples.

EXAMPLE RELATED TO THE FIRST ASPECT OF THE INVENTION

Example I-1

[1] Synthesis of 4-chloro-5-oxycarbonyl-2,3-dihydrobenzothiophene-1,1-dioxide (1) Synthesis of ethyl 4-carboxymethylsulfenyl-2-chlorobenzoate A mixture containing ethyl 2,4-dichlorobenzoate (10.0 g), potassium carbonate (9.44 g), dimethylformamide (50 ml), and mercaptoacetic acid (3.8 ml) was allowed to react with heat at 80° C. for 4 hours.

Next, the resultant reaction mixture was poured into ice water and was subjected to extraction with ethyl acetate. The extract was dried over sodium sulfate and filtered, then concentrated to thereby obtain a crude reaction product (12.3 g).

(2) Synthesis of 4-chloro-5-ethoxycarbonyl-3-oxo-2,3-dihydrobenzothiophene

A mixture of ethyl 4-carboxymethylsulfenyl-2-chlorobenzoate (12.3 g) obtained in (1), 1,2-dichloroethane (36 ml), and thionyl chloride (3.9 ml) was refluxed with heat over 1 hour.

Acid chloride obtained by concentration of the reaction mixture was dissolved in dichloromethane (36 ml). Under cooling on ice, the solution was added dropwise over 1 hour to a solution of aluminum chloride (14.3 g, 107 mmol) and dichloromethane (150 ml) prepared in advance, after which reaction was continued for a further 2 hours at room temperature.

The thus-obtained reaction mixture was poured into ice water and subjected to extraction with dichloromethane. The extract was dried over sodium sulfate, filtered, and concentrated to thereby obtain a crude reaction product in the form of liver brown oil (12.3 g). Further, the crude reaction product was purified by column chromatography to thereby obtain the compound of interest as brown oil (5.3 g, yield: 23%).

(3) Synthesis of 4-chloro-5-ethoxycarbonyl-3-hydroxy-2,3-dihydrobenzothiophene

A solution comprising 4-chloro-5-ethoxycarbonyl-3-oxo-2,3-dihydrobenzothiophene (5.3 g) obtained in (2), dichloromethane (25 ml), and ethanol (25 ml) was cooled in an ice-bath and sodium boron hydride (0.26 g) was added thereto, after which the solution was allowed to stand overnight.

Subsequently, the obtained reaction mixture was poured into ice water and subjected to extraction with dichloromethane. The extract was dried over sodium sulfate and filtered to thereby obtain the compound of interest (5.3 g, yield: 98%).

(4) Synthesis of 4-chloro-5-ethoxycarbonylbenzothiophene

A mixture of 4-chloro-5-ethoxycarbonyl-3-hydroxy-2,3-dihydrobenzothiophene (5.3 g) obtained in (3), toluene (50 ml), and p-toluene sulfate (0.2 g) was subjected to azeotropic dehydration over 1 hour.

The resultant reaction mixture was diluted with toluene, washed with a saturated solution of sodium hydrogencarbonate, and dried over sodium sulfate, followed by filtration and concentration to thereby obtain the compound of interest as brown oil (4.6 g, yield: 95%).

(5) Synthesis of 4-chloro-5-ethoxycarbonylbenzothiophene-1,1-dioxide

A mixture containing 4-chloro-5-ethoxycarbonylbenzothiophene (4.6 g) obtained in (4), acetic acid (30 ml), and a 30 wt. % aqueous solution of hydrogen peroxide (5.4 ml) was allowed to react at 80° C. for 2 hours with stirring.

After the reaction product was allowed to cool to room temperature, it was diluted with water and filtered to thereby obtain a solid. The solid was dried and purified by column chromatography to thereby obtain the compound of interest as colorless crystals (3.7 g, yield: 95%).

(6) Synthesis of 4-chloro-5-ethoxycabonyl-2,3-dihydrobenzothiophene-1,1-dioxide

A mixture of 4-chloro-5-ethoxycarbonylbenzothiophene-1,1-dioxide (3.7 g) obtained in (5), tetrahydrofuran (40 ml), and 5% palladium/carbon was allowed to react in an atmosphere of hydrogen gas at ordinary temperature and pressure for 8 hours.

Subsequently, the resultant mixture was filtered and concentrated to thereby obtain the compound of interest as pale yellow oil (3.44 g, yield: 91%).

(7) Synthesis of 4-chloro-5-oxycabonyl-2,3-dihydrobenzothiophene-1,1-dioxide

4-Chloro-5-ethoxycarbonyl-2,3-dihydrobenzothiophene-1,1-dioxide (3.44 g) obtained in (6) was dissolved in ethanol (35 ml). To the solution, a 20 wt. % aqueous solution of sodium hydroxide (5 ml) was added and the mixture was allowed to stand overnight.

Subsequently, the reaction mixture was concentrated and acidified by adding a 5 wt. % aqueous solution of hydrochloric acid, followed by filtration and drying of the produced precipitate to thereby yield the compound of interest as colorless crystals (2.6 g, yield: 84%).

A $^1$H-NMR analysis (acetone-d$^6$; TMS standard) of the thus-obtained colorless crystals showed peaks of 3.4–3.8 (m, 4H), 7.85 (1H, d), and 8.06 (1H, d). Also, under infrared spectrum analysis, there were observed peaks at 3080 cm$^{-1}$, 3010 cm$^{-1}$, 1690 cm$^{-1}$, 1410 cm$^{-1}$, 1400 cm$^{-1}$, 1310 cm$^{-1}$, 1290 cm$^{-1}$, 1250 cm$^{31\ 1}$, 1190 cm$^{-1}$, and 1130 cm$^{-1}$. From these results, the compound was identified as 4-chloro-5-oxycabonyl-2,3-dihydrobenzothiophene-1,1-dioxide, and its measured melting point was 232–233° C.

[2] Synthesis of 4-chloro-5-(1,3-dioxocyclohexan-2-yl) carbonyl-2,3-dihydrobenzothiophene-1,1-dioxide [Compound No. A-1]

As raw materials, 4-chloro-5-oxycabonyl-2,3-dihydrobenzothiophene-1,1-dioxide (1.0 g) obtained in (1)

and a suspension (4 ml) of thionyl chloride (0.54 g) in 1,2-dichloroethane were reacted over 1 hour under reflux with heat.

From the obtained product, solvent was removed through distillation under reduced pressure, and the obtained acid chloride and 1,3-cyclohexanedione (0.47 g) were dissolved in acetonitrile (10 ml) serving as a solvent. Thereafter, at room temperature, a solution of triethylamine (0.82 g) in acetonitrile (5 ml) was added dropwise thereto.

After the mixture was stirred for 2 hours at room temperature, acetone cyanhydrin (0.01 g) was added thereto, followed by stirring for 20 hours at room temperature.

To the resultant mixture, ethyl acetate was added and subjected to extraction with saturated sodium carbonate. To an aqueous phase, 10% hydrochloric acid was added so as to adjust the pH of the phase to 1, and extraction with ethyl acetate was carried out. The thus-obtained organic phase was washed with water and aqueous saturated brine and then dried over anhydrous sodium sulfate. The solvent was removed from the product through distillation under reduced pressure to thereby obtain the compound of interest, 4-chloro-5-(1,3-dioxocyclohexan-2-yl)carbonyl-2,3-dihydrobenzothiophene-1,1-dioxide (1.24 g, yield: 90%).

The obtained target compound was subjected to $^1$H-NMR (CDCl$_3$; TMS standard) and infrared spectrometry. The results of analysis, and the chemical structure and measured melting point of the compound are shown in Table I-1.

Example I-2

Synthesis of 4-methyl-5-(1,3-dioxocyclohexan-2-yl) carbonyl-2,3-dihydrobenzothiophene-1,1-dioxide [Compound No. A-2]

The target compound was obtained in the same manner as described in Example I-1, except that 4-methyl-5-oxycabonyl -2,3-dihydrobenzothiophene-1,1-dioxide was used instead of 4-chloro-5-oxycabonyl-2,3-dihydrobenzothiophene-1,1-dioxide.

The obtained target compound was subjected to $^1$H-NMR (CDCl$_3$; TMS standard) and infrared spectrometry. The results of analysis, and the chemical structure and measured melting point of the compound are shown in Table I-1.

Example I-3

Synthesis of 4-chloro-7-methyl-5-(1,3-dioxocyclohexan-2-yl)carbonyl-2,3-dihydrobenzothiophene-1,1-dioxide [Compound No. A-3]

The target compound was obtained in the same manner as described in Example I-1, except that 4-chloro-7-methyl-5-oxycarbonyl-2,3-dihydrobenzothiophene-1,1-dioxide was used instead of 4-chloro-5-oxycarbonyl-2,3-dihydrobenzothiophene -1,1-dioxide.

The obtained target compound was subjected to $^1$H-NMR (CDCl$_3$; TMS standard) and infrared spectrometry. The results of analysis, and the chemical structure and measured melting point of the compound are shown in Table I-1.

Example I-4

Synthesis of 4,7-dimethyl-5-(1,3-dioxocyclohexan-2-yl) carbonyl-2,3-dihydrobenzothiophene-1,1-dioxide [Compound No. A-4]

The target compound was obtained in the same manner as described in Example I-1, except that 4,7-dimethyl-5-oxycarbonyl-2,3-dihydrobenzothiophene-1,1-dioxide was used instead of 4-chloro-5-oxycarbonyl-2,3-dihydrobenzothiophene -1,1-dioxide.

The obtained target compound was subjected to $^1$H-NMR (CDCl$_3$; TMS standard) and infrared spectrometry. The results of analysis, and the chemical structure and measured melting point of the compound are shown in Table I-1.

Example I-5

Synthesis of 4-methoxy-5-(1,3-dioxocyclohexan-2-yl) carbonyl-2,3-dihydrobenzothiophene-1,1-dioxide [Compound No. A-5]

The target compound was obtained in the same manner as described in Example I-1, except that 4-methoxy-5-oxycarbonyl-2,3-dihydrobenzothiophene-1,1-dioxide was used instead of 4-chloro-5-oxycarbonyl-2,3-dihydrobenzothiophene -1,1-dioxide.

The obtained target compound was subjected to $^1$H-NMR (CDCl$_3$; TMS standard) and infrared spectrometry. The results of analysis, and the chemical structure and measured melting point of the compound are shown in Table I-1.

Example I-6

Synthesis of 4-methylthio-5-(1,3-dioxocyclohexan-2-yl) carbonyl-2,3-dihydrobenzothiophene-1,1-dioxide [Compound No. A-6]

The target compound was obtained in the same manner as described in Example I-1, except that 4-methylthio-5-oxycarbonyl-2,3-dihydrobenzothiophene-1,1-dioxide was used instead of 4-chloro-5-oxycarbonyl-2,3-dihydrobenzothiophene -1,1-dioxide.

The obtained target compound was subjected to $^1$H-NMR (CDCl$_3$; TMS standard) and infrared spectrometry. The results of analysis, and the chemical structure and measured melting point of the compound are shown in Table I-1.

Example I-7

Synthesis of 4-chloro-5-(4-methyl-1,3-dioxocyclohexan-2-yl)carbonyl-2,3-dihydrobenzothiophene-1,1-dioxide [Compound No. A-7]

The target compound was obtained in the same manner as described in Example I-1, except that 4-methyl-1,3-cyclohexanedione was used instead of 1,3-cyclohexanedione.

The obtained target compound was subjected to $^1$H-NMR (CDCl$_3$; TMS standard) and infrared spectrometry. The results of analysis, and the chemical structure and measured melting point of the compound are shown in Table I-1.

Example I-8

Synthesis of 4-chloro-5-(4,4-dimethyl-1,3-dioxocyclohexan-2-yl)carbonyl-2,3-dihydrobenzo-thiophene-1,1-dioxide [Compound No. A-8]

The target compound was obtained in the same manner as described in Example I-1, except that 4,4-dimethyl-1,3-cyclohexanedione was used instead of 1,3-cyclohexanedione.

The obtained target compound was subjected to $^1$H-NMR (CDCl$_3$; TMS standard) and infrared spectrometry. The results of analysis, and the chemical structure and measured melting point of the compound are shown in Table I-1.

Example I-9

Synthesis of 4-chloro-5-(5,5-dimethyl-1,3-dioxocyclohexan-2-yl)carbonyl-2,3-dihydrobenzo-thiophene-1,1-dioxide [Compound No. A-9]

The target compound was obtained in the same manner as described in Example I-1, except that 5,5-dimethyl-1,3-cyclohexanedione was used instead of 1,3-cyclohexanedione.

The obtained target compound was subjected to $^1$H-NMR (CDCl$_3$; TMS standard) and infrared spectrometry. The results of analysis, and the chemical structure and measured melting point of the compound are shown in Table I-1.

Example I-10
Synthesis of 4-chloro-7-methyl-5-(5,5-dimethyl-1,3-dioxocyclohexan-2-yl)carbonyl-2,3-dihydrobenzothiophene-1,1-dioxide [Compound No. A-10]

The target compound was obtained in the same manner as described in Example I-1, except that 5,5-dimethyl-1,3-cyclohexanedione and 4-chloro-7-methyl-5-oxycarbonyl-2,3-dihydrobenzothiophene-1,1-dioxide were used instead of 1,3-cyclohexanedione and 4-chloro-5-oxycarbonyl-2,3-dihydrobenzothiophene-1,1-dioxide, respectively.

The obtained target compound was subjected to $^1$H-NMR (CDCl$_3$; TMS standard) and infrared spectrometry. The results of analysis, and the chemical structure and measured melting point of the compound are shown in Table I-1.

Example I-11
Synthesis of 4-chloro-7-methyl-5-(4,4-dimethyl-1,3-dioxocyclohexan-2-yl)carbonyl-2,3-dihydrobenzothiophene-1,1-dioxide [Compound No. A-11]

The target compound was obtained in the same manner as described in Example I-1, except that 4,4-dimethyl-1,3-cyclohexanedione and 4-chloro-7-methyl-5-oxycarbonyl-2,3-dihydrobenzothiophene-1,1-dioxide were used instead of 1,3-cyclohexanedione and 4-chloro-5-oxycarbonyl-2,3-dihydrobenzothiophene-1,1-dioxide, respectively.

The obtained target compound was subjected to $^1$H-NMR (CDCl$_3$; TMS standard) and infrared spectrometry. The results of analysis, and the chemical structure and measured melting point of the compound are shown in Table I-1.

Example I-12
Synthesis of 4-chloro-5-(5-methyl-1,3-dioxocyclohexan-2-yl)carbonyl-2,3-dihydrobenzothiophene-1,1-dioxide [Compound No. A-12]

The target compound was obtained in the same manner as described in Example I-1, except that 5-methyl-1,3-cyclohexanedione was used instead of 1,3-cyclohexanedione.

The obtained target compound was subjected to $^1$H-NMR (CDCl$_3$; TMS standard) and infrared spectrometry. The results of analysis, and the chemical structure and measured melting point of the compound are shown in Table I-1.

Example I-13
Synthesis of 4-chloro-5-(4,4,6-trimethyl-1,3-dioxocyclohexan-2-yl)carbonyl-2,3-dihydrobenzothiophene-1,1-dioxide [Compound No. A-13]

The target compound was obtained in the same manner as described in Example I-1, except that 4,4,6-trimethyl-1,3-cyclohexanedione was used instead of 1,3-cyclohexanedione.

The obtained target compound was subjected to $^1$H-NMR (CDCl$_3$; TMS standard) and infrared spectrometry. The results of analysis, and the chemical structure and measured melting point of the compound are shown in Table I-1.

Example I-14
Synthesis of 4-chloro-5-(4,6-dimethyl-1,3-dioxocyclohexan-2-yl)carbonyl-2,3-dihydrobenzothiophene-1,1-dioxide [Compound No. A-14]

The target compound was obtained in the same manner as described in Example I-1, except that 4,6-dimethyl-1,3-cyclohexanedione was used instead of 1,3-cyclohexanedione.

The obtained target compound was subjected to $^1$H-NMR (CDCl$_3$; TMS standard) and infrared spectrometry. The results of analysis, and the chemical structure and measured melting point of the compound are shown in Table I-1.

Example I-15
Synthesis of 4-chloro-5-(4,4,6,6-tetramethyl-1,3-dioxocyclohexan-2-yl)carbonyl-2,3-dihydrobenzothiophene-1,1-dioxide [Compound No. A-15]

The target compound was obtained in the same manner as described in Example I-1, except that 4,4,6,6-tetramethyl-1,3-cyclohexanedione was used instead of 1,3-cyclohexanedione.

The obtained target compound was subjected to $^1$H-NMR (CDCl$_3$; TMS standard) and infrared spectrometry. The results of analysis, and the chemical structure and measured melting point of the compound are shown in Table I-1.

Example I-16
Synthesis of 4-chloro-5-(4,5-dimethyl-1,3-dioxocyclohexan-2-yl)carbonyl-2,3-dihydrobenzothiophene-1,1-dioxide [Compound No. A-16]

The target compound was obtained in the same manner as described in Example I-1, except that 4,5-dimethyl-1,3-cyclohexanedione was used instead of 1,3-cyclohexanedione.

The obtained target compound was subjected to $^1$H-NMR (CDCl$_3$; TMS standard) and infrared spectrometry. The results of analysis, and the chemical structure and measured melting point of the compound are shown in Table I-1.

Example I-17
Synthesis of 4-chloro-2-methyl-5-(1,3-dioxocyclohexan-2-yl)carbonyl-2,3-dihydrobenzothiophene-1,1-dioxide [Compound No. A-17]

The target compound was obtained in the same manner as described in Example I-1, except that 4-chlodro-2-methyl-5-oxycarbonyl-2,3-dihydrobenzothiophene-1,1-dioxide was used instead of 4-chloro-5-oxycarbonyl-2,3-dihydrobenzothiophene-1,1-dioxide.

The obtained target compound was subjected to $^1$H-NMR (CDCl$_3$; TMS standard) and infrared spectrometry. The results of analysis, and the chemical structure and measured melting point of the compound are shown in Table I-1.

Example I-18
Synthesis of 4-methoxy-2-methyl-5-(1,3-dioxocyclohexan-2-yl)carbonyl-2,3-dihydrobenzothiophene-1,1-dioxide [Compound No. A-18]

The target compound was obtained in the same manner as described in Example I-1, except that 4-methoxy-2-methyl-5-oxycarbonyl-2,3-dihydrobenzothiophene-1,1-dioxide was used instead of 4-chloro-5-oxycarbonyl-2,3-dihydrobenzothiophene-1,1-dioxide.

The obtained target compound was subjected to $^1$H-NMR (CDCl$_3$; TMS standard) and infrared spectrometry. The results of analysis, and the chemical structure and measured melting point of the compound are shown in Table I-1.

Example I—19
Synthesis of a sodium salt of 4-chloro-5-(1,3-dioxocyclohexan-2-yl)carbonyl-2,3-dihydrobenzothiophene-1,1-dioxide [Compound No. A-19]

4–Chloro-5-(1,3-dioxocyclohexan-2-yl)carbonyl-2,3-dihydrobenzothiophene-1,1-dioxide (0.1 g) obtained in the same manner as described in Example I-1 was dissolved in tetrahydrofuran (8 ml) and the solution was added dropwise to a suspension of sodium hydroxide (0.006 g) in tetrahydrofuran (2 ml).

After the mixture was stirred at room temperature for 25 hours, the solvent was removed through distillation under reduced pressure, and extraction with ethyl acetate was carried out. The extract was dried and crystallized to thereby yield the compound of interest (0.08 g, yield: 75%).

The chemical structure and the measured melting point of the obtained target compound are shown in Table I-1.

Example I-20
Synthesis of 4-bromo-5-(1,3-dioxocyclohexan-2-yl) carbonyl-2,3-dihydrobenzothiophene-1,1-dioxide [Compound No. A-20]

The target compound was obtained in the same manner as described in Example I-1, except that 4-bromo-5-oxycarbonyl-2,3-dihydrobenzothiophene-1,1-dioxide was used instead of 4-chloro-5-oxycarbonyl-2,3-dihydrobenzothiophene-1,1-dioxide.

The obtained target compound was subjected to $^1$H-NMR (CDCl$_3$; TMS standard) and infrared spectrometry. The results of analysis, and the chemical structure and measured melting point of the compound are shown in Table I-1.

Example I-21
Synthesis of 4-cyano-5-(1,3-dioxocyclohexan-2-yl) carbonyl-2,3-dihydrobenzothiophene-1,1-dioxide [Compound No. A-21]

The target compound was obtained in the same manner as described in Example I-1, except that 4-cyano-5-oxycarbonyl-2,3-dihydrobenzothiophene-1,1-dioxide was used instead of 4-chloro-5-oxycarbonyl-2,3-dihydrobenzothiophene-1,1-dioxide.

The obtained target compound was subjected to $^1$H-NMR (CDCl$_3$; TMS standard) and infrared spectrometry. The results of analysis, and the chemical structure and measured melting point of the compound are shown in Table I-1.

In the Table I-1, "(1)" to "(6)" indicates respectively as follows.

(1) Example No.
(2) Compound No.
(3) Chemical structure
(4) NMR/ppm (CDCl$_3$, TMS standard)
(5) Infra Red Absorption (cm$^{-1}$)
(6) Property (mp: °C.)

TABLE I-1

| (1) | (2) | (3) | (4) | (5) | (6) |
|---|---|---|---|---|---|
| I-1 | A-1 | [structure: 4-Cl-2,3-dihydrobenzothiophene-1,1-dioxide coupled to 2-(1,3-dioxocyclohexan-2-yl, enol OH)carbonyl] | 1.9-2.3(2H,m); 2.3-2.7(2H,m); 2.6-3.0(2H,m); 3.1-3.8(4H,m); 7.32(1H,d); 7.69(1H,d) | 1675, 1575, 1550, 1400, 1295, 1125 | 156.0–159.7 |
| I-2 | A-2 | [structure: 4-Me analog] | 1.9-2.2(2H,m); 2.20(3H,s); 2.3-2.6(2H,m); 2.7-3.0(2H,m); 3.2-3.7(4H,m); 7.17(1H,d); 7.60(1H,d) | 1670, 1590, 1300, 1190, 1120 | 203.8–204.3 |
| I-3 | A-3 | [structure: 4-Cl, 7-Me analog] | 1.9-2.3(2H,m); 2.4-2.6(2H,m); 2.60(3H,s); 2.7-2.9(2H,m); 3.2-3.7(4H,m); 7.03(1H,s) | 1670, 1560, 1420, 1300, 1200, 1135 | 213.0–214.7 |
| I-4 | A-4 | [structure: 4,7-diMe analog] | 1.9-2.2(2H,m); 2.13(3H,s); 2.3-2.6(2H,m); 2.58(3H,s); 2.7-3.0(2H,m); 3.1-3.7(4H,m); 6.90(1H,s) | 1675, 1580, 1425, 1410, 1295, 1125 | 218.5–220.7 |
| I-5 | A-5 | [structure: 4-OMe analog] | 1.9-2.3(2H,m); 2.3-2.6(2H,m); 2.7-2.9(2H,m); 3.3-3.6(4H,m); 3.83(3H,s); 7.23(1H,d); 7.50(1H,d) | 1660, 1590, 1400, 1300, 1175, 1115 | syrup |

TABLE I-1-continued

| (1) | (2) | (3) | (4) | (5) | (6) |
|---|---|---|---|---|---|
| I-6 | A-6 | | 1.9-2.2(2H,m)<br>2.25(3H,s)<br>2.3-2.6(2H,m)<br>2.7-3.0(2H,m)<br>3.54(4H,s)<br>7.21(1H,d)<br>7.74(1H,d) | 1675<br>1570<br>1405<br>1300<br>1175<br>1125 | 195.2–<br>196.1 |
| I-7 | A-7 | | 1.09(3H,d)<br>1.5-3.0(5H,m)<br>3.2-3.7(4H,m)<br>7.26(1H,d)<br>7.66(1H,d) | 1680<br>1580<br>1565<br>1315<br>1195<br>1140 | syrup |
| I-8 | A-8 | | 1.0-1.5(6H,m)<br>1.7-3.0(4H,m)<br>3.2-3.7(4H,m)<br>7.29(1H,d)<br>7.70(1H,d) | 1600<br>1390<br>1305<br>1185<br>1170<br>1120 | 161.1–<br>161.6 |
| I-9 | A-9 | | 1.14(6H,s)<br>2.3-2.7(4H,m)<br>3.2-3.7(4H,m)<br>7.30(1H,d)<br>7.69(1H,d) | 1670<br>1585<br>1555<br>1305<br>1195<br>1135 | 142.9–<br>146.7 |
| I-10 | A-10 | | 1.09(6H,s)<br>2.32(2H,s)<br>2.62(3H,s)<br>2.68(2H,s)<br>3.4-3.7(4H,m)<br>7.05(1H,s) | 2970<br>1660<br>1580<br>1290<br>1220<br>1190 | syrup |
| I-11 | A-11 | | 1.34(6H,s)<br>1.8-2.0(2H,m)<br>2.3-2.9(2H,m)<br>2.63(3H,s)<br>3.3-3.7(4H,m)<br>7.03(1H,s) | 2970<br>1670<br>1580<br>1420<br>1380<br>1300 | syrup |
| I-12 | A-12 | | 1.13(3H,d)<br>2.0-3.0(5H,m)<br>3.3-3.7(4H,m)<br>7.30(1H,d)<br>7.70(1H,d) | 2970<br>1670<br>1590<br>1400<br>1300<br>1180 | syrup |
| I-13 | A-13 | | 1.0-1.4(9H,m)<br>1.6-2.0(2H,m)<br>2.5-3.0(1H,m)<br>3.3-3.7(4H,m)<br>7.30(1H,d)<br>7.70(1H,d) | 2980<br>1730<br>1670<br>1580<br>1410<br>1310 | syrup |

TABLE I-1-continued

| (1) | (2) | (3) | (4) | (5) | (6) |
|---|---|---|---|---|---|
| I-14 | A-14 | | 1.07(3H,d)<br>1.09(3H,d)<br>1.8-2.6(3H,m)<br>2.8-3.2(1H;m)<br>3.3-3.7(4H,m)<br>7.30(1H,d)<br>7.70(1H,d) | | syrup |
| I-15 | A-15 | | 1.19(12H,d)<br>1.8-1.9(2H,m)<br>3.3-3.6(4H,m)<br>7.30(1H,d)<br>7.70(1H,d) | | syrup |
| I-16 | A-16 | | 1.0-1.6(6H,m)<br>2.0-2.8(4H,m)<br>3.3-3.7(4H,m)<br>7.30(1H,d)<br>7.70(1H,d) | | syrup |
| I-17 | A-17 | | 1.56(3H,d)<br>1.9-2.3(2H,m)<br>2.3-2.6(2H,m)<br>2.7-3.1(3H,m)<br>3.4-3.8(2H,m)<br>7.28(1H,d)<br>7.71(1H,d) | 1670<br>1575<br>1555<br>1450<br>1305<br>1140 | 152.5–154.6 |
| I-18 | A-18 | | 1.45(3H,d)<br>2.0-3.1(8H,m)<br>3.5-3.7(1H,m)<br>3.79(3H,s)<br>7.30(1H,d)<br>7.44(1H,d) | 1680<br>1580<br>1410<br>1300<br>1130<br>1010 | syrup |
| I-19 | A-19 | | — | — | — |
| I-20 | A-20 | | 1.9-2.3(2H,m)<br>2.3-2.6(2H,m)<br>2.7-3.0(2H,m)<br>3.2-3.7(4H,m)<br>7.24(1H,d)<br>7.74(1H,d) | 1670<br>1560<br>1395<br>1300<br>1195<br>1125 | |
| I-21 | A-21 | | 1.9-2.3(2H,m)<br>2.3-3.0(4H,m)<br>3.58(4H,s)<br>7.51(1H,d)<br>7.97(1H,d) | 1660<br>1600<br>1580<br>1555<br>1300<br>1125 | 208.8–242.3 |

Example I-22
(1) Preparation of Herbicide

Talc (57 parts by weight) and bentonite (40 parts by weight), both serving as carriers, and sodium alkylbenzenesulfate (3 parts by weight) serving as a surfactant were homogeneously ground and mixed to thereby obtain a carrier for water-dispersible powder.

Subsequently, to the water-dispersible powder (90 parts by weight), the triketone derivative (compound No. A-1) produced in Example I-1 (10 parts by weight) was added, and the resultant mixture was homogeneously ground and mixed to thereby obtain a herbicide.

(2) Biological Tests of Herbicide (i) Biological Test 1 (Soaking in water/Treatment on the 3rd Day After Transplantation)

A Wagner pot (1/2000 are) was filled with paddy soil, and seeds of barnyard grass were planted on the surface layer of the soil, and further, rice seedlings grown to the 2.5-leaf stage were transplanted.

Subsequently, water was poured in the pot to a height of 3 cm above the soil surface, and placed in a greenhouse where the temperature was maintained at 20–25° C., to thereby grow the plant under suitable conditions.

On the 3rd day after transplantation, the herbicide prepared in (1) above was applied to the plant in a predetermined amount. On the 30th day after treatment with the herbicide, weed-killing ratio, herbicidal effect, and extent of chemical injury to paddy rice were examined.

(ii) Biological Test 2 (Soaking in Water/Treatment on the 10th Day After Transplantation)

A Wagner pot (1/2000 are) was filled with paddy soil, and seeds of barnyard grass were planted on the surface layer of the soil. and further, a rice seedling grown to the 2.5-leaf stage was transplanted.

Next, water was poured to the pot to a height of 3 cm above the soil surface, and placed in a greenhouse where the temperature was maintained at 20–25° C., to thereby grow the plant under suitable conditions.

On the 10th day after transplantation, the herbicide prepared in (1) above was applied to the plant in a predetermined amount. On the 30th day after treatment with the herbicide, weed-killing ratio, herbicidal effect, and extent of chemical injury to paddy rice were examined.

In Biological tests 1 and 2, herbicidal effect and extent of chemical injury were evaluated according to the below-described standards.

1) Weed-killing Ratio

Weight of plants growing in the soil which had been treated with the herbicide and weight of plants growing in the soil which had not been treated with the herbicide were measured, and weed-killing ratio (%) was calculated according to the following formula:

Weed-killing ratio (%)=[1−(Weight of plants growing in the soil which had been treated with the herbicide)/(weight of plants growing in the soil which had not been treated with the herbicide )]×100

2) Herbicidal Effect

Herbicidal effect was evaluated according to the following criteria.

| [Rating of herbicidal effect] | [Herbicidal effect (weed-killing ratio)] |
|---|---|
| 0 | less than 5% (almost no effect) |
| 1 | 5% or more and less than 20% |
| 2 | 20% or more and less than 40% |
| 3 | 40% or more and less than 70% |
| 4 | 70% or more and less than 90% |
| 5 | 90% or more (almost completely withered) |

3) Chemical Injury to Paddy Rice

Chemical injury to paddy rice was evaluated according to the following criteria.

| [Rating of chemical injury to paddy rice] | [Chemical injury to paddy rice] |
|---|---|
| 0 | No chemical injury to paddy rice was found. |
| 1 | Chemical injury to paddy rice was hardly found. |
| 2 | Slight chemical injury to paddy rice was found. |
| 3 | Chemical injury to paddy rice was found. |
| 4 | Chemical injury to paddy rice was predominantly found. |
| 5 | Paddy rice was almost completely withered. |

The biological test results are shown in Table I-2.

Example I-23 to I-40

(1) Preparation of Herbicides

Various herbicides were prepared in the same manner as described in Example I-22 (1), except that the respective triketone derivatives obtained in Examples I-2 to I-21 were used instead of the triketone derivative used in Example I-22 (1).

(2) Biological Tests of Herbicide

Biological tests of herbicide were carried out in the same manner as described in Example I-22 (2), except that the respective herbicides prepared in (1) were used instead of the herbicide prepared in Example I-22 (1).

The biological test results are shown in Table I-2.

Comparative Example I-1

(1) Preparation of Herbicide

A herbicide was prepared in the same manner as described in Example I-22 (1), except that a publicly known compound represented by the following formula was used instead of the triketone derivative.

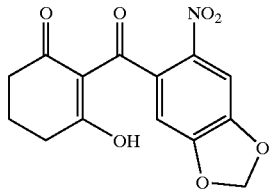

(2) Biological Tests of Herbicide

Biological tests of herbicide were carried out in the same manner as described in Example I-22 (2), except that a herbicide prepared in (1) was used instead of the herbicide prepared in Example I-22 (1).

The biological test results are shown in Table I-2.

Comparative Example I-2

(1) Preparation of Herbicide

A herbicide was prepared in the same manner as described in Example I-22 (1), except that a publicly known compound represented by the following formula was used instead of the triketone derivative.

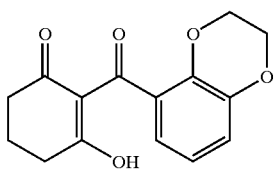

(2) Biological Tests of Herbicide

Biological tests of herbicide were carried out in the same manner as described in Example I-22 (2), except that a herbicide prepared in (1) was used instead of the herbicide prepared in Example I-22 (1).

The biological test results are shown in Table I-2.

Comparative Example I-3

(1) Preparation of Herbicide

A herbicide was prepared in the same manner as described in Example I-22 (1), except that a publicly known compound represented by the following formula was used instead of the triketone derivative.

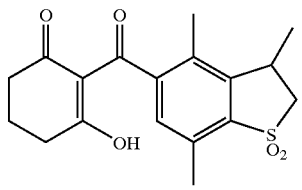

(2) Biological Tests of Herbicide

Biological tests of herbicide were carried out in the same manner as described in Example I-22 (2), except that a herbicide prepared in (1) was used instead of the herbicide prepared in Example I-22 (1).

The biological test results are shown in Table I-2.

Comparative Example I-4

(1) Preparation of Herbicide

A herbicide was prepared in the same manner as described in Example I-22(1), except that a publicly known compound represented by the following formula was used instead of the triketone derivative.

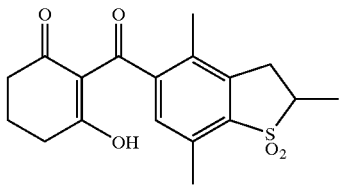

(2) Biological Tests of Herbicide

Biological tests of herbicide were carried out in the same manner as described in Example I-22 (2), except that a herbicide prepared in (1) was used instead of the herbicide prepared in Example I-22 (1).

The biological test results are shown in Table I-2(1) and (2).

In the Table I-2 (1) and (2), "(1)" to "(11)" indicates respectively as follows.

(1) Example No.
(2) Compound No.
(3) Dose (g/ha)
(4) Treatment performed 3 days after transplantation
(5) Treatment performed 10 days after transplantation
(6) Weed-killing effect
(7) Chemical injury
(8) *Echinochloa crug-galli*
(9) *Scirups juncoides*
(10) Transplanted paddy rice plant
(11) Comparative Example

TABLE I-2(1)

| | | | (4) | | | (5) | |
| | | | (6) | | (7) | (6) | |
| (1) | (2) | (3) | (8) | (9) | (10) | (8) | (9) |
|---|---|---|---|---|---|---|---|
| I-22 | A-1 | 100 | 5 | 5 | 0 | 5 | 5 |
| | | 200 | 5 | 5 | 0 | 5 | 5 |
| I-23 | A-2 | 100 | 4 | 5 | 0 | 3 | 5 |
| | | 200 | 5 | 5 | 0 | 4 | 5 |
| I-24 | A-3 | 100 | 5 | 5 | 1 | 5 | 5 |
| | | 200 | 5 | 5 | 3 | 5 | 5 |
| I-25 | A-4 | 100 | 4 | 5 | 0 | 4 | 5 |
| | | 200 | 5 | 5 | 1 | 4 | 5 |
| I-26 | A-5 | 100 | 3 | 4 | 0 | 3 | 4 |
| | | 200 | 5 | 5 | 0 | 4 | 4 |
| I-27 | A-6 | 100 | 5 | 5 | 1 | 4 | 4 |
| | | 200 | 5 | 5 | 3 | 5 | 5 |
| I-28 | A-7 | 100 | 5 | 5 | 1 | 4 | 5 |
| | | 200 | 5 | 5 | 2 | 5 | 5 |
| I-29 | A-8 | 100 | 5 | 5 | 1 | 5 | 5 |
| | | 200 | 5 | 5 | 3 | 5 | 5 |
| I-30 | A-9 | 100 | 5 | 5 | 1 | 5 | 5 |
| | | 200 | 5 | 5 | 3 | 5 | 5 |
| I-31 | A-10 | 100 | 5 | 5 | 1 | 5 | 5 |
| | | 200 | 5 | 5 | 3 | 5 | 5 |
| I-32 | A-11 | 100 | 5 | 5 | 1 | 5 | 5 |
| | | 200 | 5 | 5 | 3 | 5 | 5 |
| I-33 | A-12 | 100 | 5 | 5 | 1 | 5 | 5 |
| | | 200 | 5 | 5 | 2 | 5 | 5 |
| I-34 | A-13 | 100 | 5 | 5 | 1 | 5 | 5 |
| | | 200 | 5 | 5 | 3 | 5 | 5 |
| I-35 | A-14 | 100 | 5 | 5 | 1 | 5 | 5 |
| | | 200 | 5 | 5 | 2 | 5 | 5 |
| I-36 | A-15 | 100 | 5 | 5 | 1 | 5 | 5 |
| | | 200 | 5 | 5 | 3 | 5 | 5 |
| I-37 | A-16 | 100 | 5 | 5 | 1 | 5 | 5 |
| | | 200 | 5 | 5 | 3 | 5 | 5 |
| I-38 | A-17 | 100 | 3 | 4 | 0 | 3 | 4 |
| | | 200 | 4 | 5 | 1 | 4 | 4 |
| I-39 | A-18 | 100 | 3 | 4 | 0 | 2 | 4 |
| | | 200 | 4 | 4 | 1 | 3 | 4 |
| I-40 | A-19 | 100 | 5 | 5 | 0 | 5 | 5 |
| | | 200 | 5 | 5 | 1 | 5 | 5 |
| I-41 | A-20 | 100 | 5 | 5 | 0 | 5 | 5 |
| | | 200 | 5 | 5 | 0 | 5 | 5 |
| I-42 | A-21 | 100 | 5 | 5 | 0 | 5 | 5 |
| | | 200 | 5 | 5 | 0 | 5 | 5 |

TABLE I-2(2)

| | | (4) | | | (5) | |
| | | (6) | (7) | | (6) | |
| (11) | (3) | (8) | (9) | (10) | (8) | (9) |
|---|---|---|---|---|---|---|
| I-1 | 100 | 5 | 4 | 3 | 0 | 1 |
| | 200 | 5 | 5 | 4 | 3 | 2 |
| I-2 | 100 | 0 | 0 | 0 | 0 | 0 |
| | 200 | 1 | 1 | 0 | 0 | 0 |
| I-3 | 110 | 4 | 3 | 3 | 3 | 2 |
| | 200 | 5 | 4 | 4 | 5 | 3 |
| I-4 | 110 | 3 | 3 | 2 | 1 | 1 |
| | 200 | 5 | 3 | 4 | 2 | 2 |

SECOND ASPECT OF THE INVENTION

Example II-1

[1] Synthesis of 4-chloro-5-oxycarbonyl-2,3-dihydrobenzothiophene-1,1-dioxide (1) Synthesis of ethyl 4-carboxymethylsulfenyl-2-chlorobenzoate A mixture containing ethyl 2,4-dichlorobenzoate (10.0 g), potassium carbonate (9.44 g), dimethylformamide (50 ml), and mercaptoacetic acid (3.8 ml) was allowed to react with heat at 80° C. for 4 hours.

Next, the resultant reaction mixture was poured into ice water and was subjected to extraction with ethyl acetate. The extract was dried over sodium sulfate and filtered, then concentrated to thereby obtain a crude reaction product (12.3 g).

(2) Synthesis of 4-chloro-5-ethoxycarbonyl-3-oxo-2,3-dihydrobenzothiophene

A mixture of ethyl 4-carboxymethylsulfenyl-2-chlorobenzoate (12.3 g) obtained in (1), 1,2-dichloroethane (36 ml), and thionyl chloride (3.9 ml) was refluxed with heat over 1 hour.

Acid chloride obtained by concentration of the reaction mixture was dissolved in dichloromethane (36 ml). The solution was added dropwise under cooling on ice over 1 hour to a solution of aluminum chloride (14.3 g, 107 mmol) and dichloromethane (150 ml) prepared in advance, after which the reaction was continued for a further 2 hours at room temperature.

The thus-obtained reaction mixture was poured into ice water and subjected to extraction with dichloromethane. The extract was dried over sodium sulfate, filtered, and concentrated to thereby obtain a crude reaction product in the form of liver brown oil (12.3 g). Further, the crude reaction product was purified by column chromatography to thereby obtain the compound of interest as brown oil (5.3 g, yield: 23%).

(3) Synthesis of 4-chloro-5-ethoxycarbonyl-3-hydroxy-2,3-dihydrobenzothiophene

A solution comprising 4-chloro-5-ethoxycarbonyl-3-oxo-2,3-dihydrobenzothiophene (5.3 g) obtained in (2), dichloromethane (25 ml), and ethanol (25 ml) was cooled in an ice-bath and sodium boron hydride (0.26 g) was added thereto, after which the solution was allowed to stand overnight.

Subsequently, the obtained reaction mixture was poured into ice water and subjected to extraction with dichloromethane. The extract was dried over sodium sulfate and filtered to thereby obtain the compound of interest (5.3 g, yield: 98%).

(4) Synthesis of 4-chloro-5-ethoxycarbonylbenzothiophene

A mixture of 4-chloro-5-ethoxycarbonyl-3-hydroxy-2,3-dihydrobenzothiophene (5.3 g) obtained in (3), toluene (50 ml), and p-toluene sulfate (0.2 g) was subjected to azeotropic dehydration over 1 hour.

The resultant reaction mixture was diluted with toluene, washed with a saturated solution of sodium hydrogencarbonate, and dried over sodium sulfate, followed by filtration and concentration to thereby obtain the compound of interest as brown oil (4.6 g, yield: 95%).

(5) Synthesis of 4-chloro-5-ethoxycarbonylbenzothiophene-1,1-dioxide

A mixture containing 4-chloro-5-ethoxycarbonylbenzothiophene (4.6 g) obtained in (4), acetic acid (30 ml), and a 30 wt. % aqueous solution of hydrogen peroxide (5.4 ml) was allowed to react at 80° C. for 2 hours with stirring.

After the reaction product was allowed to cool to room temperature, it was diluted with water and filtered to thereby obtain a solid. The solid was dried and purified by column chromatography to thereby obtain the compound of interest as colorless crystals (3.7 g, yield: 95%).

(6) Synthesis of 4-chloro-5-ethoxycarbonyl-2,3-dihydrobenzothiophene-1,1-dioxide A mixture of 4-chloro-5-ethoxycarbonylbenzothiophene-1,1-dioxide (3.7 g) obtained in (5), tetrahydrofuran (40 ml), and 5% palladium/carbon was allowed to react in an atmosphere of hydrogen gas at ordinary temperature and pressure for 8 hours.

Subsequently, the resultant mixture was filtered and concentrated to thereby obtain the compound of interest as pale yellow oil (3.44 g, yield: 91%).

(7) Synthesis of 4-chloro-5-oxycarbonyl-2,3-dihydrobenzothiophene-1,1-dioxide

4–Chloro-5-ethoxycarbonyl-2,3-dihydrobenzothiophene-1,1-dioxide (3.44 g) obtained in (6) was dissolved in ethanol (35 ml). To the solution, a 20 wt. % aqueous solution of sodium hydroxide (5 ml) was added and the mixture was allowed to stand overnight.

Subsequently, the reaction mixture was concentrated and acidified by adding a 5 wt. % aqueous solution of hydrochloric acid, followed by filtration and drying of the produced precipitate to thereby yield the compound of interest as colorless crystals (2.6 g, yield: 84%).

A $^1$H-NMR analysis (acetone-d$^6$; TMS standard) of the thus-obtained colorless crystals showed peaks of 3.4–3.8 (m, 4H), 7.85 (1H, d), and 8.06 (1H, d). Also, under infrared spectrum analysis, there were observed peaks at 3080 cm$^{-1}$, 3010 cm$^{-1}$, 1690 cm$^{-1}$, 1410 cm$^{-1}$, 1400 cm$^{-1}$, 1310 cm$^{-1}$, 1290 cm$^{-1}$, 1250 cm$^{-1}$, 1190 cm$^{-1}$, and 1130 cm$^{-1}$. From these results, the compound was identified as 4-chloro-5-oxycarbonyl-2,3-dihydrobenzothiophene-1,1-dioxide, and its measured melting point was 232–233° C.

[2] Synthesis of 4-chloro-5-(1,3-dioxocyclohexan-2-yl)carbonyl-2,3-dihydrobenzothiophene-1,1-dioxide As raw materials, 4-chloro-5-oxycarbonyl-2,3-dihydrobenzothiophene-1,1-dioxide (1.0 g) obtained in (7) and a suspension (4 ml) of thionyl chloride (0.54 g) in 1,2-dichloroethane were reacted over 1 hour under reflux with heat.

The solvent was removed from the obtained product through distillation under reduced pressure, and the obtained acid chloride and 1,3-cyclohexanedione (0.47 g) were dissolved in acetonitrile (10 ml) serving as a solvent. Thereafter, at room temperature, a solution of triethylamine (0.82 g) in acetonitrile (5 ml) was added dropwise thereto.

After the mixture was stirred for 2 hours at room temperature, acetone cyanhydrin (0.01 g) was added thereto, followed by stirring for 20 hours at room temperature.

To the resultant mixture, ethyl acetate was added and subjected to extraction with saturated sodium carbonate. To an aqueous phase, 10% hydrochloric acid was added so as to adjust the pH of the phase to 1 and extraction with ethyl acetate was carried out. The thus-obtained organic phase was washed with water and aqueous saturated brine, and then dried over anhydrous sodium sulfate. The solvent was removed from the product through distillation under reduced pressure to thereby obtain the compound of interest, 4-chloro-5-(1,3-dioxocyclohexan-2-yl)carbonyl-2,3-dihydrobenzothiophene-1,1-dioxide (1.24 g, yield: 90%).

[3] Synthesis of 4-chloro-5-(3-chloro-1-oxocyclohexan-2-yl)carbonyl-2,3-dihydrobenzothiophene-1,1-dioxide [Compound No. B-1]

4-Chloro-5-(1,3-dioxocyclohexan-2-yl)carbonyl-2,3-dihydrobenzothiophene-1,1-dioxide (1.00 g) obtained in [2] was dissolved in 1,2-dichloroethane (5 ml) and to the resultant solution, at room temperature, oxalyl chloride (0.56 g) and dimethylformamide (0.01 g) were added, followed by reaction over 1 hour under reflux with heat.

Subsequently, from the resultant mixture, solvent was removed through distillation under reduced pressure, and the obtained crude product was purified by column chromatography to thereby yield 4-chloro-5-(3-chloro-1-oxocyclohexan-2-yl)carbonyl-2,3-dihydrobenzothiophene-1,1-dioxide (0.99 g, yield: 94%).

The obtained target compound was subjected to $^1$H-NMR (CDCl$_3$; TMS standard) and infrared spectrometry. The results of analysis, and the chemical structure and measured melting point of the compound are shown in Table II-1.

Example II-2

Synthesis of 4-chloro-5-(3-ethylthio-1-oxocyclohexan-2-yl)carbonyl-2,3-dihydrobenzothiophene-1,1-dioxide [Compound No. B-2]

4-Chloro-5-(3-chloro-1-oxocyclohexan-2-yl)carbonyl-2,3-dihydrobenzothiophene-1,1-dioxide (0.50 g) and ethanethiol (0.15 g) were dissolved in 1,2-dichloroethane (5 ml) and to the resultant solution, at room temperature, triethylamine (0.15 g) was added, followed by reaction for 5 hours with stirring.

After the resultant mixture was combined with water and subjected to extraction with ethyl acetate, the organic phase was washed with aqueous saturated brine, and dried over anhydrous sodium sulfate. Further, the solvent was removed through distillation under reduced pressure, and the obtained crude product was purified by column chromatography to thereby yield 4-chloro-5-(3-ethylthio-1-oxocyclohexan-2-yl)carbonyl-2,3-dihydrobenzothiophene-1,1-dioxide (0.50 g, yield: 83%).

The obtained target compound was subjected to $^1$H-NMR (CDCl$_3$; TMS standard) and infrared spectrometry. The results of analysis, and the chemical structure and measured melting point of the compound are shown in Table II-1.

Example II-3

Synthesis of 4-chloro-5-(3-phenylthio-1-oxocyclohexan-2-yl)carbonyl-2,3-dihydrobenzothiophene-1,1-dioxide [Compound No. B-3]

The target compound was prepared in the same manner as described in Example II-2, except that benzenethiol was used instead of ethanethiol.

The obtained target compound was subjected to $^1$H-NMR (CDCl$_3$; TMS standard) and infrared spectrometry. The results of analysis, and the chemical structure and measured melting point of the compound are shown in Table II-1.

Example II-4

Synthesis of 4-chloro-7-methyl-5-(3-chloro-1-oxocyclohexan-2-yl)carbonyl-2,3-dihydrobenzothiophene-1,1-dioxide [Compound No. B-4]

The target compound was prepared in the same manner as described in Example II-1, except that 4-chloro-7-methyl-5-(1,3-dioxocyclohexan-2-yl)carbonyl-2,3-dihydrobenzothiophene-1,1-dioxide was used instead of 4-chloro-5-(1,3-dioxocyclohexan-2-yl)carbonyl-2,3-dihydrobenzothiophene-1,1-dioxide.

The obtained target compound was subjected to $^1$H-NMR (CDCl$_3$; TMS standard) and infrared spectrometry. The results of analysis, and the chemical structure and measured melting point of the compound are shown in Table II-1.

Example II-5

Synthesis of 4-chloro-7-methyl-5-(3-phenylthio-1-oxocyclohexan-2-yl)carbonyl-2,3-dihydrobenzothiophene-1,1-dioxide [Compound No. B-5]

The target compound was prepared in the same manner as described in Example II-2, except that 4-chloro-7-methyl-5-(3-chloro-1-oxocyclohexan-2-yl)carbonyl-2,3-dihydrobenzothiophene-1,1-dioxide and benzenethiol were used instead of 4-chloro-5-(3-chloro-1-oxocyclohexan-2-yl)carbonyl-2,3-dihydrobenzothiophene-1,1-dioxide and ethanethiol, respectively.

The obtained target compound was subjected to $^1$H-NMR (CDCl$_3$; TMS standard) and infrared spectrometry. The results of analysis, and the chemical structure and measured melting point of the compound are shown in Table II-1.

Example II-6

Synthesis of 4-chloro-5-(3-bromo-1-oxocyclohexan-2-yl)carbonyl-2,3-dihydrobenzothiophene-1,1-dioxide [Compound No. B-6]

The target compound was prepared in the same manner as described in Example II-1, except that oxalyl bromide was used instead of oxalyl chloride.

The obtained target compound was subjected to $^1$H-NMR (CDCl$_3$; TMS standard) and infrared spectrometry. The results of analysis, and the chemical structure and measured melting point of the compound are shown in Table II-1.

Example II-7

Synthesis of 4-chloro-5-(3-methylthio-1-oxocyclohexan-2-yl)carbonyl-2,3-dihydrobenzothiophene-1,1-dioxide [Compound No. B-7]

The target compound was prepared in the same manner as described in Example II-2, except that methanethiol was used instead of ethanethiol.

The obtained target compound was subjected to $^1$H-NMR (CDCl$_3$; TMS standard) and infrared spectrometry. The results of analysis, and the chemical structure and measured melting point of the compound are shown in Table II-1.

Example II-8

Synthesis of 4-chloro-5-[3-(3-propyl)thio-1-oxocyclohexan-2-yl]carbonyl-2,3-dihydrobenzothiophene-1,1-dioxide [Compound No. B-8]

The target compound was prepared in the same manner as described in Example II-2, except that 1-propanethiol was used instead of ethanethiol.

The obtained target compound was subjected to $^1$H-NMR (CDCl$_3$; TMS standard) and infrared spectrometry. The results of analysis, and the chemical structure and measured melting point of the compound are shown in Table II-1.

Example II-9

Synthesis of 4-chloro-5-(3-isopropylthio-1-oxocyclohexan-2-yl)carbonyl-2,3-dihydrobenzothiophene-1,1-dioxide [Compound No. B-9]

The target compound was prepared in the same manner as described in Example II-2, except that 2-propanethiol was used instead of ethanethiol.

The obtained target compound was subjected to $^1$H-NMR (CDCl$_3$; TMS standard) and infrared spectrometry. The results of analysis, and the chemical structure and measured melting point of the compound are shown in Table II-1.

Example II-10
Synthesis of 4-chloro-5-[3-(4-butyl)thio-1-oxocyclohexan-2-yl)carbonyl-2,3-dihydrobenzothiophene-1,1-dioxide [Compound No. B-10]

The target compound was prepared in the same manner as described in Example II-2, except that 1-butanethiol was used instead of ethanethiol.

The obtained target compound was subjected to $^1$H-NMR (CDCl$_3$; TMS standard) and infrared spectrometry. The results of analysis, and the chemical structure and measured melting point of the compound are shown in Table II-1.

Example II-11
Synthesis of 4-chloro-5-(3-benzylthio-1-oxocyclohexan-2-yl)carbonyl-2,3-dihydrobenzothiophene-1,1-dioxide [Compound No. B-11]

The target compound was prepared in the same manner as described in Example II-2, except that benzylthiol was used instead of ethanethiol.

The obtained target compound was subjected to $^1$H-NMR (CDCl$_3$; TMS standard) and infrared spectrometry. The results of analysis, and the chemical structure and measured melting point of the compound are shown in Table II-1.

Example II-12
Synthesis of 4-chloro-5-[3-(N-methoxymethyl)amino-1-oxocyclohexan-2-yl]carbonyl-2,3-dihydrobenzothiophene-1,1-dioxide [Compound No. B-12]

As raw materials, 4-chloro-5-(3-chloro-1-oxocyclohexan-2-yl)carbonyl-2,3-dihydrobenzothiophene-1,1-dioxide (0.50 g) and N,O-dimethylhydroxylamine hydrochloride (0.14 g) were dissolved in 1,2-dichloroethane (5 ml) and to the resultant solution, triethylamine (0.15 g) was added, followed by stirring for 5 hours to thereby react the solution.

After the resultant mixture was combined with water, and then subjected to extraction with ethyl acetate, the extract was washed with aqueous saturated brine and dried over anhydrous sodium sulfate. Further, the solvent was evaporated under reduced pressure, and the obtained crude product was purified by column chromatography to thereby yield 4-chloro-5-[3-(N-methoxymethyl)amino-1-oxocyclohexan-2-yl]carbonyl-2,3-dihydrobenzothiophene-1,1-dioxide (0.43 g, yield: 80%).

The obtained target compound was subjected to $^1$H-NMR (CDCl$_3$; TMS standard) and infrared spectrometry. The results of analysis, and the chemical structure and measured melting point of the compound are shown in Table II-1.

Example II-13
Synthesis of 4-chloro-5-(3-dimethylamino-1-oxocyclohexan-2-yl)carbonyl-2,3-dihydrobenzothiophene-1,1-dioxide [Compound No. B-13]

The target compound was prepared in the same manner as described in Example II-12, except that dimethylamine hydrochloride was used instead of N,O-dimethylhydroxylamine hydrochloride.

The obtained target compound was subjected to $^1$H-NMR (CDCl$_3$; TMS standard) and infrared spectrometry. The results of analysis, and the chemical structure and measured melting point of the compound are shown in Table II-1.

Example II-14
Synthesis of 4-chloro-5-[3-(4-methylphenyl)thio-1-oxocyclohexan-2-yl]carbonyl-2,3-dihydrobenzothiophene-1,1-dioxide [Compound No. B-14]

The target compound was prepared in the same manner as described in Example II-2, except that 4-methylbenzenethiol was used instead of ethanethiol.

The obtained target compound was subjected to $^1$H-NMR (CDCl$_3$; TMS standard) and infrared spectrometry. The results of analysis, and the chemical structure and measured melting point of the compound are shown in Table II-1.

Example II-15
Synthesis of 4-chloro-5-[3-(3-methylphenyl)thio-1-oxocyclohexan-2-yl]carbonyl-2,3-dihydrobenzothiophene-1,1-dioxide [Compound No. B-15]

The target compound was prepared in the same manner as described in Example II-2, except that 3-methylbenzenethiol was used instead of ethanethiol.

The obtained target compound was subjected to $^1$H-NMR (CDCl$_3$; TMS standard) and infrared spectrometry. The results of analysis, and the chemical structure and measured melting point of the compound are shown in Table II-1.

Example II-16
Synthesis of 4-chloro-5-[3-(2-methylphenyl)thio-1-oxocyclohexan-2-yl]carbonyl-2,3-dihydrobenzothiophene-1,1-dioxide [Compound No. B-16]

The target compound was prepared in the same manner as described in Example II-2, except that 2-methylbenzenethiol was used instead of ethanethiol.

The obtained target compound was subjected to $^1$H-NMR (CDCl$_3$; TMS standard) and infrared spectrometry. The results of analysis, and the chemical structure and measured melting point of the compound are shown in Table II-1.

Example II-17
Synthesis of 4-chloro-5-[3-(2-chlorophenyl)thio-1-oxocyclohexan-2-yl]carbonyl-2,3-dihydrobenzothiophene-1,1-dioxide [Compound No. B-17]

The target compound was prepared in the same manner as described in Example II-2, except that 2-chlorobenzenethiol was used instead of ethanethiol.

The obtained target compound was subjected to $^1$H-NMR (CDCl$_3$; TMS standard) and infrared spectrometry. The results of analysis, and the chemical structure and measured melting point of the compound are shown in Table II-1.

Example II-18
Synthesis of 4-chloro-5-[3-(2-isopropylphenyl)thio-1-oxocyclohexan-2-yl]carbonyl-2,3-dihydrobenzothiophene-1,1-dioxide [Compound No. B-18]

The target compound was prepared in the same manner as described in Example II-2, except that 2-(2-propyl)benzenethiol was used instead of ethanethiol.

The obtained target compound was subjected to $^1$H-NMR (CDCl$_3$; TMS standard) and infrared spectrometry. The results of analysis, and the chemical structure and measured melting point of the compound are shown in Table II-1.

Example II-19
Synthesis of 4-chloro-5-[3-(2-methoxycarbonylphenyl)thio-1-oxocyclohexan-2-yl]carbonyl-2,3-dihydrobenzothiophene-1,1-dioxide [Compound No. B-19]

The target compound was prepared in the same manner as described in Example II-2, except that 2-methoxycarbonylbenzenethiol was used instead of ethanethiol.

The obtained target compound was subjected to $^1$H-NMR (CDCl$_3$; TMS standard) and infrared spectrometry. The results of analysis, and the chemical structure and measured melting point of the compound are shown in Table II-1.

Example II-20
Synthesis of 4-chloro-5-[3-(4-methoxyphenyl)thio-1-oxocyclohexan-2-yl]carbonyl-2,3-dihydrobenzothiophene-1,1-dioxide [Compound No. B-20]

The target compound was prepared in the same manner as described in Example II-2, except that 4-methoxybenzenethiol was used instead of ethanethiol.

The obtained target compound was subjected to $^1$H-NMR (CDCl$_3$; TMS standard) and infrared spectrometry. The results of analysis, and the chemical structure and measured melting point of the compound are shown in Table II-1.

Example II-21
Synthesis of 4-chloro-5-[3-(4-bromophenyl)thio-1-oxocyclohexan-2-yl]carbonyl-2,3-dihydrobenzothiophene-1,1-dioxide [Compound No. B-21]

The target compound was prepared in the same manner as described in Example II-2, except that 4-bromobenzenethiol was used instead of ethanethiol.

The obtained target compound was subjected to $^1$H-NMR (CDCl$_3$; TMS standard) and infrared spectrometry. The results of analysis, and the chemical structure and measured melting point of the compound are shown in Table II-1.

Example II-22
Synthesis of 4-chloro-5-[3-(3-propenyl)thio-1-oxocyclohexan-2-yl]carbonyl-2,3-dihydrobenzothiophene-1,1-dioxide [Compound No. B-22]

The target compound was prepared in the same manner as described in Example II-2, except that 3-propenylthiol was used instead of ethanethiol.

The obtained target compound was subjected to $^1$H-NMR (CDCl$_3$; TMS standard) and infrared spectrometry. The results of analysis, and the chemical structure and measured melting point of the compound are shown in Table II-1.

Example II-23
Synthesis of 4-chloro-5-[3-(2-methyl-2-propyl)thio-1-oxocyclohexan-2-yl]carbonyl-2,3-dihydrobenzothiophene-1,1-dioxide [Compound No. B-23]

The target compound was prepared in the same manner as described in Example II-2, except that 2-(2-methylpropane)thiol was used instead of ethanethiol.

The obtained target compound was subjected to $^1$H-NMR (CDCl$_3$; TMS standard) and infrared spectrometry. The results of analysis, and the chemical structure and measured melting point of the compound are shown in Table II-1.

Example II-24
Synthesis of 4-chloro-5-(3-methylsulfonyl-1-oxocyclohexan-2-yl)carbonyl-2,3-dihydrobenzothiophene-1,1-dioxide [Compound No. B-24]

4–Chloro-5-(3-methylthio-1-oxocyclohexan-2-yl)carbonyl-2,3-dihydrobenzothiophene-1,1-dioxide (0.80 g) was dissolved in dichloromethane (8 ml) and to the resultant solution, m-chlorobenzoic acid (1.0 g) was added at room temperature, followed by allowing to stand overnight.

The resultant mixture was diluted with methylene chloride and filtered. The filtrate was washed with a 5% aqueous solution of sodium sulfite, a 5% aqueous solution of potassium carbonate, and aqueous saturated brine, and dried over anhydrous sodium sulfate. After the filtration of the drying agent, the filtered was concentrated to thereby obtain 4-chloro-5-(3-methylsulfonyl-1-oxocyclohexan-2-yl) carbonyl-2,3-dihydrobenzothiophene-1,1-dioxide (0.76 g, yield: 87%).

The obtained target compound was subjected to $^1$H-NMR (CDCl$_3$; TMS standard) and infrared spectrometry. The results of analysis, and the chemical structure and measured melting point of the compound are shown in Table II-1.

Example II-25
Synthesis of 4-chloro-5-(3-chloro-5-methyl-1-oxocyclohexan-2-yl)carbonyl-2,3-dihydrobenzothiophene-1,1-dioxide [Compound No. B-25]

The target compound was prepared in the same manner as described in Example II-1, except that 4-chloro-5-(5-methyl-1,3-dioxocyclohexan-2-yl)carbonyl-2,3-dihydrobenzothiophene-1,1-dioxide was used instead of 4-chloro-5-(1,3-dioxocyclohexan-2-yl)carbonyl-2,3-dihydrobenzothiophene-1,1-dioxide.

The obtained target compound was subjected to $^1$H-NMR (CDCl$_3$; TMS standard) and infrared spectrometry. The results of analysis, and the chemical structure and measured melting point of the compound are shown in Table II-1.

Example II-26
Synthesis of 4-chloro-5-(3-phenylthio-5-methyl-1-oxocyclohexan-2-yl)carbonyl-2,3-dihydrobenzothiophene-1,1-dioxide [Compound No. B-26]

The target compound was prepared in the same manner as described in Example II-2, except that 4-chloro-5-(3-chloro-5-methyl-1-oxocyclohexan-2-yl)carbonyl-2,3-dihydrobenzothiophene-1,1-dioxide and benzenethiol were used instead of 4-chloro-5-(3-chloro-1-oxocyclohexan-2-yl)carbonyl-2,3-dihydrobenzothiophene-1,1-dioxide and ethanethiol, respectively.

The obtained target compound was subjected to $^1$H-NMR (CDCl$_3$; TMS standard) and infrared spectrometry. The results of analysis, and the chemical structure and measured melting point of the compound are shown in Table II-1.

Example II-27
Synthesis of 4-chloro-5-(3-ethylsulfonyl-1-oxocyclohexan-2-yl)carbonyl-2,3-dihydrobenzothiophene-1,1-dioxide [Compound No. B-27]

The target compound was prepared in the same manner as described in Example II-24, except that 4-chloro-5-(3-ethylthio-1-oxocyclohexan-2-yl)carbonyl-2,3-dihydrobenzothiophene-1,1-dioxide was used instead of 4-chloro-5-(3-methylthio-1-oxocyclohexan-2-yl)carbonyl-2,3-dihydrobenzothiophene-1,1-dioxide.

The obtained target compound was subjected to $^1$H-NMR (CDCl$_3$; TMS standard) and infrared spectrometry. The results of analysis, and the chemical structure and measured melting point of the compound are shown in Table II-1.

Example II-28
Synthesis of 4-chloro-5-[3-(3-propyl)sulfonyl-1-oxocyclohexan-2-yl]carbonyl-2,3-dihydrobenzothiophene-1,1-dioxide [Compound No. B-28]

The target compound was prepared in the same manner as described in Example II-24, except that 4-chloro-5-[3-(3-propyl)thio-1-oxocyclohexan-2-yl]carbonyl-2,3-dihydrobenzothiophene-1,1-dioxide was used instead of 4-chloro-5-(3-methylthio-1-oxocyclohexan-2-yl)carbonyl-2,3-dihydrobenzothiophene-1,1-dioxide.

The obtained target compound was subjected to $^1$H-NMR (CDCl$_3$; TMS standard) and infrared spectrometry. The results of analysis, and the chemical structure and measured melting point of the compound are shown in Table II-1.

Example II-29
Synthesis of 4-chloro-5-(3-isopropylsulfonyl-1-oxocyclohexan-2-yl)carbonyl-2,3-dihydrobenzothiophene-1,1-dioxide [Compound No. B-29]

The target compound was prepared in the same manner as described in Example II-24, except that 4-chloro-5-(3-isopropylthio-1-oxocyclohexan-2-yl)carbonyl-2,3-dihydrobenzothiophene-1,1-dioxide was used instead of 4-chloro-5-(3-methylthio-1-oxocyclohexan-2-yl)carbonyl-2,3-dihydrobenzothiophene-1,1-dioxide.

The obtained target compound was subjected to $^1$H-NMR (CDCl$_3$; TMS standard) and infrared spectrometry. The results of analysis, and the chemical structure and measured melting point of the compound are shown in Table II-1.

Example II-30
Synthesis of 4-chloro-5-[3-(4-butyl)sulfonyl-1-oxocyclohexan-2-yl]carbonyl-2,3-dihydrobenzothiophene-1,1-dioxide [Compound No. B-30]

The target compound was prepared in the same manner as described in Example II-24, except that 4-chloro-5-[3-(4-butyl)thio-1-oxocyclohexan-2-yl]carbonyl-2,3-dihydrobenzothiophene-1,1-dioxide was used instead of 4-chloro-5-(3-methylthio-1-oxocyclohexan-2-yl)carbonyl-2,3-dihydrobenzothiophene-1,1-dioxide.

The obtained target compound was subjected to $^1$H-NMR (CDCl$_3$; TMS standard) and infrared spectrometry. The results of analysis, and the chemical structure and measured melting point of the compound are shown in Table II-1.

Example II-31
Synthesis of 4-chloro-5-(3-phenylsulfonyl-1-oxocyclohexan-2-yl)carbonyl-2,3-dihydrobenzothiophene-1,1-dioxide [Compound No. B-31]

The target compound was prepared in the same manner as described in Example II-24, except that 4-chloro-5-(3-phenylthio-1-oxocyclohexan-2-yl)carbonyl-2,3-dihydrobenzothiophene-1,1-dioxide was used instead of 4-chloro-5-(3-methylthio-1-oxocyclohexan-2-yl)carbonyl-2,3-dihydrobenzothiophene-1,1-dioxide.

The obtained target compound was subjected to $^1$H-NMR (CDCl$_3$; TMS standard) and infrared spectrometry. The results of analysis, and the chemical structure and measured melting point of the compound are shown in Table II-1.

Example II-32
Synthesis of 4-chloro-5-[3-(2-methylphenyl)sulfonyl-1-oxocyclohexan-2-yl]carbonyl-2,3-dihydrobenzothiophene-1,1-dioxide [Compound No. B-32]

The target compound was prepared in the same manner as described in Example II-24, except that 4-chloro-5-[3-(2-methylphenyl)thio-1-oxocyclohexan-2-yl]carbonyl-2,3-dihydrobenzothiophene-1,1-dioxide was used instead of 4-chloro-5-(3-methylthio-1-oxocyclohexan-2-yl)carbonyl-2,3-dihydrobenzothiophene-1,1-dioxide.

The obtained target compound was subjected to $^1$H-NMR (CDCl$_3$; TMS standard) and infrared spectrometry. The results of analysis, and the chemical structure and measured melting point of the compound are shown in Table II-1.

Example II-33
Synthesis of 4-chloro-5-[3-(3-methylphenyl)sulfonyl-1-oxocyclohexan-2-yl]carbonyl-2,3-dihydrobenzothiophene-1,1-dioxide [Compound No. B-33]

The target compound was prepared in the same manner as described in Example II-24, except that 4-chloro-5-[3-(3-methylphenyl)thio-1-oxocyclohexan-2-yl]carbonyl-2,3-dihydrobenzothiophene-1,1-dioxide was used instead of 4-chloro-5-(3-methylthio-1-oxocyclohexan-2-yl)carbonyl-2,3-dihydrobenzothiophene-1,1-dioxide.

The obtained target compound was subjected to $^1$H-NMR (CDCl$_3$; TMS standard) and infrared spectrometry. The results of analysis, and the chemical structure and measured melting point of the compound are shown in Table II-1.

Example II-34
Synthesis of 4-chloro-5-[3-(4-methylphenyl)sulfonyl-1-oxocyclohexan-2-yl]carbonyl-2,3-dihydrobenzothiophene-1,1-dioxide [Compound No. B-34]

The target compound was prepared in the same manner as described in Example II-24, except that 4-chloro-5-[3-(4-methylphenyl)thio-1-oxocyclohexan-2-yl]carbonyl-2,3-dihydrobenzothiophene-1,1-dioxide was used instead of 4-chloro-5-(3-methylthio-1-oxocyclohexan-2-yl)carbonyl-2,3-dihydrobenzothiophene-1,1-dioxide.

The obtained target compound was subjected to $^1$H-NMR (CDCl$_3$; TMS standard) and infrared spectrometry. The results of analysis, and the chemical structure and measured melting point of the compound are shown in Table II-1.

Example II-35
Synthesis of 4-chloro-5-[3-(2-chlorophenyl)sulfonyl-1-oxocyclohexan-2-yl]carbonyl-2,3-dihydrobenzothiophene-1,1-dioxide [Compound No. B-35]

The target compound was prepared in the same manner as described in Example II-24, except that 4-chloro-5-[3-(2-chlorophenyl)thio-1-oxocyclohexan-2-yl]carbonyl-2,3-dihydrobenzothiophene-1,1-dioxide was used instead of 4-chloro-5-(3-methylthio-1-oxocyclohexan-2-yl)carbonyl-2,3-dihydrobenzothiophene-1,1-dioxide.

The obtained target compound was subjected to $^1$H-NMR (CDCl$_3$; TMS standard) and infrared spectrometry. The results of analysis, and the chemical structure and measured melting point of the compound are shown in Table II-1.

Example II-36
Synthesis of 4-chloro-5-[3-(2-isopropylphenyl)sulfonyl-1-oxocyclohexan-2-yl]carbonyl-2,3-dihydrobenzothiophene-1,1-dioxide [Compound No. B-36]

The target compound was prepared in the same manner as described in Example II-24, except that 4-chloro-5-[3-(2-isopropylphenyl)thio-1-oxocyclohexan-2-yl]carbonyl-2,3-dihydrobenzothiophene-1,1-dioxide was used instead of 4-chloro-5-(3-methylthio-1-oxocyclohexan-2-yl)carbonyl-2,3-dihydrobenzothiophene-1,1-dioxide.

The obtained target compound was subjected to $^1$H-NMR (CDCl$_3$; TMS standard) and infrared spectrometry. The results of analysis, and the chemical structure and measured melting point of the compound are shown in Table II-1.

Example II-37
Synthesis of 4-chloro-5-[3-(4-methoxyphenyl)sulfonyl-1-oxocyclohexan-2-yl]carbonyl-2,3-dihydrobenzothiophene-1,1-dioxide [Compound No. B-37]

The target compound was prepared in the same manner as described in Example II-24, except that 4-chloro-5-[3-(4-methoxyphenyl)thio-1-oxocyclohexan-2-yl]carbonyl-2,3-dihydrobenzothiophene-1,1-dioxide was used instead of 4-chloro-5-(3-methylthio-1-oxocyclohexan-2-yl)carbonyl-2,3-dihydrobenzothiophene-1,1-dioxide.

The obtained target compound was subjected to $^1$H-NMR (CDCl$_3$; TMS standard) and infrared spectrometry. The results of analysis, and the chemical structure and measured melting point of the compound are shown in Table II-1.

Example II-38
Synthesis of 4-chloro-5-[3-(3-propenyl)sulfonyl-1-oxocyclohexan-2-yl]carbonyl-2,3-dihydrobenzothiophene-1,1-dioxide [Compound No. B-38]

The target compound was prepared in the same manner as described in Example II-24, except that 4-chloro-5-[3-(3-propenyl)thio-1-oxocyclohexan-2-yl]carbonyl-2,3-dihydrobenzothiophene-1,1-dioxide was used instead of 4-chloro-5-(3-methylthio-1-oxocyclohexan-2-yl)carbonyl-2,3-dihydrobenzothiophene-1,1-dioxide.

The obtained target compound was subjected to $^1$H-NMR (CDCl$_3$; TMS standard) and infrared spectrometry. The results of analysis, and the chemical structure and measured melting point of the compound are shown in Table II-1.

Example II-39
Synthesis of 4-chloro-5-[3-(2-methyl-2-propyl)sulfonyl-1-oxocyclohexan-2-yl]carbonyl-2,3-dihydrobenzothiophene-1,1-dioxide [Compound No. B-39]

The target compound was prepared in the same manner as described in Example II-24, except that 4-chloro-5-[3-(2-methyl-2-propyl)thio-1-oxocyclohexan-2-yl]carbonyl-2,3-dihydrobenzothiophene-1,1-dioxide was used instead of 4-chloro-5-(3-methylthio-1-oxocyclohexan-2-yl)carbonyl-2,3-dihydrobenzothiophene-1,1-dioxide.

The obtained target compound was subjected to $^1$H-NMR (CDCl$_3$; TMS standard) and infrared spectrometry. The results of analysis, and the chemical structure and measured melting point of the compound are shown in Table II-1.

Example II-40
Synthesis of 4-chloro-5-(3-benzylsulfonyl-1-oxocyclohexan-2-yl)carbonyl-2,3-dihydrobenzothiophene-1,1-dioxide [Compound No. B-40]

The target compound was prepared in the same manner as described in Example II-24, except that 4-chloro-5-(3-benzylthio-1-oxocyclohexan-2-yl)carbonyl-2,3-dihydrobenzothiophene-1,1-dioxide was used instead of 4-chloro-5-(3-methylthio-1-oxocyclohexan-2-yl)carbonyl-2,3-dihydrobenzothiophene-1,1-dioxide.

The obtained target compound was subjected to $^1$H-NMR (CDCl$_3$; TMS standard) and infrared spectrometry. The results of analysis, and the chemical structure and measured melting point of the compound are shown in Table II-1.

Example II-41
Synthesis of 4-chloro-5-[3-(4-hydroxyphenyl)thio-1-oxocyclohexan-2-yl]carbonyl-2,3-dihydrobenzothiophene-1,1-dioxide [Compound No. B-41]

The target compound was prepared in the same manner as described in Example II-2, except that 4-hydroxybenzenethiol was used instead of ethanethiol.

The obtained target compound was subjected to $^1$H-NMR (CDCl$_3$; TMS standard) and infrared spectrometry. The results of analysis, and the chemical structure and measured melting point of the compound are shown in Table II-1.

Example II-42
Synthesis of 4-chloro-5-[3-(4-bromophenyl)sulfonyl-1-oxocyclohexan-2-yl]carbonyl-2,3-dihydrobenzothiophene-1,1-dioxide [Compound No. B-42]

The target compound was prepared in the same manner as described in Example II-24, except that 4-chloro-5-[3-(4-bromophenyl)thio-1-oxocyclohexan-2-yl]carbonyl-2,3-dihydrobenzothiophene-1,1-dioxide was used instead of 4-chloro-5-(3-methylthio-1-oxocyclohexan-2-yl)carbonyl-2,3-dihydrobenzothiophene-1,1-dioxide.

The obtained target compound was subjected to $^1$H-NMR (CDCl$_3$; TMS standard) and infrared spectrometry. The results of analysis, and the chemical structure and measured melting point of the compound are shown in Table II-1.

Example II-43
Synthesis of 4-chloro-5-[3-(4-hydroxyphenyl)sulfonyl-1-oxocyclohexan-2-yl]carbonyl-2,3-dihydrobenzothiophene-1,1-dioxide [Compound No. B-43]

The target compound was prepared in the same manner as described in Example II-24, except that 4-chloro-5-[3-(4-hydroxyphenyl)thio-1-oxocyclohexan-2-yl]carbonyl-2,3-dihydrobenzothiophene-1,1-dioxide was used instead of 4-chloro-5-(3-methylthio-1-oxocyclohexan-2-yl)carbonyl-2,3-dihydrobenzothiophene-1,1-dioxide.

The obtained target compound was subjected to $^1$H-NMR (CDCl$_3$; TMS standard) and infrared spectrometry. The results of analysis, and the chemical structure and measured melting point of the compound are shown in Table II-1.

Example II-44
Synthesis of 4-chloro-5-[3-(2-methoxycarbonylphenyl)sulfonyl-1-oxocyclohexan-2-yl]carbonyl-2,3-dihydrobenzothiophene-1,1-dioxide [Compound No. B-44]

The target compound was prepared in the same manner as described in Example II-24, except that 4-chloro-5-[3-(2-methoxycarbonylphenyl)thio-1-oxocyclohexan-2-yl]carbonyl-2,3-dihydrobenzothiophene-1,1-dioxide was used instead of 4-chloro-5-(3-methylthio-1-oxocyclohexan-2-yl)carbonyl-2,3-dihydrobenzothiophene-1,1-dioxide.

The obtained target compound was subjected to $^1$H-NMR (CDCl$_3$; TMS standard) and infrared spectrometry. The results of analysis, and the chemical structure and measured melting point of the compound are shown in Table II-1.

Example II-45
Synthesis of 4-chloro-5-[3-(4-acetylphenyl)thio-1-oxocyclohexan-2-yl]carbonyl-2,3-dihydrobenzothiophene-1,1-dioxide [Compound No. B-45]

The target compound was prepared in the same manner as described in Example II-2, except that 4-acetylbenzenethiol was used instead of ethanethiol.

The obtained target compound was subjected to $^1$H-NMR (CDCl$_3$; TMS standard) and infrared spectrometry. The results of analysis, and the chemical structure and measured melting point of the compound are shown in Table II-1.

Example II-46
Synthesis of 4-chloro-5-[3-(4-acetylphenyl)sulfonyl-1-oxocyclohexan-2-yl]carbonyl-2,3-dihydrobenzothiophene-1,1-dioxide [Compound No. B-46]

The target compound was prepared in the same manner as described in Example II-24, except that 4-chloro-5-[3-(4-acetylphenyl)thio-1-oxocyclohexan-2-yl]carbonyl-2,3-dihydrobenzothiophene-1,1-dioxide was used instead of 4-chloro-5-(3-methylthio-1-oxocyclohexan-2-yl)carbonyl-2,3-dihydrobenzothiophene-1,1-dioxide.

The obtained target compound was subjected to $^1$H-NMR (CDCl$_3$; TMS standard) and infrared spectrometry. The results of analysis, and the chemical structure and measured melting point of the compound are shown in Table II-1.

Example II-47
Synthesis of 4-methyl-5-(3-chloro-1-oxocyclohexan-2-yl)carbonyl-2,3-dihydrobenzothiophene-1,1-dioxide [Compound No. B-47]

The target compound was prepared in the same manner as described in Example II-1, except that 4-methyl-5-(1,3-dioxocyclohexan-2-yl)carbonyl-2,3-dihydrobenzothiophene-1,1-dioxide was used instead of 4-chloro-5-(1,3- dioxocyclohexan-2-yl)carbonyl-2,3-dihydrobenzo-
thiophene-1,1-dioxide.

The obtained target compound was subjected to $^1$H-NMR (CDCl$_3$; TMS standard) and infrared spectrometry. The results of analysis, and the chemical structure and measured melting point of the compound are shown in Table II-1.

Example II-48

Synthesis of 4-chloro-5-[3-(2-hydroxyphenyl)thio-1-oxocyclohexan-2-yl]carbonyl-2,3-dihydrobenzothiophene-1,1-dioxide [Compound No. B-48]

The target compound was prepared in the same manner as described in Example II-2, except that 2-hydroxybenzenethiol was used instead of ethanethiol.

The obtained target compound was subjected to $^1$H-NMR (CDCl$_3$; TMS standard) and infrared spectrometry. The results of analysis, and the chemical structure and measured melting point of the compound are shown in Table II-1.

Example II-49

Synthesis of 4-chloro-5-[3-(2-hydroxyphenyl)sulfonyl-1-oxocyclohexan-2-yl]carbonyl-2,3-dihydrobenzothiophene-1,1-dioxide [Compound No. B-49]

The target compound was prepared in the same manner as described in Example II-24, except that 4-chloro-5-[3-(2-hydroxyphenyl)thio-1-oxocyclohexan-2-yl]carbonyl-2,3-dihydrobenzothiophene-1,1-dioxide was used instead of 4-chloro-5-(3-methylthio-1-oxocyclohexan-2-yl)carbonyl-2,3-dihydrobenzothiophene-1,1-dioxide.

The obtained target compound was subjected to $^1$H-NMR (CDCl$_3$; TMS standard) and infrared spectrometry. The results of analysis, and the chemical structure and measured melting point of the compound are shown in Table II-1.

Example II-50

Synthesis of 4-methyl-5-(3-ethoxy-1-oxocyclohexan-2-yl) carbonyl-2,3-dihydrobenzothiophene-1,1-dioxide [Compound No. B-50]

4–Chloro-5-(1,3-dioxocyclohexan-2-yl)carbonyl-2,3-dihydrobenzothiophene-1,1-dioxide (1.7 g) was dissolved in methylene chloride (17 ml). Diethylaminosulfate trifluoride (1.03 ml) was added to the resultant solution under cooling with ice, followed by reaction with stirring for 1 hour at room temperature. To the resultant reaction mixture, ethanol (2 ml) was added, and reaction was allowed to proceed for one hour with stirring.

The resultant mixture was diluted with methylene chloride, washed with aqueous saturated sodium bicarbonate solution, and dried over anhydrous sodium sulfate. After the desiccant was removed through filtration and the solvent was evaporated, the crude product was recrystallized from methanol to thereby obtain 4-methyl-5-(3-ethoxy-1-oxocyclohexan-2-yl)carbonyl-2,3-dihydrobenzothiophene-1,1-dioxide (0.15 g, yield: 59%).

The obtained target compound was subjected to $^1$H-NMR (CDCl$_3$; TMS standard) and infrared spectrometry. The results of analysis, and the chemical structure and measured melting point of the compound are shown in Table II-1.

Example II-51

Synthesis of 4-methyl-5-(3-isopropyloxy-1-oxocyclohexan-2-yl)carbonyl-2,3-dihydrobenzothiophene-1,1-dioxide [Compound No. B-51]

The target compound was prepared in the same manner as described in Example II-50, except that isopropanol was used instead of ethanol.

The obtained target compound was subjected to $^1$H-NMR (CDCl$_3$; TMS standard) and infrared spectrometry. The results of analysis, and the chemical structure and measured melting point of the compound are shown in Table II-1.

Example II-52

Synthesis of 4-methyl-5-(3-methoxy-1-oxocyclohexan-2-yl) carbonyl-2,3-dihydrobenzothiophene-1,1-dioxide [Compound No. B-52]

The target compound was prepared in the same manner as described in Example II-50, except that methanol was used instead of ethanol.

The obtained target compound was subjected to $^1$H-NMR (CDCl$_3$; TMS standard) and infrared spectrometry. The results of analysis, and the chemical structure and measured melting point of the compound are shown in Table II-1.

Example II-53

Synthesis of 4-chloro-5-[3-(2-methoxyethoxy)-1-oxocyclohexan-2-yl]carbonyl-2,3-dihydrobenzothiophene-1,1-dioxide [Compound No. B-53]

The target compound was prepared in the same manner as described in Example II-50, except that 2-methoxyethanol was used instead of ethanol.

The obtained target compound was subjected to $^1$H-NMR (CDCl$_3$; TMS standard) and infrared spectrometry. The results of analysis, and the chemical structure and measured melting point of the compound are shown in Table II-1.

Example II-54

Synthesis of 4-methoxyimino-5,8-dimethyl-6-(3-chloro-1-oxocyclohexan-2-yl)carbonylthiochroman-1,1–1,1-dioxide [Compound No. B-54]

The target compound was prepared in the same manner as described in Example II-1, except that 4-methoxyimino-5,8-dimethyl-6-(1,3-dioxocyclohexan-2-yl)carbonyl-thiochroman-1,1-dioxide was used instead of 4-chloro-5-(1,3-dioxocyclohexan-2-yl)carbonyl-2,3-dihydrobenzothiophene-1,1-dioxide.

The obtained target compound was subjected to $^1$H-NMR (CDCl$_3$; TMS standard) and infrared spectrometry. The results of analysis, and the chemical structure and measured melting point of the compound are shown in Table II-1.

Example II-55

Synthesis of 4-methoxyimino-5,8-dimethyl-6-(3-dimethylamino-1-oxocyclohexan-2-yl)carbonylthio-chroman-1,1-1,1-dioxide [Compound No. B-55]

The target compound was prepared in the same manner as described in Example II-12, except that 4-methoxyimino-5,8-dimethyl-6-(3-chloro-1-oxocyclohexan-2-yl) carbonylthiochroman-1,1-dioxide and dimethylamine hydrochloride were used instead of 4-chloro-5-(1,3-dioxocyclohexan-2-yl)carbonyl-2,3-dihydrobenzo-thiophene-1,1-dioxide and N,O-dimethylhydroxylamine hydrochloride, respectively.

The obtained target compound was subjected to $^1$H-NMR (CDCl$_3$; TMS standard) and infrared spectrometry. The results of analysis, and the chemical structure and measured melting point of the compound are shown in Table II-1.

Example II-56

Synthesis of 4-methoxyimino-5,8-dimethyl-6-(3-methylthio-1-oxocyclohexan-2-yl)carbonylthiochroman-1,1-1,1-dioxide [Compound No. B-56]

The target compound was prepared in the same manner as described in Example II-2, except that 4-methoxyimino-5,8-dimethyl-6-(3-chloro-1-oxocyclohexan-2-yl) carbonylthiochroman-1,1,-dioxide and methanethiol were used instead of 4-chloro-5-(3-chloro-1-oxocyclohexan-2-yl) carbonyl-2,3-dihydrobenzothiophene-1,1-dioxide and ethanethiol, respectively.

The obtained target compound was subjected to $^1$H-NMR (CDCl$_3$; TMS standard) and infrared spectrometry. The results of analysis, and the chemical structure and measured melting point of the compound are shown in Table II-1.

Example II-57

Synthesis of 4-methoxyimino-5,8-dimethyl-6-[3-(N-methoxymethyl)amino-1-oxocyclohexan-2-yl]carbonylthiochroman-1,1-1,1-dioxide [Compound No. B-57]

The target compound was prepared in the same manner as described in Example II-12, except that 4-methoxyimino-5,8-dimethyl-6-(3-chloro-1-oxocyclohexan-2-yl) carbonylthiochroman-1,1-dioxide was used instead of 4-chloro-5-(3-chloro-1-oxocyclohexan-2-yl)carbonyl-2,3-dihydrobenzothiophene-1,1-dioxide.

The obtained target compound was subjected to $^1$H-NMR (CDCl$_3$; TMS standard) and infrared spectrometry. The results of analysis, and the chemical structure and measured melting point of the compound are shown in Table II-1.

Example II-58

Synthesis of 4-methoxyimino-5,8-dimethyl-6-[3-(4-methylphenyl)amino-1-oxocyclohexan-2-yl]carbonylthiochroman-1,1-1,1-dioxide [Compound No. B-58]

The target compound was prepared in the same manner as described in Example II-12, except that 4-methoxyimino-5,8-dimethyl-6-(3-chloro-1-oxocyclohexan-2-yl) carbonylthiochroman-1,1-dioxide and 4-methylphenylamine were used instead of 4-chloro-5-(3-chloro-1-oxocyclohexan-2-yl)carbonyl-2,3-dihydrobenzothiophene-1,1-dioxide and N,O-dimethylhydroxylamine, respectively.

The obtained target compound was subjected to $^1$H-NMR (CDCl$_3$; TMS standard) and infrared spectrometry. The results of analysis, and the chemical structure and measured melting point of the compound are shown in Table II-1.

Example II-59

Synthesis of 4-methoxyimino-5,8-dimethyl-6-[3-(4-methylphenyl)thio-1-oxocyclohexan-2-yl]carbonyl-thiochroman-1,1-1,1-dioxide [Compound No. B-59]

The target compound was prepared in the same manner as described in Example II-2, except that 4-methoxyimino-5,8-dimethyl-6-(3-chloro-1-oxocyclohexan-2-yl) carbonylthiochroman-1,1-dioxide and 4-methylbenzenethiol were used instead of 4-chloro-5-(3-chloro-1-oxocyclohexan-2-yl)carbonyl-2,3-dihydrobenzothiophene-1,1-dioxide and ethanethiol, respectively.

The obtained target compound was subjected to $^1$H-NMR (CDCl$_3$; TMS standard) and infrared spectrometry. The results of analysis, and the chemical structure and measured melting point of the compound are shown in Table II-1.

Example II-60

Synthesis of 4-methoxyimino-5,8-dimethyl-6-[3-(4-methylphenyl)sulfonyl-1-oxocyclohexan-2-yl]carbonylthiochroman-1,1-1,1-dioxide [Compound No. B-60]

The target compound was prepared in the same manner as described in Example II-24, except that 4-methoxyimino-5,8-dimethyl-6-[3-(4-methylphenyl)thio-1-oxocyclohexan-2-yl]carbonylthiochroman-1,1-dioxide was used instead of 4-chloro-5-(3-methylthio-1-oxocyclohexan-2-yl)carbonyl-2,3-dihydrobenzothiophene-1,1-dioxide.

The obtained target compound was subjected to $^1$H-NMR (CDCl$_3$; TMS standard) and infrared spectrometry. The results of analysis, and the chemical structure and measured melting point of the compound are shown in Table II-1.

Example II-61

Synthesis of 4-methoxyimino-5,8-dimethyl-6-[3-(3-propyl)thio-1-oxocyclohexan-2-yl]carbonylthiochroman-1,1-1,1-dioxide [Compound No. B-61]

The target compound was prepared in the same manner as described in Example II-2, except that 4-methoxyimino-5,8-dimethyl-6-(3-chloro-1-oxocyclohexan-2-yl) carbonylthiochroman-1,1-dioxide and 3-propanethiol were used instead of 4-chloro-5-(3-chloro-1-oxocyclohexan-2-yl)carbonyl-2,3-dihydrobenzothiophene-1,1-dioxide and ethanethiol, respectively.

The obtained target compound was subjected to $^1$H-NMR (CDCl$_3$; TMS standard) and infrared spectrometry. The results of analysis, and the chemical structure and measured melting point of the compound are shown in Table II-1.

Example II-62

Synthesis of 4-methoxyimino-5,8-dimethyl-6-[3-(3-propyl)sulfonyl-1-oxocyclohexan-2-yl]carbonylthiochroman-1,1-1,1-dioxide [Compound No. B-62]

The target compound was prepared in the same manner as described in Example II-24, except that 4-methoxyimino-5,8-dimethyl-6-[3-(3-propyl)thio-1-oxocyclohexan-2-yl]carbonylthiochroman-1,1-dioxide was used instead of 4-chloro-5-(3-methylthio-1-oxocyclohexan-2-yl)carbonyl-2,3-dihydrobenzothiophene-1,1-dioxide.

The obtained target compound was subjected to $^1$H-NMR (CDCl$_3$; TMS standard) and infrared spectrometry. The results of analysis, and the chemical structure and measured melting point of the compound are shown in Table II-1.

Example II-63

Synthesis of 3,3,5-trimethyl-6-(3-chloro-1-oxocyclohexan-2-yl)carbonylthiochroman-4-one-1,1-dioxide [Compound No. B-63]

The target compound was prepared in the same manner as described in Example II-1 except that 3,3,5-trimethyl-6-(1,3-dioxocyclohexan-2-yl)carbonylthiochroman-4-one-1,1-dioxide was used instead of 4-chloro-5-(1,3-dioxocyclohexan-2-yl)carbonyl-2,3-dihydrobenzo-thiophene-1,1-dioxide.

The obtained target compound was subjected to $^1$H-NMR (CDCl$_3$; TMS standard) and infrared spectrometry. The results of analysis, and the chemical structure and measured melting point of the compound are shown in Table II-1.

Example II-64

Synthesis of 3,3,5-trimethyl-6-[3-(4-chloro)thio-1-oxocyclohexan-2-yl]carbonylthiochroman-4-one-1,1-dioxide [Compound No. B-64]

The target compound was prepared in the same manner as described in Example II-2 except that 3,3,5-trimethyl-6-(3-chloro-1-oxocyclohexan-2-yl)carbonylthiochroman-4-one-1,1-dioxide and 4-chlorobenzenethiol were used instead of 4-chloro-5-(3-chloro-1-oxocyclohexan-2-yl)carbonyl-2,3-dihydrobenzothiophene-1,1-dioxide and ethanethiol, respectively.

The obtained target compound was subjected to $^1$H-NMR (CDCl$_3$; TMS standard) and infrared spectrometry. The results of analysis, and the chemical structure and measured melting

Example II-65
Synthesis of 4-methoxyimino-5,6-dimethyl-6-[3-(4-chlorophenyl)sulfonyl-1-oxocyclohexan-2-yl]carbonylthiochroman-4-one-1,1-dioxide [Compound No. B-65]

The target compound was prepared in the same manner as described in Example II-24 except that 4-methoxyimino-5,8-dimethyl-6-[3-(4-chlorophenyl)thio-1-oxocyclohexan-2-yl]carbonylthiochroman-4-one-1,1-dioxide was used instead of 4-chloro-5-(3-methylthio-1-oxocyclohexan-2-yl)carbonyl-2,3-dihydrobenzothiophene-1,1-dioxide.

The obtained target compound was subjected to $^1$H-NMR (CDCl$_3$; TMS standard) and infrared spectrometry. The results of analysis, and the chemical structure and measured melting point of the compound are shown in Table II-1.

Example II-66
Synthesis of 4-(2-propyl)oxy-5,8-dimethyl-6-(3-chloro-1-oxocyclohexan-2-yl)carbonylthiochroman-1,1-dioxide [Compound No. B-66]

The target compound was prepared in the same manner as described in Example II-1 except that 4-(2-propyl)oxy-5,8-dimethyl-6-(1,3-dioxocyclohexan-2-yl)carbonylthiochroman-1,1-dioxide was used instead of 4-chloro-5-(1,3-dioxocyclohexan-2-yl)carbonyl-2,3-dihydrobenzothiophene-1,l-dioxide.

The obtained target compound was subjected to $^1$H-NMR (CDCl$_3$; TMS standard) and infrared spectrometry. The results of analysis, and the chemical structure and measured melting point of the compound are shown in Table II-1. point of the compound are shown in Table II-1.

Example II-67
Synthesis of 4-(2-propyl)oxy-5,8-dimethyl-6-(3-methylthio-1-oxocyclohexan-2-yl)carbonylthiochroman-1,1-dioxide [Compound No. B-67]

The target compound was prepared in the same manner as described in Example II-2 except that 4-(2-propyl)oxy-5,8-dimethyl-6-(3-chloro-1-oxocyclohexan-2-yl)carbonylthiochroman-1,1-dioxide and methanethiol were used instead of 4-chloro-5-(3-chloro-1-oxocyclohexan-2-yl)carbonyl-2,3-dihydrobenzothiophene-1,1-dioxide and ethanethiol, respectively.

The obtained target compound was subjected to $^1$H-NMR (CDCl$_3$; TMS standard) and infrared spectrometry. The results of analysis, and the chemical structure and measured melting point of the compound are shown in Table II-1.

Example II-68
Synthesis of 4-(2-propyl)oxy-5,8-dimethyl-6-(3-phenylthio-1-oxocyclohexan-2-yl)carbonylthiochroman-1,1-dioxide [Compound No. B-68]

The target compound was prepared in the same manner as described in Example II-2 except that 4-(2-propyl)oxy-5,8-dimethyl-6-(3-chloro-1-oxocyclohexan-2-yl)carbonylthiochroman-1,1-dioxide and benzenethiol were used instead of 4-chloro-5-(3-chloro-1-oxocyclohexan-2-yl)carbonyl-2,3-dihydrobenzothiophene-1,1-dioxide and ethanethiol, respectively.

The obtained target compound was subjected to $^1$H-NMR (CDCl$_3$; TMS standard) and infrared spectrometry. The results of analysis, and the chemical structure and measured melting point of the compound are shown in Table II-1.

Example II-69
Synthesis of 4-(2-propyl)oxy-5,8-dimethyl-6-(3-methylsulfonyl-1-oxocyclohexan-2-yl)carbonylthiochroman-1,1-dioxide [Compound No. B-69]

The target compound was prepared in the same manner as described in Example II-24 except that 4-(2-propyl)oxy-5,8-dimethyl-6-(3-methylthio-1-oxocyclohexan-2-yl)carbonylthiochroman-1,1-dioxide was used instead of 4-chloro-5-(3-methylthio-1-oxocyclohexan-2-yl)carbonyl-2,3-dihydrobenzothiophene-1,1-dioxide.

The obtained target compound was subjected to $^1$H-NMR (CDCl$_3$; TMS standard) and infrared spectrometry. The results of analysis, and the chemical structure and measured melting point of the compound are shown in Table II-1.

Example II-70
Synthesis of 4-(2-propyl)oxy-5,8-dimethyl-6-(3-benzylthio-1-oxocyclohexan-2-yl)carbonylthiochroman-1,1-dioxide [Compound No. B-70]

The target compound was prepared in the same manner as described in Example II-2 except that 4-(2-propyl)oxy-5,8-dimethyl-6-(3-chloro-1-oxocyclohexan-2-yl)carbonylthiochroman-1,1-dioxide and benzylthiol were used instead of 4-chloro-5-(3-chloro-1-oxocyclohexan-2-yl)carbonyl-2,3-dihydrobenzothiophene-1,1-dioxide and ethanethiol, respectively.

The obtained target compound was subjected to $^1$H-NMR (CDCl$_3$; TMS standard) and infrared spectrometry. The results of analysis, and the chemical structure and measured melting point of the compound are shown in Table II-1.

Example II-71
Synthesis of 4-(2-propyl)oxy-5,8-dimethyl-6-(3-benzylsulfonyl-1-oxocyclohexan-2-yl)carbonylthiochroman-1,1-dioxide [Compound No. B-71]

The target compound was prepared in the same manner as described in Example II-24 except that 4-(2-propyl)oxy-5,8-dimethyl-6-(3-benzylthio-1-oxocyclohexan-2-yl)carbonylthiochroman-1,1-dioxide was used instead of 4-chloro-5-(3-methylthio-1-oxocyclohexan-2-yl)carbonyl-2,3-dihydrobenzothiophene-1,1-dioxide.

The obtained target compound was subjected to $^1$H-NMR (CDCl$_3$; TMS standard) and infrared spectrometry. The results of analysis, and the chemical structure and measured melting point of the compound are shown in Table II-1.

Example II-72
Synthesis of 4-methoxyimino-5-methyl-6-(3-chloro-1-oxocyclohexan-2-yl)carbonylthiochroman-1,1-dioxide [Compound No. B-72]

The target compound was prepared in the same manner as described in Example II-1 except that 4-methoxyimino-5-methyl-6-(1,3-dioxocyclohexan-2-yl)carbonylthiochroman-1,1-dioxide was used instead of 4-chloro-5-(1,3-dioxocyclohexan-2-yl)carbonyl-2,3-dihydrobenzothiophene-1,1-dioxide.

The obtained target compound was subjected to $^1$H-NMR (CDCl$_3$; TMS standard) and infrared spectrometry. The results of analysis, and the chemical structure and measured melting point of the compound are shown in Table II-1.

Example II-73
Synthesis of 4-methoxyimino-5-methyl-6-(3-methylthio-1-oxocyclohexan-2-yl)carbonylthiochroman-1,1-dioxide [Compound No. B-73]

The target compound was prepared in the same manner as described in Example II-2 except that 4-methoxyimino-5-methyl-6-(3-chloro-1-oxocyclohexan-2-yl)

carbonylthiochroman-1,1-dioxide and methanethiol were used instead of 4-chloro-5-(3-chloro-1-oxocyclohexan-2-yl) carbonyl-2,3-dihydrobenzothiophene-1,1-dioxide and ethanethiol, respectively.

The obtained target compound was subjected to $^1$H-NMR (CDCl$_3$; TMS standard) and infrared spectrometry. The results of analysis, and the chemical structure and measured melting point of the compound are shown in Table II-1.

Example II-74

Synthesis of 4-methoxyimino-5-methyl-6-(3-phenylthio-1-oxocyclohexan-2-yl)carbonylthiochroman-1,1-dioxide [Compound No. B-74]

The target compound was prepared in the same manner as described in Example II-2 except that 4-methoxyimino-5-methyl-6-(3-chloro-1-oxocyclohexan-2-yl) carbonylthiochroman-1,1-dioxide and benzenethiol were used instead of 4-chloro-5-(3-chloro-1-oxocyclohexan-2-yl) carbonyl-2,3-dihydrobenzothiophene-1,1-dioxide and ethanethiol, respectively.

The obtained target compound was subjected to $^1$H-NMR (CDCl$_3$; TMS standard) and infrared spectrometry. The results of analysis, and the chemical structure and measured melting point of the compound are shown in Table II-1.

Example II-75

Synthesis of 4-methoxyimino-5-methyl-6-(3-phenylsulfonyl-1-oxocyclohexan-2-yl)carbonylthiochroman-1,1-dioxide [Compound No. B-75]

The target compound was prepared in the same manner as described in Example II-24 except that 4-methoxyimino-5-methyl-6-(3-phenylthio-1-oxocyclohexan-2-yl) carbonylthiochroman-1,1-dioxide was used instead of 4-chloro-5-(3-methylthio-1-oxocyclohexan-2-yl)carbonyl-2,3-dihydrobenzothiophene-1,1-dioxide.

The obtained target compound was subjected to $^1$H-NMR (CDCl$_3$; TMS standard) and infrared spectrometry. The results of analysis, and the chemical structure and measured melting point of the compound are shown in Table II-1.

Example II-76

Synthesis of 4-methoxyimino-5-methyl-6-[3-(N-methoxymethyl)amino-1-oxocyclohexan-2-yl] carbonylthiochroman-1,1-dioxide [Compound No. B-76]

The target compound was prepared in the same manner as described in Example II-12 except that 4-methoxyimino-5-methyl-6-(3-chloro-1-oxocyclohexan-2-yl) carbonylthiochroman-1,1-dioxide was used instead of 4-chloro-5-(3-chloro-1-oxocyclohexan-2-yl)carbonyl-2,3-dihydrobenzothiophene-1,1-dioxide.

The obtained target compound was subjected to $^1$H-NMR (CDCl$_3$; TMS standard) and infrared spectrometry. The results of analysis, and the chemical structure and measured melting point of the compound are shown in Table II-1.

Example II-77

Synthesis of 5-chloro-6-(3-chloro-1-oxocyclohexan-2-yl) carbonylthiochroman-1,1-dioxide [Compound No. B-77]

The target compound was prepared in the same manner as described in Example II-1 except that 5-chloro-6-(1,3-dioxocyclohexan-2-yl)carbonylthiochroman-1,1-dioxide was used instead of 4-chloro-5-(1,3-dioxocyclohexan-2-yl) carbonyl-2,3-dihydrobenzothiophene-1,1-dioxide.

The obtained target compound was subjected to $^1$H-NMR (CDCl$_3$; TMS standard) and infrared spectrometry. The results of analysis, and the chemical structure and measured melting point of the compound are shown in Table II-1.

Example II-78

Synthesis of 5-chloro-6-(3-phenylthio-1-oxocyclohexan-2-yl)carbonylthiochroman-1,1-dioxide [Compound No. B-78]

The target compound was prepared in the same manner as described in Example II-2 except that 5-chloro-6-(3-chloro-1-oxocyclohexan-2-yl)carbonylthiochroman-1,1-dioxide and benzenethiol were used instead of 4-chloro-5-(3-chloro-1-oxocyclohexan-2-yl)carbonyl-2,3-dihydrobenzothiophene-1,1-dioxide and ethanethiol.

The obtained target compound was subjected to $^1$H-NMR (CDCl$_3$; TMS standard) and infrared spectrometry. The results of analysis, and the chemical structure and measured melting point of the compound are shown in Table II-1.

Example II-79

Synthesis of 5-chloro-6-(3-methylthio-1-oxocyclohexan-2-yl)carbonylthiochroman-1,1-dioxide [Compound No. B-79]

The target compound was prepared in the same manner as described in Example II-2 except that 5-chloro-6-(3-chloro-1-oxocyclohexan-2-yl)carbonylthiochroman-1,1-dioxide and methanethiol were used instead of 4-chloro-5-(3-chloro-1-oxocyclohexan-2-yl)carbonyl-2,3-dihydrobenzothiophene-1,1-dioxide and ethanethiol.

The obtained target compound was subjected to $^1$H-NMR (CDCl$_3$; TMS standard) and infrared spectrometry. The results of analysis, and the chemical structure and measured melting point of the compound are shown in Table II-1.

Example II-80

Synthesis of 5-chloro-6-(3-methylsulfonyl-1-oxocyclohexan-2-yl)carbonylthiochroman-1,1-dioxide [Compound No. B-80]

The target compound was prepared in the same manner as described in Example II-24 except that 5-chloro-6-(3-methylthio-1-oxocyclohexan-2-yl)carbonylthiochroman-1,1-dioxide was used instead of 4-chloro-5-(3-methylthio-1-oxocyclohexan-2-yl)carbonyl-2,3-dihydrobenzothiophene-1,1-dioxide.

The obtained target compound was subjected to $^1$H-NMR (CDCl$_3$; TMS standard) and infrared spectrometry. The results of analysis, and the chemical structure and measured melting point of the compound are shown in Table II-1.

Example II-81

Synthesis of 4-chloro-5-[3-(3-methylthio)propylthio-1-oxocyclohexan-2-yl)carbonyl-2,3-dihydrobenzothiophene-1,1-dioxide. [Compound No. B-81]

The target compound was prepared in the same manner as described in Example II-2 except that 3-methylthiopropanethiol was used instead of ethanethiol.

The obtained target compound was subjected to $^1$H-NMR (CDCl$_3$; TMS standard) and infrared spectrometry. The results of analysis, and the chemical structure and measured melting point of the compound are shown in Table II-1.

In the Table II-1, "(1)" to "(6)" indicates respectively as follows.

(1) Example No.
(2) Compound No.
(3) Chemical structure
(4) NMR/ppm (CDCl$_3$, TMS standard)
(5) Infra Red Absorption (cm$^{-1}$)
(6) Property (mp: °C.)

TABLE II-1

| (1) | (2) | (3) | (4) | (5) | (6) |
|---|---|---|---|---|---|
| II-1 | B-1 | 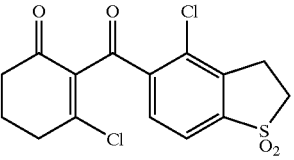 | 2.0-2.4(2H,m)<br>2.4-2.7(2H,m)<br>2.8-3.0(2H,m)<br>3.3-3.7(4H,m)<br>7.70(1H,d)<br>7.82(1H,d) | 1685<br>1605<br>1390<br>1300<br>1175<br>1125 | 83.9–<br>85.4 |
| II-2 | B-2 | 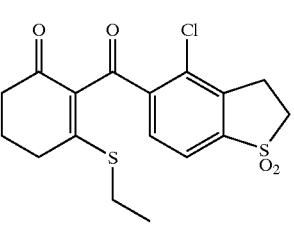 | 1.37(3H,t)<br>2.0-2.3(2H,m)<br>2.3-2.6(2H,m)<br>2.8-3.1(4H,m)<br>3.2-3.7(4H,m)<br>7.49(1H,d)<br>7.67(1H,d) | 1645<br>1395<br>1345<br>1305<br>1190<br>1120 | 129.5–<br>131.3 |
| II-3 | B-3 | 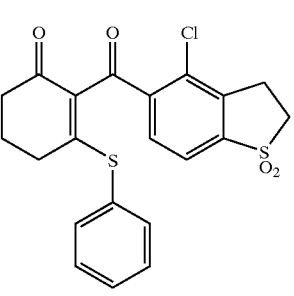 | 1.8-2.2(2H,m)<br>2.3-2.6(4H,m)<br>3.2-3.7(4H,m)<br>7.3-7.8(7H,m) | 1650<br>1490<br>1415<br>1400<br>1310<br>1185 | 203.8–<br>205.0 |
| II-4 | B-4 | 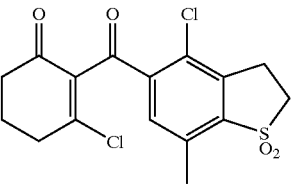 | 2.0-2.4(2H,m)<br>2.4-2.7(2H,m)<br>2.62(3H,s)<br>2.8-3.0(2H,m)<br>3.2-3.7(4H,m)<br>7.54(1H,s) | 1660<br>1610<br>1300<br>1280<br>1135<br>1120 | 169.9–<br>170.4 |
| II-5 | B-5 | 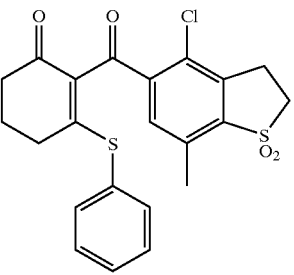 | 1.9-2.1(2H,m)<br>2.3-2.6(4H,m)<br>2.63(3H,s)<br>3.2-3.7(4H,m)<br>7.31(1H,s)<br>7.4-7.7(5H,m) | 1660<br>1640<br>1345<br>1290<br>1195<br>1125 | 261.9–<br>263.7 |
| II-6 | B-6 | 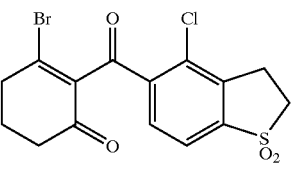 | 2.0-2.4(2H,m)<br>2.4-2.7(2H,m)<br>2.9-3.2(2H,m)<br>3.3-3.8(4H,m)<br>7.69(1H,d)<br>7.85(1H,d) | 1670<br>1615<br>1415<br>1400<br>1315<br>1290<br>1190<br>1135 | 68.4–<br>69.7 |
| II-7 | B-7 | 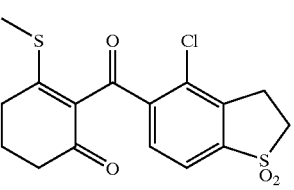 | 2.0-2.3(2H,m)<br>2.3-2.6(2H,m)<br>2.47(3H,s)<br>2.9-3.0(2H,m)<br>3.2-3.7(4H,m)<br>7.46(1H,d)<br>7.67(1H,d) | 1655<br>1615<br>1440<br>1400<br>1345<br>1295<br>1175 | 181.8–<br>182.5 |

TABLE II-1-continued

| (1) | (2) | (3) | (4) | (5) | (6) |
|---|---|---|---|---|---|
| II-8 | B-8 | | 1.06(3H,t)<br>1.5-1.9(2H,m)<br>2.0-2.5(2H,m)<br>2.5-2.6(2H,m)<br>2.8-3.1(4H,m)<br>3.2-3.7(4H,m)<br>7.49(1H,d)<br>7.67(1H,d) | 1645<br>1395<br>1345<br>1300<br>1240<br>1180 | 57–69 |
| II-9 | B-9 | | 1.39(6H,d)<br>2.0-2.3(2H,m)<br>2.3-2.6(2H,m)<br>2.8-3.1(2H,m)<br>3.2-3.8(5H,m)<br>7.54(1H,d)<br>7.68(1H,d) | 1645<br>1395<br>1345<br>1300<br>1240<br>1180 | 61–72 |
| II-10 | B-10 | | 0.95(3H,t)<br>1.2-1.9(4H,m)<br>1.9-2.5(2H,m)<br>2.5-2.6(2H,m)<br>2.8-3.1(4H,m)<br>3.2-3.7(4H,m)<br>7.49(1H,d)<br>7.67(1H,d) | 1635<br>1450<br>1390<br>1300<br>1175<br>1120 | Syrup |
| II-11 | B-11 | | 1.9-2.3(2H,m)<br>2.3-2.6(2H,m)<br>2.8-3.1(2H,m)<br>3.2-3.7(4H,m)<br>4.18(2H,s)<br>7.34(5H,s)<br>7.45(1H,d)<br>7.65(1H,d) | 1625<br>1395<br>1335<br>1290<br>1165<br>1110 | 191.5–192.1 |
| II-12 | B-12 | | 1.8-2.2(2H,m)<br>2.2-2.4(2H,m)<br>2.6-2.9(2H,m)<br>3.31(3H,s)<br>3.3-3.7(4H,m)<br>3.68(3H,s)<br>7.60(1H,d)<br>7.61(1H,d) | 1585<br>1385<br>1300<br>1175<br>1120 | 74.3-82.5 |
| II-13 | B-13 | | 1.8-2.1(2H,m)<br>2.1-2.4(2H,m)<br>2.7-2.9(2H,m)<br>3.26(6H,s)<br>3.2-3.7(4H,m)<br>7.33(1H,d)<br>7.63(1H,d) | 1585<br>1390<br>1295<br>1170<br>1115 | 175.1–175.3 |
| II-14 | B-14 | | 1.8-2.1(2H,m)<br>2.3-2.6(4H,m)<br>2.42(3H,s)<br>3.2-3.7(4H,m)<br>7.25(2H,d)<br>7.44(2H,d)<br>7.53(1H,d)<br>7.70(1H,d) | 1660<br>1630<br>1470<br>1400<br>1340<br>1310<br>1280<br>1250 | 183.3–199.5 |

TABLE II-1-continued

| (1) | (2) | (3) | (4) | (5) | (6) |
|---|---|---|---|---|---|
| II-15 | B-15 | | 1.8-2.2(2H,m)<br>2.3-2.6(4H,m)<br>2.41(3H,s)<br>3.2-3.7(4H,m)<br>7.34(4H,s)<br>7.54(1H,d)<br>7.71(1H,d) | 1640<br>1340<br>1295<br>1275<br>1245<br>1175<br>1120 | 190.2–196.6 |
| II-16 | B-16 | | 1.8-2.1(2H,m)<br>2.2-2.6(4H,m)<br>2.44(3H,m)<br>3.2-3.7(4H,m)<br>7.1-7.5(4H,m)<br>7.56(1H,d)<br>7.72(1H,d) | 1640<br>1405<br>1350<br>1340<br>1305<br>1280<br>1195<br>1125 | 198.8–199.5 |
| II-17 | B-17 | | 1.8-2.2(2H,m)<br>2.3-2.6(4H,m)<br>3.2-3.7(4H,m)<br>7.3-7.9(6H,m) | 1640<br>1495<br>1400<br>1295<br>1170<br>1110 | 190–192 |
| II-18 | B-18 | | 1.24(6H,d)<br>1.8-2.1(2H,m)<br>2.2-2.6(4H,m)<br>3.2-3.7(5H,m)<br>7.1-7.6(4H,m)<br>7.59(1H,d)<br>7.73(1H,d) | 1645<br>1470<br>1410<br>1395<br>1305<br>1175<br>1120 | 63–decop. |
| II-19 | B-19 | | 1.8-2.2(2H,m)<br>2.3-2.7(4H,m)<br>3.2-3.7(4H,m)<br>3.90(3H,s)<br>7.5-7.9(5H,m)<br>7.8-8.0(1H,m) | 1725<br>1665<br>1415<br>1290<br>1255<br>1180<br>1120 | 186 |

TABLE II-1-continued

| (1) | (2) | (3) | (4) | (5) | (6) |
|---|---|---|---|---|---|
| II-20 | B-20 | MeO-C6H4-S- (structure) | 1.8-2.1(2H,m)<br>2.3-2.6(4H,m)<br>3.3-3.7(4H,m)<br>3.86(3H,s)<br>6.96(2H,d)<br>7.46(2H,d)<br>7.34(1H,d)<br>7.70(1H,d) | 1585<br>1480<br>1400<br>1340<br>1280<br>1240<br>1170 | 117–decomp. |
| II-21 | B-21 | Br-C6H4-S- (structure) | 1.8-2.2(2H,m)<br>2.3-2.6(4H,m)<br>3.2-3.7(4H,m)<br>7.3.-<br>7.8(6H,m) | 1490<br>1420<br>1355<br>1320<br>1260<br>1180<br>1135 | 196 |
| II-22 | B-22 | allyl-S- (structure) | 1.9-2.3(2H,m)<br>2.3-2.6(2H,m)<br>2.8-3.1(2H,m)<br>3.2-3.7(6H,m)<br>5.2-5.5(2H,m)<br>5.6-6.2(1H,m)<br>7.50(1H,d)<br>7.67(1H,d) | 1630<br>1405<br>1345<br>1295<br>1175<br>1120 | |
| II-23 | B-23 | t-Bu-S- (structure) | 1.44(9H,s)<br>2.0-2.3(2H,m)<br>2.4-2.6(2H,m)<br>2.8-3.1(2H,m)<br>3.3-3.7(4H,m)<br>7.69(2H,s) | 2960<br>1660<br>1390<br>1310<br>1290<br>1175<br>1130 | 151–153 |
| II-24 | B-24 | MeSO2- (structure) | 2.1-2.4(2H,m)<br>2.5-2.7(2H,m)<br>2.8-3.0(2H,m)<br>3.09(3H,s)<br>3.3-3.7(4H,m)<br>7.72(1H,d)<br>8.09(1H,d) | 1665<br>1590<br>1390<br>1295<br>1175<br>1120 | 102–103 |
| II-25 | B-25 | Cl (structure) | 1.15(3H,d)<br>2.2-3.1(5H,m)<br>3.3-3.8(4H,m)<br>7.70(1H,d)<br>7.79(1H,d) | 1690<br>1660<br>1420<br>1310<br>1290<br>1130 | Syrup |
| II-26 | B-26 | Ph (structure) | 0.96(3H,d)<br>2.0-2.7(5H,m)<br>3.3-3.7(4H,m)<br>7.5-7.6(5H,m)<br>7.54(1H,d)<br>7.70(1H,d) | 1650<br>1530<br>1310<br>1280<br>1260<br>1240<br>1180<br>1120 | Syrup |

TABLE II-1-continued

| (1) | (2) | (3) | (4) | (5) | (6) |
|---|---|---|---|---|---|
| II-27 | B-27 | | 1.34(3H,t)<br>2.2-2.4(2H,m)<br>2.5-2.7 (2H,m)<br>2.8-3.0(2H,m)<br>3.18(2H,q)<br>.3-3.7(4H,m)<br>7.71(1H,d)<br>8.09(1H,d) | 2970<br>1730<br>1680<br>1450<br>1310<br>1280<br>1180<br>1130 | |
| II-28 | B-28 | | 1.33(3H,t)<br>2.1-2.4(4H,m)<br>2.5-2.7(2H,m)<br>2.8-3.0(2H,m)<br>3.3-3.7(6H,m)<br>7.72(1H,d)<br>8.09(1H,d) | 2980<br>1720<br>1700<br>1400<br>1310<br>1290<br>1180 | Syrup |
| II-29 | B-29 | | 1.18(6H,m)<br>1.8-2.1(2H,m)<br>2.4-2.8(3H,m)<br>3.0-3.2(2H,m)<br>3.4-3.7(4H,m)<br>7.74(1H,d)<br>8.09(1H,d) | 2970<br>1700<br>1680<br>1400<br>1320<br>1310<br>1180 | Syrup |
| II-30 | B-30 | | 1.03(3Ht)<br>1.2-3.8(16H,m)<br>7.74(1H,d)<br>8.09(1H,d) | 2970<br>1730<br>1700<br>1400<br>1310 | Syrup |
| II-31 | B-31 | | 1.8-2.0(2H,m)<br>2.1-2.8(4H,m)<br>3.4-3.7(4H,m)<br>7.5-8.2(7H,m) | 2990<br>1730<br>1700<br>1400<br>1310<br>1280<br>1150 | Syrup |
| II-32 | B-32 | | 2.1-2.4(2H,m)<br>2.4-2.8(4H,m)<br>2.48(3H,s)<br>3.3-3.7(4H,m)<br>7.5-7.8(5H,m)<br>8.1-8.2(1H,m) | 3000<br>1730<br>1700<br>1390<br>1310<br>1280<br>1150 | Syrup |
| II-33 | B-33 | | 2.0-2.3(2H,m)<br>2.4-2.8(4H,m)<br>2.48(3H,s)<br>3.3-3.7(4H,m)<br>7.5-7.8(5H,m)<br>8.1-8.2(1H,m) | 3000<br>1730<br>1700<br>1390<br>1310<br>1280<br>1150 | Syrup |

TABLE II-1-continued

| (1) | (2) | (3) | (4) | (5) | (6) |
|---|---|---|---|---|---|
| II-34 | B-34 | | 2.0-2.3(2H,m)<br>2.4-2.8(4H,m)<br>2.47(3H,s)<br>3.3-3.7(4H,m)<br>7.40(2H,d)<br>7.7-7.9(3H,m)<br>8.16(1H,d) | 1690<br>1600<br>1400<br>1310<br>1280<br>1180<br>1150 | Syrup |
| II-35 | B-35 | | 2.1-2.3(2H,m)<br>2.5-2.8(4H,m)<br>3.3-3.7(4H,m)<br>7.4-7.8(4H,m)<br>8.0-8.1(2H,m) | 2970<br>1730<br>1700<br>1570<br>1400<br>1310<br>1280 | Syrup |
| II-36 | B-36 | | 1.23(6H,d)<br>2.0-2.3(3H,m)<br>2.4-2.7(4H,m)<br>3.3-3.7(4H,m)<br>7.3-8.2(6H,m) | 2990<br>2900<br>1680<br>1390<br>1310<br>1280<br>1120 | Syrup |
| II-37 | B-37 | | 2.0-2.2(2H,m)<br>2.4-2.8(4H,m)<br>3.4-3.7(4H,m)<br>3.90(3H,s)<br>7.0-7.1(2H,m)<br>7.7-7.9(3H,m)<br>8.16(1H,d) | 1730<br>1700<br>1390<br>1310<br>1280<br>1180<br>1150 | Syrup |
| II-38 | B-38 | | 2.1-2.4(2H,m)<br>2.5-2.7(2H,m)<br>2.8-2.9(2H,m)<br>3.4-3.7(4H,m)<br>3.94(2H,d)<br>5.4-6.2(3H,m)<br>7.72(1H,d)<br>8.06(1H,d) | 1690<br>1660<br>1590<br>1500<br>1320<br>1300<br>1150 | Syrup |
| II-39 | B-39 | | 1.42(9H,s)<br>2.1-2.4(2H,m)<br>2.5-2.7(2H,m)<br>2.8-2.9(2H,m)<br>3.4-3.7(4H,m)<br>7.72(1H,d)<br>8.13(1H,d) | 2960<br>1690<br>1300<br>1280<br>1180<br>1130<br>1100<br>810 | Syrup |

TABLE II-1-continued

| (1) | (2) | (3) | (4) | (5) | (6) |
|---|---|---|---|---|---|
| II-40 | B-40 | | 1.7-2.3(4H,m)<br>2.3-2.6(2H,m)<br>3.4-3.7(4H,m)<br>4.48(2H,s)<br>7.4-7.6(5H,m)<br>7.72(1H,d)<br>8.05(1H,d) | 2990<br>2900<br>1680<br>1390<br>1310<br>1280<br>1120 | Syrup |
| II-41 | B-41 | | 1.9-2.2(2H,m)<br>2.3-2.6(4H,m)<br>3.4-3.8(4H,m)<br>6.95(2H,d)<br>7.45(2H,d)<br>7.65(1H,d)<br>7.71(1H,d) | | |
| II-42 | B-42 | | 2.0-2.3(2H,m)<br>2.5-2.8(4H,m)<br>3.3-3.7(4H,m)<br>7.74(1H,d)<br>7.78(4H,s)<br>8.16(1H,d) | 1690<br>1570<br>1390<br>1310<br>1280<br>1180<br>1150 | Syrup |
| II-43 | B-43 | | 2.0-2.2(2H,m)<br>2.4-2.8(4H,m)<br>3.3-3.7(4H,m)<br>6.96(2H,d)<br>7.73(2H,d)<br>7.74(1H,d)<br>8.15(1H,d) | 3300<br>1690<br>1600<br>1580<br>1310<br>1280<br>1150 | syrup |
| II-44 | B-44 | | 2.1-2.4(2H,m)<br>2.5-2.8(4H,m)<br>3.4-3.7(4H,m)<br>3.92(3H,s)<br>7.6-7.8(4H,m)<br>8.0-8.2(2H,m) | 1720<br>1700<br>1670<br>1310<br>1280<br>1150<br>1140<br>1100 | Syrup |
| II-45 | B-45 | | 1.9-2.2(2H,m)<br>2.3-2.5(4H,m)<br>2.65(3H,s)<br>3.4-3.7(4H,m)<br>7.57(2H,d)<br>7.66(1H,d)<br>7.72(1H,d)<br>8.03(2H,d) | 1690<br>1680<br>1650<br>1540<br>1400<br>1300<br>1290<br>1280 | Syrup |

TABLE II-1-continued

| (1) | (2) | (3) | (4) | (5) | (6) |
|---|---|---|---|---|---|
| II-46 | B-46 | | 2.0-2.3(2H,m)<br>2.5-2.8(4H,m)<br>2.68(3H,s)<br>3.4-3.7(4H,m)<br>7.77(1H,d)<br>8.0-8.3(5H,m) | 2960<br>2900<br>1690<br>1400<br>1310<br>1280<br>1150 | Syrup |
| II-47 | B-47 | | 2.1-2.4(2H,m)<br>2.4-2.7(2H,m)<br>2.54(3H,s)<br>2.8-3.0(2H,m)<br>3.2-3.7(4H,m)<br>7.58(2H,s) | 1695<br>1675<br>1295<br>1195<br>1120<br>890 | 174–176 |
| II-48 | B-48 | | 1.8-2.1(2H,m)<br>2.2-2.8(4H,m)<br>3.2-3.6(4H,m)<br>6.23(1H,s)<br>6.7-7.8(6H,m) | 3400<br>1650<br>1570<br>1460<br>1450<br>1340<br>1310 | syrup |
| II-49 | B-49 | | 1.9-2.2(2H,m)<br>2.3-2.5(2H,m)<br>2.8-3.0(2H,m)<br>3.3-3.7(4H,m)<br>7.2-8.6(6H,m) | 2960<br>1680<br>1570<br>1410<br>1300<br>1260<br>1130 | 137–139 |
| II-50 | B-50 | | 1.24(3H,t)<br>2.0-2.3(2H,m)<br>2.4-2.6(2H,m)<br>2.6-2.8(2H,m)<br>3.3-3.7(4H,m)<br>4.08(2H,q)<br>7.65(2H,s) | 1690<br>1580<br>1380<br>1360<br>1310<br>1130<br>1040 | 180–decomp. |
| II-51 | B-51 | | 1.14(6H,d)<br>2.0-2.3(2H,m)<br>2.4-2.6(2H,m)<br>2.7-2.8(2H,m)<br>3.3-3.7(4H,m)<br>4.62(1H,m)<br>7.64(2H,s) | 1680<br>1640<br>1560<br>1400<br>1380<br>1300<br>1240 | 170–174 |

TABLE II-1-continued

| (1) | (2) | (3) | (4) | (5) | (6) |
|---|---|---|---|---|---|
| II-52 | B-52 | | 2.0-2.3(2H,m)<br>2.4-2.5(2H,m)<br>2.7-2.9(2H,m)<br>3.3-3.7(4H,m)<br>3.87(3H,s)<br>7.66(2H,s) | 1680<br>1640<br>1580<br>1380<br>1300<br>1120 | powder |
| II-53 | B-53 | | 1.9-2.2(2H,m)<br>2.3-2.6(2H,m)<br>2.7-2.9(2H,m)<br>3.29(3H,s)<br>3.3-3.7(6H,m)<br>4.1-4.2(2H,m)<br>7.66(2H,s) | 1680<br>1640<br>1570<br>1410<br>1280<br>1180 | Powder |
| II-54 | B-54 | | 2.0-2.3(2H,m)<br>2.4-2.8(2H,m)<br>2.8-3.0(2H,m)<br>2.72(3H,s)<br>2.78(3H,s)<br>3.37(4H,s)<br>4.07(3H,s)<br>7.24(1H,s) | | |
| II-55 | B-55 | | 1.8-2.1(2H,m)<br>2.2-2.4(2H,m)<br>2.44(3H,s)<br>2.63(3H,s)<br>2.6-2.8(2H,m)<br>3.19(6H,s)<br>3.29(4H,s)<br>3.99(3H,s)<br>6.98(1H,s) | | |
| II-56 | B-56 | | 2.0-2.3(2H,m)<br>2.3-2.5(2H,m)<br>2.8-3.0(2H,m)<br>2.40(3H,s)<br>2.46(3H,s)<br>2.77(3H,s)<br>3.37(4H,s)<br>4.05(3H,s)<br>7.02(1H,s) | | |
| II-57 | B-57 | | 1.9-2.2(2H,m)<br>2.3-2.6(2H,m)<br>2.6-2.8(2H,m)<br>2.62(3H,s)<br>2.68(3H,s)<br>3.32(4H,s)<br>3.36(3H,s)<br>3.63(3H,s)<br>4.02(3H,s)<br>7.24(1H,s) | | |
| II-58 | B-58 | | 1.8-2.1(2H,m)<br>2.3-2.9(4H,m)<br>2.40(3H,s)<br>2.69(3H,s)<br>3.37(4H,s)<br>4.00(3H,s)<br>6.90(1H,s)<br>7.19(2H,d)<br>7.32(2H,d) | | |

TABLE II-1-continued

| (1) | (2) | (3) | (4) | (5) | (6) |
|---|---|---|---|---|---|
| II-59 | B-59 | | 1.8-2.1(2H,m)<br>2.3-2.8(4H,m)<br>2.45(3H,s)<br>2.60(1.5H,s)<br>2.70(1.5H,s)<br>3.35(4H,s)<br>4.09(3H,s)<br>7.12(1H,s)<br>7.28(2H,d)<br>7.46(2H,d)<br>異性体混合物 | | |
| II-60 | B-60 | | 2.0-2.3(2H,m)<br>2.4-2.8(4H,m)<br>2.49(3H,s)<br>2.68(1.5H,s)<br>2.72(1.5H,s)<br>2.73(3H,s)<br>3.3-3.4(4H,m)<br>4.04(3H,s)<br>7.20(1H,s)<br>7.38(2H,d)<br>7.77(2H,d)<br>異性体混合物 | | |
| II-61 | B-61 | | 1.05(3H,t)<br>1.5-1.9(2H,m)<br>2.0-2.7(6H,m)<br>2.51(3H,s)<br>2.64(3H,s)<br>2.8-3.0(2H,m)<br>3.36(4H,s)<br>4.03(3H,s)<br>7.04(1H,s) | | |
| II-62 | B-62 | | 1.10(3H,t)<br>1.7-2.0(2H,m)<br>2.2-2.4(2H,m)<br>2.6-2.8(2H,m)<br>2.64(3H,s)<br>2.66(3H,s)<br>2.8-3.0(2H,m)<br>3.0-3.4(6H,m)<br>4.08(3H,s)<br>7.32(1H,s) | | |
| II-63 | B-63 | | 1.48(6H,s)<br>2.0-2.4(2H,m)<br>2.4-2.6(2H,m)<br>2.61(3H,s)<br>2.8-3.0(2H,m)<br>3.46(2H,s)<br>7.69(1H,d)<br>7.85(1H,d) | 2980<br>1720<br>1680<br>1620<br>1320<br>1290<br>1190<br>1030 | 178–180 |
| II-64 | B-64 | | 1.48(6H,s)<br>1.5-2.2(4H,m)<br>2.3-2.6(2H,m)<br>2.51(3H,s)<br>3.46(2H,s)<br>7.46(4H,s)<br>7.51(1H,d)<br>7.82(1H,d) | 3000<br>2980<br>1700<br>1640<br>1590<br>1560<br>1310<br>1290 | 209–211 |

TABLE II-1-continued

| (1) | (2) | (3) | (4) | (5) | (6) |
|---|---|---|---|---|---|
| II-65 | B-65 | | 1.48(6H,s)<br>1.9-2.2(2H,m)<br>2.3-2.6(2H,m)<br>2.35(3H,s)<br>2.7-2.9(2H,m)<br>3.48(2H,s)<br>7.4-7.9(6H,m) | 3000<br>2980<br>1730<br>1690<br>1560<br>1320<br>1200 | |
| II-66 | B-66 | | 1.2-1.4(6H,m)<br>2.0-3.0(6H,m)<br>2.57(3H,s)<br>2.73(3H,s)<br>3.0-3.4(1H,m)<br>3.7-4.2(2H,m)<br>4.8-5.0(1H,m)<br>7.25(1H,s) | 2980<br>2940<br>1690<br>1660<br>1610<br>1300<br>1280<br>1110 | 198–199 |
| II-67 | B-67 | | 1.2-1.4(6H,m)<br>2.0-2.2(2H,m)<br>2.4-3.0(6H,m)<br>2.42(3H,s)<br>2.46(3H,s)<br>2.70(3H,s)<br>3.0-3.3(1H,m)<br>3.7-4.2(2H,m)<br>2.70(3H,s)<br>3.0-3.3(1H,m)<br>3.7-4.2(2H,m)<br>4.8-4.9(1H,m)<br>7.08(1H,s) | 2960<br>2940<br>1640<br>1350<br>1280<br>1190<br>1120<br>1050<br>1190<br>1120<br>1050<br>960<br>910 | Syrup |
| II-68 | B-68 | | 1.2-1.4(6H,m)<br>1.8-2.1(2H,m)<br>2.3-2.8(6H,m)<br>2.41(3H,s)<br>2.74(3H,s)<br>3.1-3.3(1H,m)<br>3.7-4.1(2H,m)<br>4.8-5.0(1H,m)<br>7.17(1H,s)<br>7.4-7.6(5H,m) | 2980<br>2940<br>1730<br>1660<br>1440<br>1280<br>1260<br>1190<br>1120<br>1050 | Syrup |
| II-69 | B-69 | | 1.2-1.4(6H,m)<br>1.9-2.2(2H,m)<br>2.3-2.9(6H,m)<br>2.55(3H,s)<br>2.73(3H,s)<br>3.01(3H,s)<br>3.1-3.4(1H,m)<br>3.7-4.2(2H,m)<br>4.9-5.0(1H,m)<br>7.49(1H,s) | 2980<br>2940<br>1720<br>1700<br>1440<br>1380<br>1320<br>1300<br>1140<br>1120 | Syrup |
| II-70 | B-70 | | 1.2-1.4(6H,m)<br>2.0-2.2(2H,m)<br>2.4-3.0(6H,m)<br>2.47(3H,s)<br>2.60(3H,s)<br>3.0-3.3(1H,m)<br>3.7-4.0(2H,m)<br>4.12(2H,s)<br>4.8-4.9(1H,m)<br>7.01(1H,s)<br>7.2-7.3(5H,m) | 2980<br>2940<br>1660<br>1450<br>1340<br>1300<br>1280<br>1190<br>1120<br>1050<br>910 | syrup |

TABLE II-1-continued

| (1) | (2) | (3) | (4) | (5) | (6) |
|---|---|---|---|---|---|
| II-71 | B-71 | | 1.2-1.4(6H,m)<br>1.8-2.0(2H,m)<br>2.0-2.8(6H,m)<br>2.65(3H,s)<br>2.70(3H,s)<br>3.1-3.4(1H,m)<br>3.7-4.2(2H,m)<br>4.48(2H,s)<br>4.9-5.0(1H,m)<br>7.32(1H,s)<br>7.3-7.6(5H,m) | 2980<br>2930<br>1660<br>1450<br>1290<br>1270<br>1160<br>1120<br>1050<br>910<br>750 | Syrup |
| II-72 | B-72 | | 2.1-2.4(2H,m)<br>2.4-2.6(2H,m)<br>2.72(3H,s)<br>2.8-3.0(2H,m)<br>3.33(3H,s)<br>4.07(3H,s)<br>7.55(1H,d)<br>7.87(1H,d) | 2940<br>1700<br>1670<br>1620<br>1420<br>1310<br>1280<br>1180 | Syrup |
| II-73 | B-73 | | 2.0-2.3(2H,m)<br>2.4-2.6(2H,m)<br>2.45(3H,s)<br>2.58(3H,s)<br>2.8-3.0(2H,m)<br>3.32(4H,m)<br>4.05(3H,s)<br>7.30(1H,d)<br>7.83(1H,d) | 2940<br>1660<br>1530<br>1350<br>1280<br>1220<br>1180<br>1150<br>1040 | Syrup |
| II-74 | B-74 | | 1.8-2.1(2H,m)<br>2.3-2.5(4H,m)<br>2.64(3H,s)<br>3.33(4H,m)<br>4.06(3H,s)<br>7.39(1H,d)<br>7.4-7.6(5H,m)<br>7.85(1H,d) | 2940<br>1740<br>1660<br>1520<br>1410<br>1340<br>1310<br>1240 | Syrup |
| II-75 | B-75 | | 2.0-2.2(2H,m)<br>2.4-2.9(4H,m)<br>2.43(1.5H,s)<br>2.87(1.5H,s)<br>3.33(4H,m)<br>4.04(1.5H,s)<br>4.08(1.5H,s)<br>7.2-8.0(7H,m)<br>異性体混合物 | 2940<br>1680<br>1560<br>1450<br>1420<br>1310<br>1280<br>1150<br>1120 | Syrup |
| II-76 | B-76 | | 1.9-2.2(2H,m)<br>2.2-2.5(2H,m)<br>2.6-2.8(2H,m)<br>2.70(3H,s)<br>3.26(3H,s)<br>3.31(4H,m)<br>3.56(3H,s)<br>4.05(3H,s)<br>7.59(1H,d)<br>7.78(1H,d) | 2980<br>1670<br>1590<br>1410<br>1310<br>1280<br>1190<br>1120<br>970<br>990 | powder |

TABLE II-1-continued

| (1) | (2) | (3) | (4) | (5) | (6) |
|---|---|---|---|---|---|
| II-77 | B-77 | (structure) | 2.0-2.3(2H,m)<br>2.4-2.8(4H,m)<br>2.8-3.2(4H,m)<br>3.3-3.5(2H,m)<br>7.67(1H,d)<br>7.94(1H,d) | 1690<br>1670<br>1610<br>1310<br>1290<br>1140 | 185–190 |
| II-78 | B-78 | (structure) | 1.9-2.1(2H,m)<br>2.3-2.7(6H,m)<br>2.9-3.2 (2H,m)<br>3.2-3.5(2H,m)<br>7.48(1H,d)<br>7.5-7.6(5H,m)<br>7.94(1H,d) | 1680<br>1660<br>1470<br>1340<br>1310<br>1290<br>1280 | |
| II-79 | B-79 | (structure) | 2.0-2.3(2H,m)<br>2.4-2.7(4H,m)<br>2.50(3H,s)<br>2.9-3.2(4H,m)<br>3.3-3.5(2H,m)<br>7.35(1H,d)<br>7.90(1H,d) | | powder |
| II-80 | B-90 | (structure) | 2.1-2.3(2H,m)<br>2.4-2.7(4H,m)<br>2.8-3.2(4H,m)<br>3.09(3H,s)<br>3.3-3.5(2H,m)<br>7.98(2H,s) | 1680<br>1380<br>1310<br>1140<br>930<br>820 | syrup |
| II-81 | B-81 | (structure) | 1.9-2.3(4H,m)<br>2.11(3H,s)<br>2.4-2.8(4H,m)<br>2.9-3.2(4H,m)<br>3.2-3.7(4H,m)<br>7.50(1H,d)<br>7.69(1H,d) | 1655<br>1345<br>1305<br>1280<br>1180<br>1135 | |

Example II-82~161

Biological tests of Herbicide were carried out in the same manner as described in Example I-22, except that the respective triketone derivatives prepared in Examples II-1 to II-81 were used instead of the herbicide prepared in Example I-22.

The results of the biological tests are shown in Table II-2.

In the Table II-2, "(1)" to "(11)" indicates respectively as follows.

(1) Example No.
(2) Compound No.
(3) Dose (g/ha)
(4) Treatment performed 3 days after transplantation
(5) Treatment performed 10 days after transplantation
(6) Weed-killing effect
(7) Chemical injury
(8) *Echinochloa crug-galli*
(9) *Scirups juncoides*
(10) Transplanted paddy rice plant

TABLE II-2

| | | | (4) | | | (5) | |
|---|---|---|---|---|---|---|---|
| | | | (6) | | (7) | (6) | |
| (1) | (2) | (3) | (8) | (9) | (10) | (8) | (9) |
| II-82 | B-1 | 100 | 5 | 5 | 0 | 4 | 5 |
| | | 200 | 5 | 5 | 0 | 5 | 5 |
| II-83 | B-2 | 100 | 4 | 5 | 0 | 3 | 4 |
| | | 200 | 5 | 5 | 0 | 4 | 5 |

TABLE II-2-continued

| (1) | (2) | (3) | (4) | | | (5) | |
|---|---|---|---|---|---|---|---|
| | | | (6) | | (7) | (6) | |
| | | | (8) | (9) | (10) | (8) | (9) |
| II-84 | B-3 | 100 | 3 | 4 | 0 | 3 | 4 |
| | | 200 | 4 | 5 | 0 | 4 | 5 |
| II-85 | B-4 | 100 | 5 | 5 | 1 | 4 | 5 |
| | | 200 | 5 | 5 | 2 | 5 | 5 |
| II-86 | B-5 | 100 | 4 | 4 | 0 | 3 | 4 |
| | | 200 | 4 | 4 | 0 | 4 | 4 |
| II-87 | B-6 | 100 | 5 | 5 | 0 | 4 | 5 |
| | | 200 | 5 | 5 | 0 | 5 | 5 |
| II-88 | B-7 | 100 | 4 | 5 | 0 | 4 | 4 |
| | | 200 | 5 | 5 | 0 | 4 | 5 |
| II-89 | B-8 | 100 | 4 | 5 | 0 | 4 | 5 |
| | | 200 | 5 | 5 | 0 | 4 | 5 |
| II-90 | B-9 | 100 | 4 | 5 | 0 | 4 | 4 |
| | | 200 | 5 | 5 | 0 | 4 | 5 |
| II-91 | B-10 | 100 | 3 | 4 | 0 | 3 | 4 |
| | | 200 | 5 | 5 | 0 | 4 | 5 |
| II-92 | B-11 | 100 | 3 | 4 | 0 | 3 | 4 |
| | | 200 | 4 | 5 | 0 | 3 | 5 |
| II-93 | B-12 | 100 | 5 | 5 | 0 | 5 | 5 |
| | | 200 | 5 | 5 | 1 | 5 | 5 |
| II-94 | B-13 | 100 | 3 | 4 | 0 | 3 | 4 |
| | | 200 | 4 | 4 | 0 | 3 | 4 |
| II-95 | B-14 | 100 | 3 | 4 | 0 | 3 | 4 |
| | | 200 | 4 | 5 | 0 | 4 | 5 |
| II-96 | 3-15 | 100 | 3 | 4 | 0 | 3 | 4 |
| | | 200 | 4 | 5 | 0 | 4 | 5 |
| II-97 | B-16 | 100 | 3 | 4 | 0 | 3 | 4 |
| | | 200 | 4 | 5 | 0 | 4 | 5 |
| II-98 | B-17 | 100 | 3 | 4 | 0 | 3 | 4 |
| | | 200 | 4 | 5 | 0 | 4 | 5 |
| II-99 | B-18 | 100 | 3 | 4 | 0 | 3 | 4 |
| | | 200 | 4 | 4 | 0 | 4 | 4 |
| II-100 | B-19 | 100 | 3 | 4 | 0 | 3 | 4 |
| | | 200 | 4 | 4 | 0 | 4 | 4 |
| II-101 | B-20 | 100 | 3 | 4 | 0 | 3 | 4 |
| | | 200 | 4 | 5 | 0 | 4 | 5 |
| II-102 | B-21 | 100 | 3 | 4 | 0 | 3 | 4 |
| | | 200 | 4 | 5 | 0 | 4 | 5 |
| II-103 | B-22 | 100 | 4 | 5 | 0 | 4 | 5 |
| | | 200 | 5 | 5 | 0 | 5 | 5 |
| II-104 | B-23 | 100 | 4 | 5 | 0 | 4 | 5 |
| | | 200 | 5 | 5 | 0 | 5 | 5 |
| II-105 | B-24 | 100 | 5 | 5 | 0 | 4 | 5 |
| | | 200 | 5 | 5 | 0 | 5 | 5 |
| II-106 | B-25 | 100 | 5 | 5 | 0 | 4 | 5 |
| | | 200 | 5 | 5 | 1 | 5 | 5 |
| II-107 | B-26 | 100 | 4 | 4 | 0 | 4 | 4 |
| | | 200 | 5 | 5 | 0 | 4 | 5 |
| II-108 | B-27 | 100 | 5 | 5 | 0 | 4 | 5 |
| | | 200 | 5 | 5 | 0 | 5 | 5 |
| II-109 | B-28 | 100 | 4 | 4 | 0 | 4 | 4 |
| | | 200 | 5 | 5 | 0 | 4 | 5 |
| II-110- | B-29 | 100 | 4 | 4 | 0 | 4 | 4 |
| | | 200 | 5 | 5 | 0 | 4 | 5 |
| II-111 | B-30 | 100 | 4 | 4 | 0 | 3 | 4 |
| | | 200 | 4 | 5 | 0 | 4 | 5 |
| II-112 | B-31 | 100 | 4 | 4 | 0 | 3 | 4 |
| | | 200 | 4 | 5 | 0 | 4 | 5 |
| II-113 | B-32 | 100 | 3 | 4 | 0 | 3 | 4 |
| | | 200 | 4 | 5 | 0 | 4 | 5 |
| II-114 | B-33 | 100 | 4 | 4 | 0 | 3 | 4 |
| | | 200 | 4 | 5 | 0 | 4 | 5 |
| II-115 | B-34 | 100 | 4 | 4 | 0 | 3 | 4 |
| | | 200 | 4 | 5 | 0 | 4 | 5 |
| II-116 | B-35 | 100 | 3 | 4 | 0 | 3 | 4 |
| | | 200 | 4 | 5 | 0 | 4 | 5 |
| II-117 | B-36 | 100 | 3 | 4 | 0 | 3 | 4 |
| | | 200 | 4 | 5 | 0 | 4 | 4 |
| II-118 | B-37 | 100 | 4 | 4 | 0 | 3 | 4 |
| | | 200 | 4 | 5 | 0 | 4 | 5 |
| II-119 | B-38 | 100 | 5 | 5 | 0 | 4 | 5 |
| | | 200 | 5 | 5 | 0 | 5 | 5 |
| II-120 | B-39 | 100 | 5 | 5 | 0 | 4 | 5 |
| | | 200 | 5 | 5 | 0 | 5 | 5 |
| II-121 | B-40 | 100 | 4 | 4 | 0 | 3 | 4 |
| | | 200 | 5 | 5 | 0 | 5 | 5 |
| II-122 | B-41 | 100 | 3 | 4 | 0 | 3 | 4 |
| | | 200 | 4 | 5 | 0 | 4 | 5 |
| II-123 | B-42 | 100 | 4 | 4 | 0 | 3 | 4 |
| | | 200 | 4 | 5 | 0 | 4 | 5 |
| II-124 | B-43 | 100 | 4 | 4 | 0 | 3 | 4 |
| | | 200 | 4 | 5 | 0 | 4 | 5 |
| II-125 | B-44 | 100 | 3 | 4 | 0 | 3 | 4 |
| | | 200 | 4 | 5 | 0 | 4 | 4 |
| II-126 | B-45 | 100 | 3 | 4 | 0 | 3 | 4 |
| | | 200 | 4 | 5 | 0 | 4 | 5 |
| II-127 | B-46 | 100 | 4 | 4 | 0 | 3 | 4 |
| | | 200 | 4 | 5 | 0 | 4 | 5 |
| II-126 | B-47 | 100 | 4 | 5 | 0 | 3 | 5 |
| | | 200 | 5 | 5 | 0 | 4 | 5 |
| II-129 | B-48 | 100 | 4 | 4 | 0 | 3 | 4 |
| | | 200 | 4 | 5 | 0 | 4 | 5 |
| II-130 | B-49 | 100 | 4 | 4 | 0 | 3 | 4 |
| | | 200 | 4 | 5 | 0 | 4 | 5 |
| II-131 | B-50 | 100 | 5 | 5 | 0 | 4 | 5 |
| | | 200 | 5 | 5 | 0 | 5 | 5 |
| II-132 | B-51 | 100 | 5 | 5 | 0 | 4 | 5 |
| | | 200 | 5 | 5 | 0 | 5 | 5 |
| II-133 | B-52 | 100 | 5 | 5 | 0 | 4 | 5 |
| | | 200 | 5 | 5 | 0 | 5 | 5 |
| II-134 | B-53 | 100 | 5 | 5 | 0 | 4 | 5 |
| | | 200 | 5 | 5 | 0 | 5 | 5 |
| II-135 | B-54 | 100 | 5 | 3 | 1 | 4 | 2 |
| | | 200 | 5 | 5 | 4 | 5 | 5 |
| II-136 | B-55 | 100 | 0 | 0 | 0 | 0 | 0 |
| | | 200 | 1 | 2 | 0 | 1 | 2 |
| II-137 | B-56 | 100 | 5 | 3 | 0 | 4 | 2 |
| | | 200 | 5 | 4 | 0 | 5 | 3 |
| II-138 | B-57 | 100 | 5 | 3 | 0 | 4 | 2 |
| | | 200 | 5 | 4 | 3 | 5 | 3 |
| II-139 | B-58 | 100 | 0 | 0 | 0 | 0 | 0 |
| | | 200 | 1 | 1 | 0 | 1 | 1 |
| II-140 | B-59 | 100 | 5 | 5 | 0 | 4 | 3 |
| | | 200 | 5 | 5 | 0 | 5 | 5 |
| II-141 | B-60 | 100 | 3 | 2 | 0 | 3 | 2 |
| | | 200 | 4 | 4 | 0 | 4 | 4 |
| II-142 | B-61 | 100 | 1 | 1 | 0 | 1 | 1 |
| | | 200 | 5 | 4 | 0 | 5 | 3 |
| II-143 | B-62 | 100 | 2 | 1 | 0 | 2 | 1 |
| | | 200 | 5 | 5 | 0 | 5 | 4 |
| II-144 | B-63 | 100 | 2 | 5 | 3 | 2 | 4 |
| | | 200 | 5 | 5 | 5 | 5 | 5 |
| II-145 | B-64 | 100 | 5 | 3 | 2 | 3 | 3 |
| | | 200 | 5 | 5 | 5 | 5 | 5 |
| II-146 | B-65 | 100 | 5 | 5 | 3 | 4 | 4 |
| | | 200 | 5 | 5 | 4 | 5 | 5 |
| II-147 | B-66 | 100 | 5 | 5 | 0 | 5 | 3 |
| | | 200 | 5 | 5 | 4 | 5 | 5 |
| II-148 | B-67 | 100 | 4 | 3 | 0 | 4 | 2 |
| | | 200 | 5 | 5 | 1 | 5 | 5 |
| II-149 | B-68 | 100 | 3 | 3 | 0 | 3 | 2 |
| | | 200 | 5 | 4 | 0 | 5 | 4 |
| II-150 | B-69 | 100 | 4 | 4 | 0 | 4 | 3 |
| | | 200 | 5 | 5 | 1 | 5 | 5 |
| II-151 | B-70 | 100 | 3 | 3 | 0 | 2 | 2 |
| | | 200 | 5 | 4 | 0 | 5 | 4 |
| II-152 | B-71 | 100 | 4 | 4 | 0 | 4 | 3 |
| | | 200 | 5 | 5 | 1 | 5 | 5 |
| II-153 | B-72 | 100 | 4 | 1 | 0 | 3 | 1 |
| | | 200 | 5 | 5 | 0 | 5 | 4 |
| II-154 | B-73 | 100 | 5 | 1 | 0 | 4 | 1 |
| | | 200 | 5 | 5 | 0 | 5 | 4 |
| II-155 | B-74 | 100 | 5 | 2 | 0 | 4 | 1 |
| | | 200 | 5 | 4 | 0 | 5 | 4 |
| II-156 | B-75 | 100 | 5 | 4 | 0 | 4 | 3 |
| | | 200 | 5 | 5 | 1 | 5 | 5 |

TABLE II-2-continued

| | | | (4) | | | (5) | |
|---|---|---|---|---|---|---|---|
| | | | (6) | (7) | | (6) | |
| (1) | (2) | (3) | (8) | (9) | (10) | (8) | (9) |
| II-157 | B-76 | 100 | 5 | 3 | 0 | 4 | 3 |
| | | 200 | 5 | 5 | 1 | 5 | 5 |
| II-158 | B-77 | 100 | 4 | 5 | 0 | 4 | 5 |
| | | 200 | 5 | 5 | 0 | 5 | 5 |
| II-159 | B-78 | 100 | 3 | 5 | 0 | 3 | 5 |
| | | 200 | 5 | 5 | 0 | 5 | 5 |
| II-160 | B-79 | 100 | 3 | 5 | 0 | 3 | 5 |
| | | 200 | 5 | 5 | 0 | 5 | 5 |
| II-161 | B-80 | 100 | 4 | 5 | 0 | 4 | 5 |
| | | 200 | 5 | 5 | 0 | 5 | 5 |
| II-162 | B-81 | 100 | 5 | 5 | 0 | 4 | 5 |
| | | 200 | 5 | 5 | 0 | 5 | 5 |

Industrial Applicability

As described hereinabove, the present invention provides a herbicide containing a triketone derivative as an active ingredient, which herbicide can control a wide range of weeds at a low dose and imparts a low level of chemical injury to cultivated crops, particularly a paddy rice plant.

What is claimed is:

1. A triketone derivative represented by formula [I-2]:

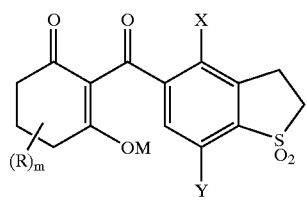

[I-2]

wherein

R represents a methyl group;

each of X and Y represents a hydrogen atom, a halogen atom, a nitro group, an amino group, a cyano group, a hydroxyl group, a mercapto group, —$R^1$, —$OR^1$, —$SR^1$, —$SO_2R^1$, —$NR^2R^3$, or —$NHCOR^1$, wherein $R^1$ represent C1–C6 alkyl group which may have a branched structure, a cyclic structure, or an unsaturated bond, a C1–C6 haloalkyl group which may have a branched structure, a cyclic structure, or an unsaturated bond, a phenyl group which may be substituted, or a benzyl group which may be substituted;

each of $R^2$ and $R^3$ represents a hydrogen atom, a C1–C6 alkyl group which may have a branched structure, a cyclic structure, or an unsaturated bond, a C1–C6 haloalkyl group which may have a branched structure, a cyclic structure, or an unsaturated bond, a phenyl group which may be substituted, or a benzyl group which may be substituted, or $R^2$ and $R^3$ may be bonded to each other to form a group having a cyclic structure; M represents a hydrogen atom, an alkali metal, an alkaline earth metal, or an organic base; and m is an integer between 0 and 4 inclusive.

2. The triketone derivative according to claim 1, wherein Y represents a hydrogen atom, a C1–C6 alkyl group, or a halogen atom.

3. The triketone derivative according to claim 1, wherein Y represents a hydrogen atom or a methyl group.

4. The triketone derivative according to claim 1, wherein Y represents a hydrogen atom.

5. The triketone derivative according to claim 1, wherein X represents —$R^1$, —$OR^1$, or —$SR^1$.

6. The triketone derivative according to claim 1, wherein X represents a halogen atom or a methyl group.

7. The triketone derivative according to claim 1, wherein M represents a hydrogen atom.

8. A herbicide containing a triketone derivative as recited in claim 1 as an active ingredient.

9. The herbicide according to claim 8, which is for use in cultivation of a paddy rice plant.

10. A triketone derivative represented by formula [I-4]:

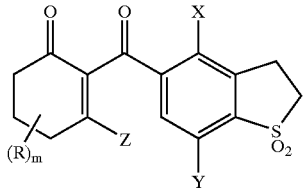

wherein

R represents a methyl group;

each of X and Y represents a hydrogen atom, a halogen atom, a nitro group, an amino group, a cyano group, a hydroxyl group, a mercapto group, —$R^1$, —$OR^1$, —$SR^1$, —$SO_2R^1$, —$NR^2R^3$, or —$NHCOR^1$, wherein $R^1$ represent C1–C6 alkyl group which may have a branched structure, a cyclic structure, or an unsaturated bond, a C1–C6 haloalkyl group which may have a branched structure, a cyclic structure, or an unsaturated bond, a phenyl group which may be substituted, or a benzyl group which may be substituted;

each of $R^2$ and $R^3$ represents a hydrogen atom, a C1–C6 alkyl group which may have a branched structure, a cyclic structure, or an unsaturated bond, a C1–C6 haloalkyl group which may have a branched structure, a cyclic structure, or an unsaturated bond, a phenyl group which may be substituted, or a benzyl group which may be substituted, or $R^2$ and $R^3$ may be bonded to each other to form a group having a cyclic structure); Z represents a halogen atom, —$OR^1$, —$SO_pR^1$, —$A(CH_2)_nQR^1$, —$NR^2R^3$, —$N(OR^1)R^2$, —$O(C=O)R^1$, —$O(C=O)OR^1$, —$O(C=O)SR^1$, —$O(C=O)NR^2R^3$, or —$O(C=S)NR^2R^3$, wherein $R^1$, $R^2$, and $R^3$ have the same definitions as described in relation to X, each of A and Q represents an oxygen atom or a sulfur atom, p is 0, 1, or 2, n is 1 to 3, or a halogen atom;

m is an integer between 0 and 4 inclusive; and q is 1 or 2.

11. The triketone derivative according to claim 10, wherein Y represents a hydrogen atom, a C1–C6 alkyl group, or a halogen atom.

12. The triketone derivative according to claim 10, wherein Y represents a hydrogen atom or a methyl group.

13. The triketone derivative according to claim 10, wherein Y represents a hydrogen atom.

14. The triketone derivative according to claim 10, wherein X represents halogen atom, $-R^1$, $-OR^1$, or $-SR^1$.

15. The triketone derivative according to claim 10, wherein X represents a halogen atom or a methyl group.

16. The triketone derivative according to claim 10, wherein Z represents a halogen atom, $-OR^1$, $-SO_pR^1$, $-A(CH_2)_nQR^1$, or $-N(OR^1)R^2$.

17. A herbicide containing a triketone derivative as recited in claim 10 as an active ingredient.

18. The herbicide according to claim 17, which is for use in cultivation of a paddy rice plant.

* * * * *